United States Patent
Usui et al.

(10) Patent No.: US 10,370,484 B2
(45) Date of Patent: Aug. 6, 2019

(54) POLYMER COMPOUND AND LIGHT EMITTING DEVICE USING THE SAME

(71) Applicant: Sumitomo Chemical Company, Limited, Tokyo (JP)

(72) Inventors: Motoaki Usui, Tsukuba (JP); Daisuke Fukushima, Tsukuba (JP); Shin-ya Tanaka, Tsukuba (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 233 days.

(21) Appl. No.: 15/322,851

(22) PCT Filed: Jun. 26, 2015

(86) PCT No.: PCT/JP2015/068464
§ 371 (c)(1),
(2) Date: Dec. 29, 2016

(87) PCT Pub. No.: WO2016/002646
PCT Pub. Date: Jan. 7, 2016

(65) Prior Publication Data
US 2017/0137566 A1    May 18, 2017

(30) Foreign Application Priority Data

Jul. 3, 2014    (JP) .................................. 2014-137464

(51) Int. Cl.
*H01L 51/54* (2006.01)
*C09K 11/06* (2006.01)
(Continued)

(52) U.S. Cl.
CPC ......... *C08G 61/124* (2013.01); *C07D 487/04* (2013.01); *C08G 61/12* (2013.01); *C09K 11/06* (2013.01); *H01L 51/0035* (2013.01); *H01L 51/0043* (2013.01); *H01L 51/50* (2013.01); *C08G 2261/12* (2013.01); *C08G 2261/148* (2013.01); *C08G 2261/3241* (2013.01); *C08G 2261/95* (2013.01); *H01L 51/5012* (2013.01); *H01L 51/5056* (2013.01);
(Continued)

(58) Field of Classification Search
CPC ................ C09K 11/06; C09K 2211/10; C09K 2211/1007; C09K 2211/1029; C08G 61/00; C08G 61/12; C08G 61/124; C08G 2261/12; C08G 2261/128; C08G 2261/3241; C08G 2261/95; C07D 487/00; C07D 487/02; C07D 487/04; H01L 51/0032; H01L 51/0035; H01L 51/0043; H01L 51/005; H01L 51/0072; H01L 51/0073; H01L 51/0074; H01L 51/50; H01L 51/5012; H01L 51/5016; H01L 51/5056; H01L 51/5072; H01L 51/5088; H01L 51/5092

USPC ....... 428/690, 691, 917, 411.4, 336; 427/58, 427/66; 313/500–512; 257/40, 88–104, 257/E51.001–E51.052; 252/301.16–301.35
See application file for complete search history.

(56) References Cited

U.S. PATENT DOCUMENTS

2006/0063033 A1    3/2006  Sohn et al.
2006/0149022 A1*   7/2006  Parham ................ C08G 61/124
                                                   528/102
(Continued)

FOREIGN PATENT DOCUMENTS

CN        1749295 A      3/2006
JP     2006083386 A      3/2006
(Continued)

OTHER PUBLICATIONS

Blouin et al. Polymer Preprints 2007, 48, 292-293. (Year: 2007).*
(Continued)

*Primary Examiner* — Andrew K Bohaty
(74) *Attorney, Agent, or Firm* — Panitch Schwarze Belisario & Nadel LLP

(57) ABSTRACT

Provided is a polymer compound which is useful for production of a light emitting device excellent in light emission efficiency is provided. The polymer compound contains a constitutional unit represented by the formula (1) and a constitutional unit represented by the formula (Y) as follows:

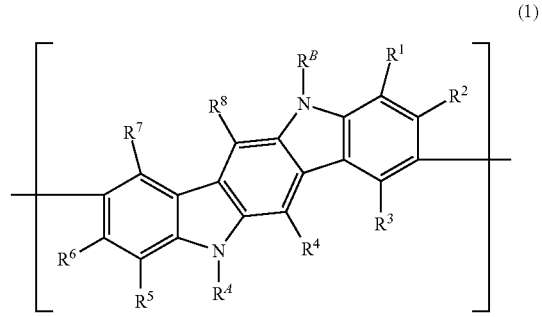

(1)

wherein $R^1$ to $R^8$ represent a hydrogen atom, an alkyl group, an aryl group or the like, and $R^A$ and $R^B$ represent an aryl group or a monovalent heterocyclic group, and $$\mathrm{-\!\!\!+\!Ar^{Y1}\!\!+\!\!\!-}$$ (Y)

wherein $Ar^{Y1}$ represents an arylene group or the like.

13 Claims, No Drawings

(51) Int. Cl.
    *C08G 61/12*       (2006.01)
    *H01L 51/50*       (2006.01)
    *C07D 487/04*     (2006.01)
    *H01L 51/00*       (2006.01)

(52) U.S. Cl.
    CPC ...... *H01L 51/5072* (2013.01); *H01L 51/5088* (2013.01); *H01L 51/5092* (2013.01)

(56) References Cited

U.S. PATENT DOCUMENTS

| | | | |
|---|---|---|---|
| 2007/0112167 A1 | 5/2007 | Li et al. | |
| 2009/0261300 A1* | 10/2009 | Watanabe | C07C 17/12 |
| | | | 252/500 |
| 2011/0060097 A1 | 3/2011 | Wang | |
| 2011/0187266 A1* | 8/2011 | Fukushima | C08G 61/02 |
| | | | 313/504 |
| 2011/0240968 A1 | 10/2011 | Kim et al. | |
| 2012/0007070 A1 | 1/2012 | Kai et al. | |
| 2012/0153272 A1 | 6/2012 | Fukuzaki | |
| 2012/0235133 A1 | 9/2012 | Kai et al. | |
| 2014/0117289 A1 | 5/2014 | Pan et al. | |

FOREIGN PATENT DOCUMENTS

| | | |
|---|---|---|
| JP | 2007019294 A | 1/2007 |
| JP | 2009224216 A | 10/2009 |
| JP | 2011216484 A | 10/2011 |
| JP | 201256880 A | 3/2012 |
| WO | 2010113761 A1 | 10/2010 |
| WO | 2011025018 A1 | 3/2011 |
| WO | 2011080972 A1 | 7/2011 |
| WO | 2012171609 A1 | 12/2012 |

OTHER PUBLICATIONS

Office Action dated May 29, 2018 in CN Application No. 201580035550.X.

Aleksandrova et al., "Spectroscopic Study of Polyphenylquinolines—Materials with Efficient Intramolecular Charge Transfer," Optics and Spectroscopy, vol. 114, No. 5, pp. 737-750 (2013).

Search Report dated Dec. 21, 2017 in EP Application No. 15815714 (Partial).

Velasco et al, "Indolo[3,2-b]Carbazole Derivatives as Hole Transporting Materials for Electrophotography", Synthetic Metals, vol. 159, No. 7-8, pp. 654-658 (2009).

Xia et al, "An Alternating Copolymer Derived from Indolo[3,2-b]Carbazole and 4,7-Di(thieno[3,2-b]thien-2-yl)-2,1,3-Benzothiadiazole for Photovoltaic Cells", Macromolecular Rapid Communications, vol. 31, No. 14, p. 1287-1292 (2010).

Li et al, "Polyindolo[3,2-b]carbazoles: A New Class of p-Channel Semiconductor Polymer for Organic Thin-Film Transistors", Macromolecules, vol. 39, No. 19, pp. 6521-6527 (2006).

Extended European Search Report dated Mar. 28, 2018 in EP Application No. 15815714.9.

Office Action dated Feb. 19, 2019 in CN Application No. 201580035550.X.

Office Action dated Mar. 22, 2019 in JP Application No. 2016-531329 (Machine English Translation).

* cited by examiner

POLYMER COMPOUND AND LIGHT EMITTING DEVICE USING THE SAME

CROSS-REFERENCE TO RELATED APPLICATION

This application is a Section 371 of International Application No. PCT/JP2015/068464, filed Jun. 26, 2015, which was published in the Japanese language on Jan. 7, 2016 under International Publication No. WO 2016/002646 A1, and the disclosure of which is incorporated herein by reference.

TECHNICAL FIELD

The present invention relates to a polymer compound and a light emitting device using the same.

BACKGROUND ART

An organic electroluminescent device (hereinafter, referred to also as "light emitting device") can be suitably used for applications of displays and illumination and is recently attracting attention, because of high light emission efficiency and low driving voltage. This light emitting device has organic layers such as a light emitting layer, a charge transporting layer and the like. Polymer compounds used for production of a light emitting device are investigated because an organic layer can be formed by an application method typified by an inkjet printing method, by use of a polymer compound.

As the material used in a light emitting layer of a light emitting device, for example, a polymer compound comprising an indrocarbazole constitutional unit represented by the following formula and an arylene constitutional unit is investigated (Patent document 1).

[Chemical Formula 1]

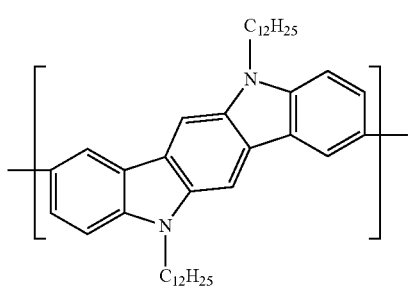

As the method of producing an indrocarbazole compound, for example, a method of making a halogenated aryl compound and a secondary amine compound undergo Ullmann-reacting in the presence of a copper catalyst, a base and a solvent (a reaction method represented by the following formula) is known (Patent document 2). The indrocarbazole compound can be suitably used as a raw material monomer of a polymer compound or a material used in an organic layer of a light emitting layer.

[Chemical Formula 2]

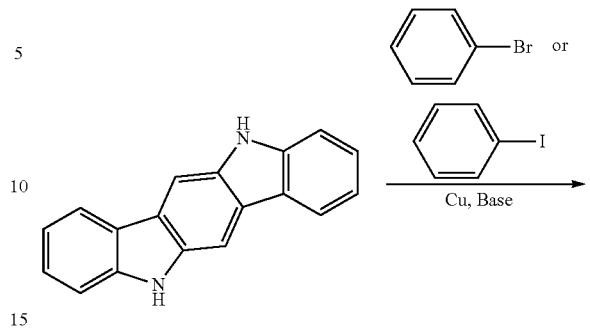

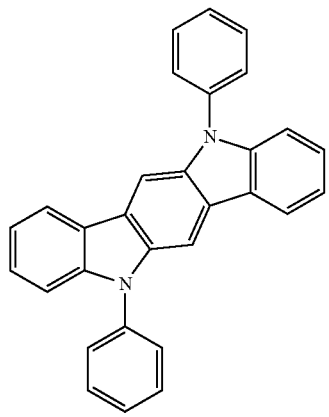

PRIOR ART DOCUMENT

Patent Document

[Patent document 1] U.S. Patent Application Publication Nos. 2007/0112167

[Patent document 2] International Publication WO2010/113761

SUMMARY OF THE INVENTION

Problem to be Solved by the Invention

A light emitting device produced by using the polymer compound, however, has not necessarily sufficient light emission efficiency. Further, in the production method, the yield of the resultant indrocarbazole compound is not necessarily sufficient.

Then, the present invention has an object of providing a polymer compound which is useful for production of a light emitting device excellent in light emission efficiency. Also, the present invention has an object of providing a compound which is useful for production of the polymer compound. Further, the present invention has an object of providing a composition containing the polymer compound and a light emitting device obtained by using the polymer compound.

Still further, the present invention has an object of providing a production method of an indrocarbazole compound excellent in yield.

Means for Solving the Problem

The present invention provides the following [1] to [13].

[1] A polymer compound comprising a constitutional unit represented by the following formula (1) and a constitutional unit represented by the following formula (Y) (different from the constitutional unit represented by the formula (1)),

[Chemical Formula 3]

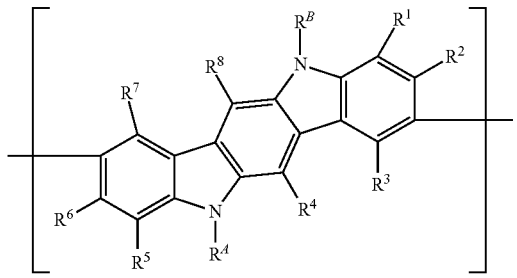

(1)

[wherein, $R^1$, $R^2$, $R^3$, $R^4$, $R^5$, $R^6$, $R^7$ and $R^8$ each independently represent a hydrogen atom, an alkyl group, a cycloalkyl group, an alkoxy group, a cycloalkoxy group, an aryl group, an aryloxy group or a monovalent heterocyclic group, the foregoing groups each optionally having a substituent. $R^1$ and $R^2$, $R^3$ and $R^4$, $R^5$ and $R^6$, and $R^7$ and $R^8$ each may be combined together to form a ring together with the carbon atoms to which they are attached.

$R^A$ and $R^B$ each independently represent an aryl group or a monovalent heterocyclic group, these groups each optionally having a substituent.]

[Chemical Formula 4]

 (Y)

[wherein, $Ar^{Y1}$ represents an arylene group, a divalent heterocyclic group or a divalent group in which at least one arylene group and at least one divalent heterocyclic group are bonded directly to each other, the foregoing groups each optionally having a substituent.].

[2] The polymer compound according to [1], wherein the constitutional unit represented by the formula (1) is a constitutional unit represented by the following formula (1-1):

[Chemical Formula 5]

(1-1)

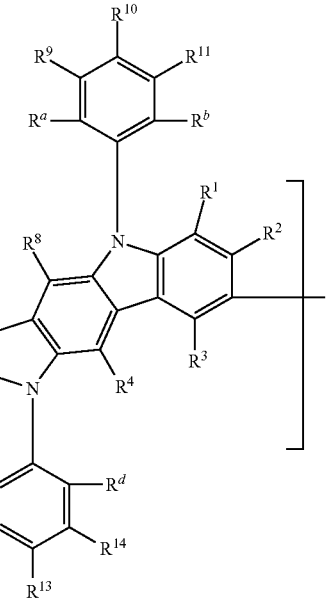

[wherein,
$R^1$, $R^2$, $R^3$, $R^4$, $R^5$, $R^6$, $R^7$ and $R^8$ are as defined above. $R^9$, $R^{10}$, $R^{11}$, $R^{12}$, $R^{13}$, $R^{14}$, $R^a$, $R^b$, $R^c$ and $R^d$ each independently represent a hydrogen atom, an alkyl group, a cycloalkyl group, an alkoxy group, a cycloalkoxy group, an aryl group, an aryloxy group or a monovalent heterocyclic group, the foregoing groups each optionally having a substituent. R and $R^9$, $R^{10}$, $R^{10}$ and $R^{11}$, $R^{12}$ and $R^{13}$, and $R^{13}$ and $R^{14}$ each may be combined together to form a ring together with the carbon atoms to which they are attached.].

[3] The polymer compound according to [2], wherein $R^a$, $R^b$, $R^c$ and $R^d$ are an alkyl group optionally having a substituent.

[4] The polymer compound according to any one of [1] to [3], wherein the constitutional unit represented by the formula (Y) is a constitutional unit represented by the following formula (Y-2):

[Chemical Formula 6]

(Y-2)

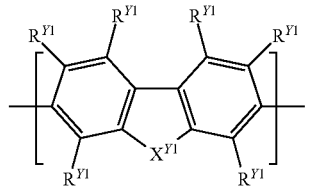

[wherein,
each $R^{Y1}$ represents a hydrogen atom, an alkyl group, a cycloalkyl group, an alkoxy group, a cycloalkoxy group, an aryl group or a monovalent heterocyclic group, the foregoing groups each optionally having a substituent. The plurality of $R^{Y1}$ may be the same or different, with the proviso that adjacent groups $R^{Y1}$ may be combined together to form a ring together with carbon atoms to which they are attached.

$X^{Y1}$ represents a group represented by —C(R$^{Y2}$)$_2$—, a group represented by —C(R$^{Y2}$)=C(R$^{Y2}$)— or a group represented by —C(R$^{Y2}$)$_2$—C(R$^{Y2}$)$_2$—. Each $R^{Y2}$ represents a hydrogen atom, an alkyl group, a cycloalkyl group, an alkoxy group, a cycloalkoxy group, an aryl group or a monovalent heterocyclic group, the foregoing groups each optionally having a substituent. The plurality of $R^{Y2}$ may be the same or different, with the proviso that groups $R^{Y2}$ may be combined together to form a ring together with the carbon atoms to which they are attached.].

[5] The polymer compound according to any one of [1] to [3], wherein the constitutional unit represented by the formula (Y) is a constitutional unit represented by the following formula (Y-5), (Y-6) or (Y-7):

[Chemical Formula 7]

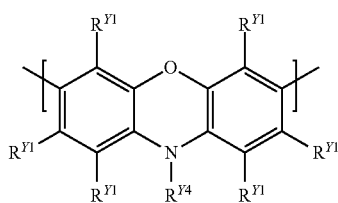
(Y-5)

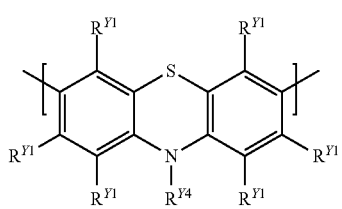
(Y-6)

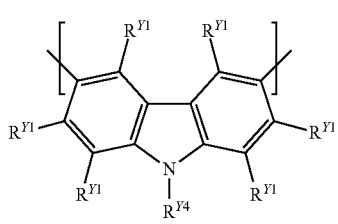
(Y-7)

[wherein, each $R^{Y1}$ represents a hydrogen atom, an alkyl group, a cycloalkyl group, an alkoxy group, a cycloalkoxy group, an aryl group or a monovalent heterocyclic group, the foregoing groups each optionally having a substituent. The plurality of $R^{Y1}$ may be the same or different, with the proviso that adjacent $R^{Y1}$ may be combined together to form a ring together with carbon atoms to which they are attached.

$R^{Y4}$ represents a hydrogen atom, an alkyl group, a cycloalkyl group, an alkoxy group, a cycloalkoxy group, an aryl group or a monovalent heterocyclic group, the foregoing groups each optionally having a substituent.].

[6] The polymer compound according to any one of [1] to [5], further comprising a constitutional unit represented by the following formula (X):

[Chemical Formula 8]

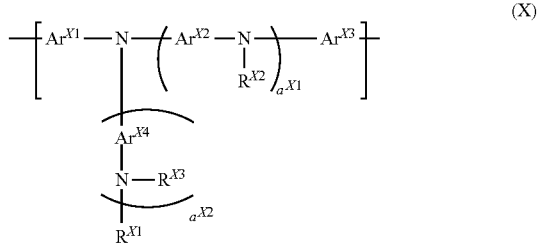
(X)

[wherein, $a^{X1}$ and $a^{X2}$ each independently represent an integer of 0 or more.

$Ar^{X1}$ and $Ar^{X3}$ each independently represent an arylene group or a divalent heterocyclic group, the foregoing groups each optionally having a substituent.

$Ar^{X2}$ and $Ar^{X4}$ each independently represent an arylene group, a divalent heterocyclic group or a divalent group in which at least one arylene group and at least one divalent heterocyclic group are bonded directly, these groups each optionally having a substituent.

$R^{X1}$, $R^{X2}$ and $R^{X3}$ each independently represent a hydrogen atom, an alkyl group, a cycloalkyl group, an aryl group or a monovalent heterocyclic group, the foregoing groups each optionally having a substituent.].

[7] The polymer compound according to any one of [1] to [6], wherein the content of the constitutional unit represented by the formula (1) is 0.1 to 50 mol % with respect to the total content of constitutional units contained in the polymer compound.

[8] A compound represented by the following formula (M-1-2):

[Chemical Formula 9]

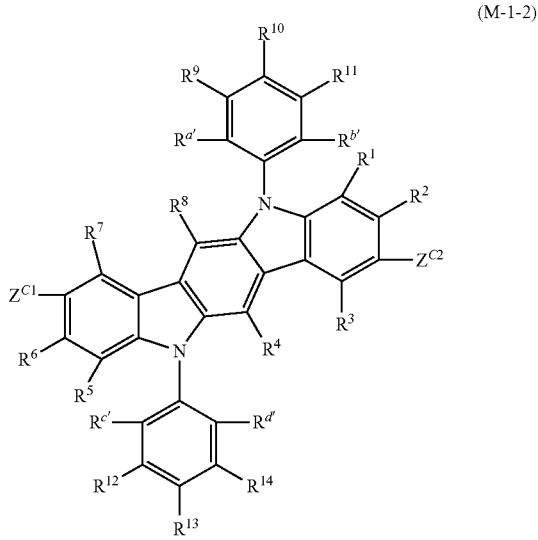
(M-1-2)

[wherein, $R^1$, $R^2$, $R^3$, $R^4$, $R^5$, $R^6$, $R^7$ and $R^8$ each independently represent a hydrogen atom, an alkyl group, a cycloalkyl group, an alkoxy group, a cycloalkoxy group, an aryl group, an aryloxy group or a monovalent heterocyclic group, the foregoing groups each optionally having a substituent. $R^1$ and $R^2$, $R^3$ and $R^4$, $R^5$ and $R^6$, and $R^7$ and $R^8$ each may be combined together to form a ring together with carbon atoms to which they are attached.

$R^9$, $R^{10}$, $R^{11}$, $R^{12}$, $R^{13}$ and $R^{14}$ each independently represent a hydrogen atom, an alkyl group, a cycloalkyl group, an alkoxy group, a cycloalkoxy group, an aryl group, an aryloxy group or a monovalent heterocyclic group, the foregoing groups each optionally having a substituent. $R^9$ and $R^{10}$, $R^{10}$ and $R^{11}$, $R^{12}$ and $R^{13}$, and $R^{13}$ and $R^{14}$ each may be combined together to form a ring together with carbon atoms to which they are attached.

$R^{a1}$, $R^{b1}$, $R^{c1}$ and $R^{d1}$ each independently represent an alkyl group, a cycloalkyl group, an alkoxy group, a cycloalkoxy group, an aryl group, an aryloxy group or a monovalent heterocyclic group, the foregoing groups each optionally having a substituent.

$Z^{C1}$ and $Z^{C2}$ each independently represent a group selected from the group consisting of Group A of substituents and Group B of substituents described below.

<Group A of Substituents> a hydrogen atom, a chlorine atom, a bromine atom, an iodine atom, a group represented by —O—S(=O)$_2$R$^{C1}$ (wherein, $R^{C1}$ represents an alkyl group, a cycloalkyl group or an aryl group, the foregoing groups each optionally having a substituent.).

<Group B of Substituents> a group represented by —B(OR$^{C2}$)$_2$ (wherein, each $R^{C2}$ represents a hydrogen atom, an alkyl group, a cycloalkyl group or an aryl group, the foregoing groups each optionally having a substituent. The plurality of $R^{C2}$ may be the same or different, and may be combined together to form a cyclic structure together with oxygen atoms to which they are attached.);

a group represented by —BF$_3$Q' (wherein, Q' represents Li, Na, K, Rb or Cs.);

a group represented by —MgY' (wherein, Y' represents a chlorine atom, a bromine atom or an iodine atom.);

a group represented by —ZnY'' (wherein, Y'' represents a chlorine atom, a bromine atom or an iodine atom.); and a group represented by —Sn(R$^{C3}$)$_3$ (wherein, each $R^{C3}$ represents a hydrogen atom, an alkyl group, a cycloalkyl group or an aryl group, the foregoing groups each optionally having a substituent. The plurality of $R^{C3}$ may be the same or different, and may be combined together to form a cyclic structure together with tin atoms to which they are attached.)].

[9] A composition comprising the polymer compound according to any one of [1] to [7], and at least one material selected from the group consisting of a hole transporting material, a hole injection material, an electron transporting material, an electron injection material, a light emitting material, an antioxidant and a solvent.

[10] A light emitting device produced by using the polymer compound according to any one of [1] to [7].

[11] A method for producing a compound represented by the following formula (M-1'), comprising a step of making a compound represented by the following formula (Z) and a compound represented by the following formula (2) undergo amination, in the presence of a transition metal complex having a phosphine ligand, a base and a solvent,

[Chemical Formula 10]

$$R^C—NH_2 \qquad (Z)$$

[wherein, $R^C$ represents an aryl group or a monovalent heterocyclic group, these groups each optionally having a substituent.]

[Chemical Formula 11]

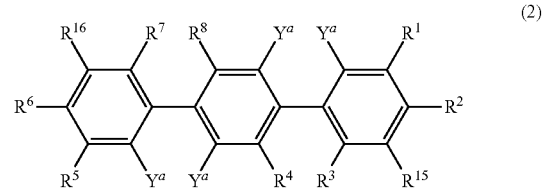

(2)

[wherein, $R^1$, $R^2$, $R^3$, $R^4$, $R^5$, $R^6$, $R^7$ and $R^8$ each independently represent a hydrogen atom, an alkyl group, a cycloalkyl group, an alkoxy group, a cycloalkoxy group, an aryl group, an aryloxy group or a monovalent heterocyclic group, the foregoing groups each optionally having a substituent.

$R^{15}$ and $R^{16}$ each independently represent an alkyl group, a cycloalkyl group, an alkoxy group, a cycloalkoxy group, an aryl group, an aryloxy group or a monovalent heterocyclic group, or a group selected from the group consisting of Group A of substituents and Group B of substituents described above, the foregoing groups each optionally having a substituent.

$R^1$ and $R^2$, $R^2$ and $R^{15}$, $R^{15}$ and $R^3$, $R^3$ and $R^4$, $R^5$ and $R^6$, $R^6$ and $R^{16}$, $R^{16}$ and $R^7$, and $R^7$ and $R^8$ each may be combined together to form a ring together with the carbon atoms to which they are attached.

Each $Y^a$ represents a chlorine atom, a bromine atom, an iodine atom or —O—S(=O)$_2$R$^{C1}$. $R^{C1}$ represents an alkyl group, a cycloalkyl group or an aryl group, the foregoing groups each optionally having a substituent. The plurality of $Y^a$ may be the same or different.]

[Chemical Formula 12]

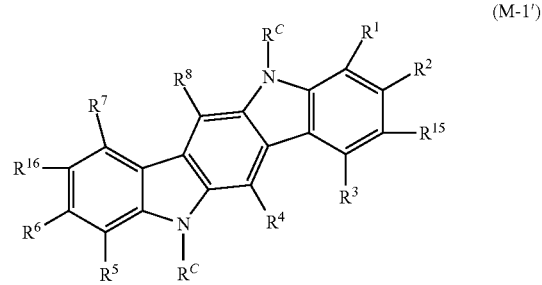

(M-1')

[wherein, $R^1$, $R^2$, $R^3$, $R^4$, $R^5$, $R^6$, $R^7$, $R^7$, $R^{15}$, $R^{16}$ and each $R^C$ are as defined above. The plurality of $R^c$ may be the same or different.].

[12] The method for producing a compound according to [11], wherein the compound represented by the formula (M-1') is a compound represented by the following formula (M-1'-1):

[Chemical Formula 13]

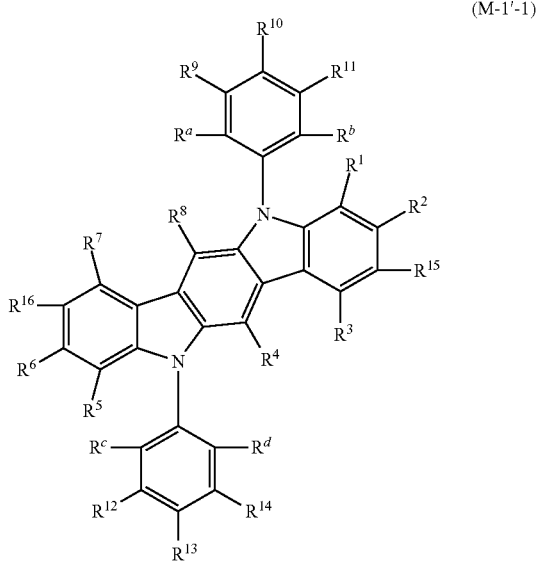

(M-1'-1)

[wherein, $R^1$, $R^2$, $R^3$, $R^4$, $R^5$, $R^6$, $R^7$, $R^8$, $R^{15}$ and $R^{16}$ are as defined above.

$R^9$, $R^{10}$, $R^{11}$, $R^{12}$, $R^{13}$, $R^{14}$, $R^a$, $R^b$, $R^c$ and $R^d$ each independently represent a hydrogen atom, an alkyl group, a cycloalkyl group, an alkoxy group, a cycloalkoxy group, an aryl group, an aryloxy group or a monovalent heterocyclic group, the foregoing groups each optionally having a substituent. $R^9$ and $R^{10}$, $R^{10}$ and $R^{11}$, $R^{12}$ and $R^{13}$, and $R^{13}$ and $R^{14}$ each may be combined together to form a ring together with the carbon atoms to which they are attached.].

[13] The method for producing a compound according to [12], wherein $R^a$, $R^b$, $R^c$ and $R^d$ represent each an alkyl group optionally having a substituent.

Effect of the Invention

The present invention can provide a polymer compound which is useful for production of a light emitting device excellent in light emission efficiency. Also, the present invention can provide a compound which is useful for production of the polymer compound. Further, the present invention can provide a composition containing the polymer compound and a light emitting device obtained by using the polymer compound.

Additionally, the present invention can provide a production method of an indrocarbazole compound excellent in yield. Still further, according to a preferable embodiment of the present invention, a production method of an indrocarbazole compound excellent in reaction speed can be provided.

MODES FOR CARRYING OUT THE INVENTION

Suitable embodiments of the present invention will be illustrated in detail below.

<Explanation Of Common Term>

Terms commonly used in the present specification have the following meanings unless otherwise stated.

Me represents a methyl group, Et represents an ethyl group, Bu represents a butyl group, i-Pr represents an isopropyl group, and t-Bu represents a tert-butyl group.

A hydrogen atom may be a light hydrogen atom or a heavy hydrogen atom.

A solid line representing a bond to a central metal in a formula representing a metal complex denotes a coordinate bond or a covalent bond.

"Polymer compound" denotes a polymer having molecular weight distribution and having a polystyrene-equivalent number average molecular weight of $1\times10^3$ to $1\times10^8$.

"Low molecular weight compound" denotes a compound having no molecular weight distribution and having a molecular weight of $1\times10^4$ or less.

"Constitutional unit" denotes a unit structure found once or more in a polymer compound.

"Alkyl group" may be any of linear or branched. The number of carbon atoms of the linear alkyl group is, not including the number of carbon atoms of a substituent, usually 1 to 50, preferably 3 to 30, more preferably 4 to 20. The number of carbon atoms of the branched alkyl groups is, not including the number of carbon atoms of a substituent, usually 3 to 50, preferably 3 to 30, more preferably 4 to 20.

The alkyl group optionally has a substituent, and examples thereof include a methyl group, an ethyl group, a propyl group, an isopropyl group, a butyl group, an isobutyl group, a tert-butyl group, a pentyl group, an isoamyl group, a 2-ethylbutyl group, a hexyl group, a heptyl group, a octyl group, a 2-ethylhexyl group, a 3-propylheptyl group, a decyl group, a 3,7-dimethyloctyl group, a 2-ethyloctyl group, a 2-hexyldecyl group and a dodecyl group, and groups obtained by substituting a hydrogen atom in the foregoing groups with a cycloalkyl group, an alkoxy group, a cycloalkoxy group, an aryl group, a fluorine atom or the like, and the alkyl group having a substituent includes a trifluoromethyl group, a pentafluoroethyl group, a perfluorobutyl group, a perfluorohexyl group, a perfluorooctyl group, a 3-phenylpropyl group, a 3-(4-methylphenyl)propyl group, a 3-(3,5-di-n-hexylphenyl) propyl group and a 6-ethyloxyhexyl group.

The number of carbon atoms of "Cycloalkyl group" is, not including the number of carbon atoms of a substituent, usually 3 to 50, preferably 3 to 30, more preferably 4 to 20.

The cycloalkyl group optionally has a substituent, and examples thereof include a cyclohexyl group, a cyclohexylmethyl group and a cyclohexylethyl group.

"Aryl group" denotes an atomic group remaining after removing from an aromatic hydrocarbon one hydrogen atom linked directly to a carbon atom constituting the ring. The number of carbon atoms of the aryl group is, not including the number of carbon atoms of a substituent, usually 6 to 60, preferably 6 to 20, more preferably 6 to 10.

The aryl group optionally has a substituent, and examples thereof include a phenyl group, a 1-naphthyl group, a 2-naphthyl group, a 1-anthracenyl group, a 2-anthracenyl group, a 9-anthracenyl group, a 1-pyrenyl group, a 2-pyrenyl group, a 4-pyrenyl group, a 2-fluorenyl group, a 3-fluorenyl group, a 4-fluorenyl group, a 2-phenylphenyl group, a 3-phenylphenyl group, a 4-phenylphenyl group, and groups obtained by substituting a hydrogen atom in the foregoing groups with an alkyl group, a cycloalkyl group, an alkoxy group, a cycloalkoxy group, an aryl group, a fluorine atom or the like.

"Alkoxy group" may be any of linear or branched. The number of carbon atoms of the linear alkoxy group is, not including the number of carbon atoms of a substituent, usually 1 to 40, preferably 4 to 10. The number of carbon atoms of the branched alkoxy group is, not including the number of carbon atoms of a substituent, usually 3 to 40, preferably 4 to 10.

The alkoxy group optionally has a substituent, and examples thereof include a methoxy group, an ethoxy group, a propyloxy group, an isopropyloxy group, a butyloxy group, an isobutyloxy group, a tert-butyloxy group, a pentyloxy group, a hexyloxy group, a heptyloxy group, a octyloxy group, a 2-ethylhexyloxy group, a nonyloxy group, a decyloxy group, a 3,7-dimethyloctyloxy group and a lauryloxy group, and groups obtained by substituting a hydrogen atom in the foregoing groups with a cycloalkyl group, an alkoxy group, a cycloalkoxy group, an aryl group, a fluorine atom or the like.

The number of carbon atoms of "Cycloalkoxy group" is, not including the number of carbon atoms of a substituent, usually 3 to 40, preferably 4 to 10.

The cycloalkoxy group optionally has a substituent, and examples thereof include a cyclohexyloxy group.

The number of carbon atoms of "Aryloxy group" is, not including the number of carbon atoms of a substituent, usually 6 to 60, preferably 7 to 48.

The aryloxy group optionally has a substituent, and examples thereof include a phenoxy group, a 1-naphthyloxy group, a 2-naphthyloxy group, a 1-anthracenyloxy group, a 9-anthracenyloxy group, a 1-pyrenyloxy group, and groups obtained by substituting a hydrogen atom in the foregoing groups with an alkyl group, a cycloalkyl group, an alkoxy group, a cycloalkoxy group, a fluorine atom or the like.

"p-Valent heterocyclic group" (p represents an integer of 1 or more) denotes an atomic group remaining after removing from a heterocyclic compound p hydrogen atoms among hydrogen atoms directly linked to a carbon atom or a hetero atom constituting the ring. Of p-valent heterocyclic groups, "p-valent aromatic heterocyclic groups" as an atomic group remaining after removing from an aromatic heterocyclic compound p hydrogen atoms among hydrogen atoms directly linked to a carbon atom or a hetero atom constituting the ring are preferable.

"Aromatic heterocyclic compound" denotes a compound in which the heterocyclic ring itself shows aromaticity such as oxadiazole, thiadiazole, thiazole, oxazole, thiophene, pyrrole, phosphole, furan, pyridine, pyrazine, pyrimidine, triazine, pyridazine, quinoline, isoquinoline, carbazole, dibenzosilole and dibenzophosphole, and a compound in which an aromatic ring is condensed to the heterocyclic ring even if the heterocyclic ring itself shows no aromaticity such as phenoxazine, phenothiazine, dibenzoborole, dibenzosilole and benzopyran.

The number of carbon atoms of the monovalent heterocyclic group is, not including the number of carbon atoms of a substituent, usually 2 to 60, preferably 4 to 20.

The monovalent heterocyclic group optionally has a substituent, and examples thereof include a thienyl group, a pyrrolyl group, a furyl group, a pyridyl group, a piperidyl group, a quinolyl group, an isoquinolyl group, a pyrimidinyl group, a triazinyl group, and groups obtained by substituting a hydrogen atom in the foregoing groups with an alkyl group, a cycloalkyl group, an alkoxy group, a cycloalkoxy group or the like.

"Halogen atom" denotes a fluorine atom, a chlorine atom, a bromine atom or an iodine atom.

"Amino group" optionally has a substituent, and a substituted amino group is preferable. The substituent which an amino group has is preferably an alkyl group, a cycloalkyl group, an aryl group or a monovalent heterocyclic group.

The substituted amino group includes, for example, a dialkylamino group, a dicycloalkylamino group and a diarylamino group.

The amino group includes, for example, a dimethylamino group, a diethylamino group, a diphenylamino group, a bis(4-methylphenyl)amino group, a bis(4-tert-butylphenyl) amino group and a bis(3,5-di-tert-butylphenyl)amino group.

"Alkenyl group" may be any of linear or branched. The number of carbon atoms of the linear alkenyl group, not including the number of carbon atoms of the substituent, is usually 2 to 30, preferably 3 to 20. The number of carbon atoms of the branched alkenyl group, not including the number of carbon atoms of the substituent, is usually 3 to 30, preferably 4 to 20.

The number of carbon atoms of "Cycloalkenyl group", not including the number of carbon atoms of the substituent, is usually 3 to 30, preferably 4 to 20.

The alkenyl group and cycloalkenyl group each optionally have a substituent, and examples thereof include a vinyl group, a 1-propenyl group, a 2-propenyl group, a 2-butenyl group, a 3-butenyl group, a 3-pentenyl group, a 4-pentenyl group, a 1-hexenyl group, a 5-hexenyl group, a 7-octenyl group, and the foregoing groups having a substituent.

"Alkynyl group" may be any of linear or branched. The number of carbon atoms of the alkynyl group, not including the number of carbon atoms of the substituent, is usually 2 to 20, preferably 3 to 20. The number of carbon atoms of the branched alkynyl group, not including the number of carbon atoms of the substituent, is usually 4 to 30, preferably 4 to 20.

The number of carbon atoms of "Cycloalkynyl group", not including the number of carbon atoms of the substituent, is usually 4 to 30, preferably 4 to 20.

The alkynyl group and cycloalkynyl group each optionally have a substituent, and examples thereof include an ethynyl group, a 1-propynyl group, a 2-propynyl group, a 2-butynyl group, a 3-butynyl group, a 3-pentynyl group, a 4-pentynyl group, a 1-hexenyl group, a 5-hexenyl group, the foregoing groups having a substituent.

"Arylene group" denotes an atomic group remaining after removing from an aromatic hydrocarbon two hydrogen atoms linked directly to carbon atoms constituting the ring. The number of carbon atoms of the arylene group is, not including the number of carbon atoms of a substituent, usually 6 to 60, preferably 6 to 30, more preferably 6 to 18.

The arylene group optionally has a substituent, and examples thereof include a phenylene group, a naphthalenediyl group, an anthracenediyl group, a phenanthrenediyl group, a dihydrophenanthrenediyl group, a naphthacenediyl group, a fluorenediyl group, a pyrenediyl group, a perylenediyl group, a chrysenediyl group, the foregoing groups having a substituent, preferably, groups represented by the formulae (A-1) to (A-20). The arylene group includes groups obtained by linking a plurality of the foregoing groups.

[Chemical Formula 14]
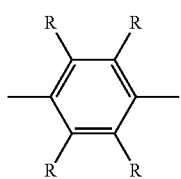 (A-1)
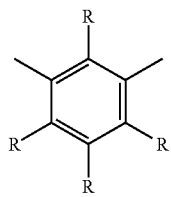 (A-2)
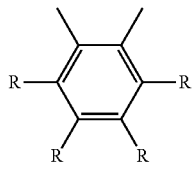 (A-3)
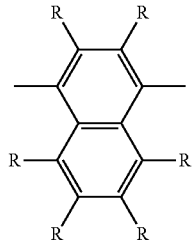 (A-4)
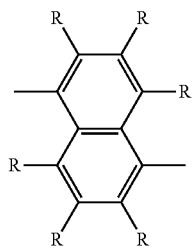 (A-5)
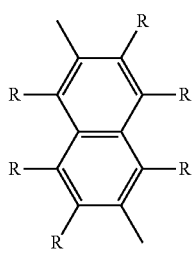 (A-6)
[Chemical Formula 15]
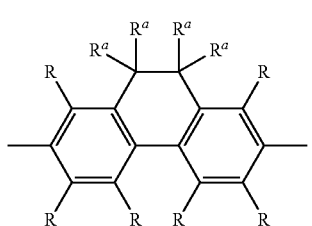 (A-7)
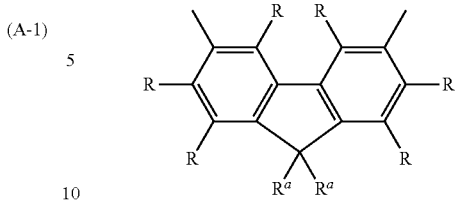 (A-8)
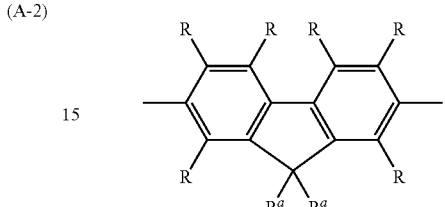 (A-9)
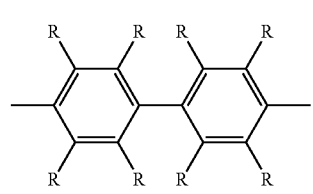 (A-10)
[Chemical Formula 16]
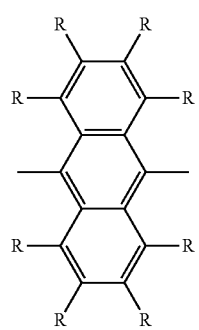 (A-11)
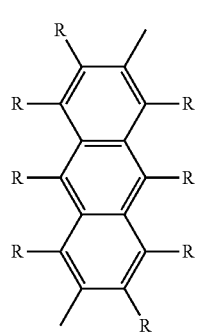 (A-12)
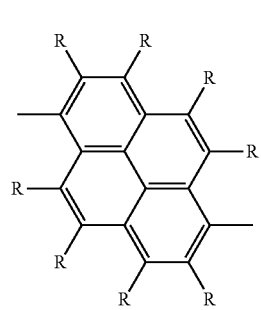 (A-13)

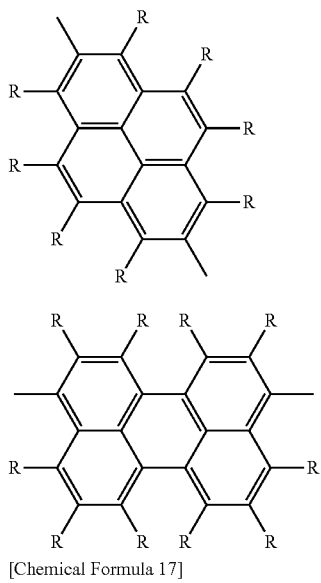
(A-14)

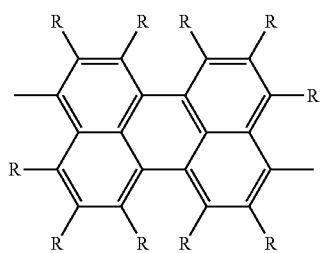
[Chemical Formula 17]
(A-15)

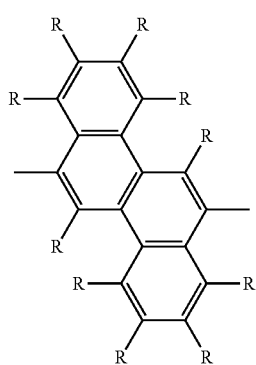
(A-16)

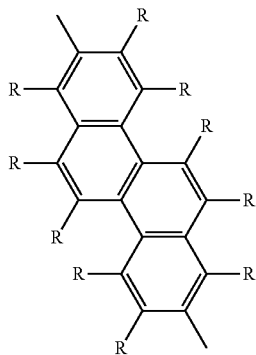
(A-17)

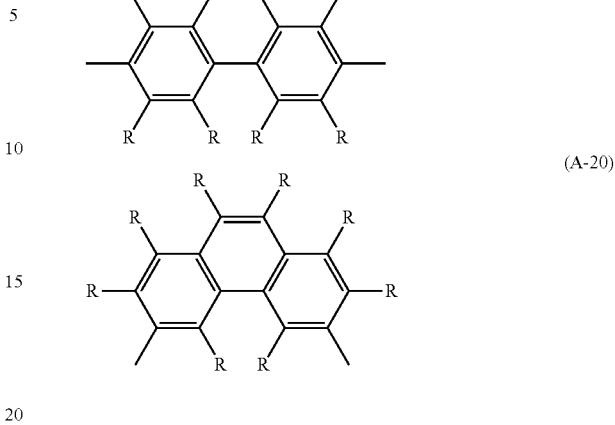
(A-18)

(A-19)

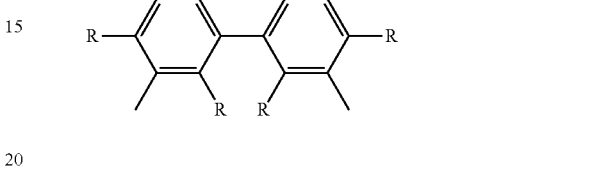
(A-20)

[wherein, R and $R^a$ each independently represent a hydrogen atom, an alkyl group, a cycloalkyl group, an aryl group or a monovalent heterocyclic group. The plurality of R and $R^a$ each may be the same or different, with the proviso that adjacent $R^a$s may be combined together to form a ring together with the atoms to which they are attached.]

The number of carbon atoms of the divalent heterocyclic group is, not including the number of carbon atoms of a substituent, usually 2 to 60, preferably 3 to 30, more preferably 4 to 15.

The divalent heterocyclic group optionally has a substituent, and examples thereof include divalent groups obtained by removing from pyridine, diazabenzene, triazine, azanaphthalene, diazanaphthalene, carbazole, dibenzofuran, dibenzothiophene, dibenzosilole, phenoxazine, phenothiazine, acridine, dihydroacridine, furan, thiophene, azole, diazole and triazole two hydrogen atoms among hydrogen atoms linking directly to a carbon atom or a hetero atom constituting the ring, preferably groups represented by the formulae (AA-1) to (AA-34). The divalent heterocyclic group includes groups obtained by linking a plurality of the foregoing groups.

[Chemical Formula 18]

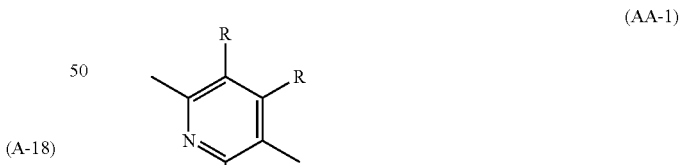
(AA-1)

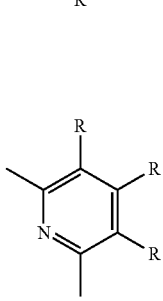
(AA-2)

(AA-3) 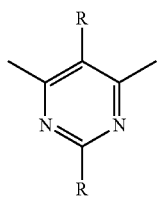
(AA-4) 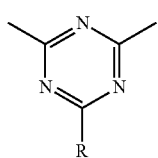
(AA-5) 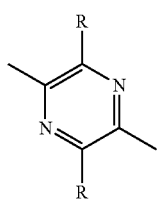
(AA-6) 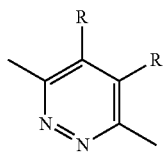
[Chemical Formula 19]
(AA-7) 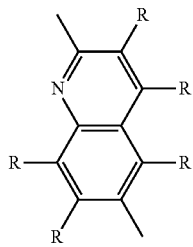
(AA-8) 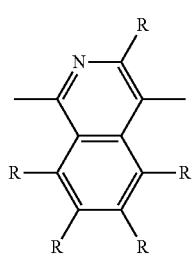
(AA-9) 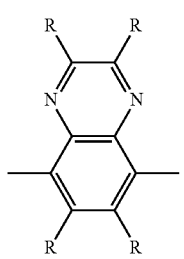
(AA-10) 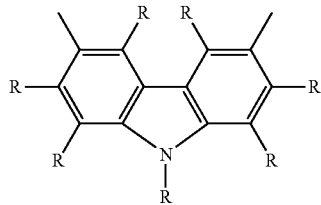
(AA-11) 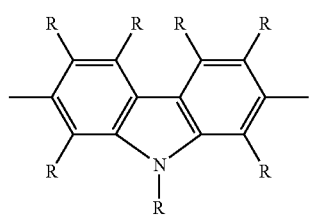
(A-12) 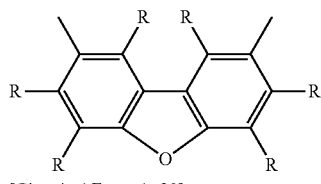
[Chemical Formula 20]
(AA-13) 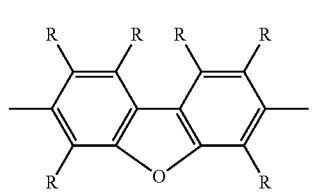
(AA-14) 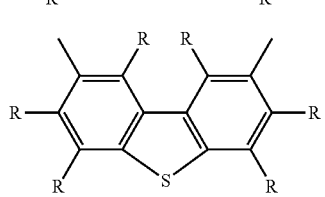
(AA-15) 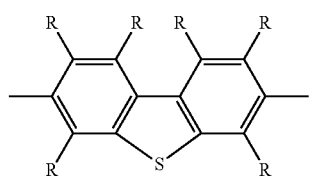
(AA-16) 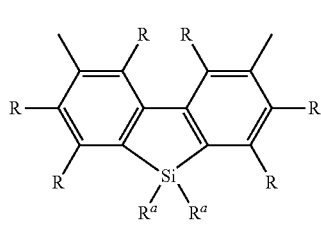

[Chemical Formula 21]
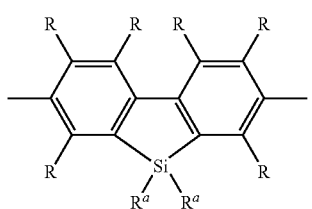 (AA-17)
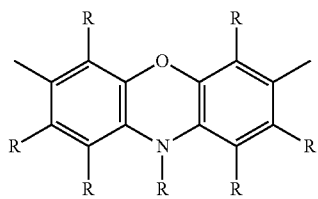 (AA-18)
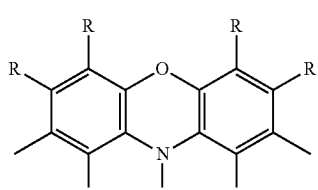 (AA-19)
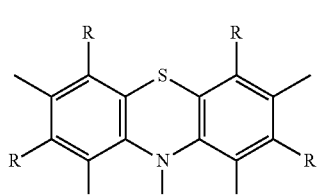 (AA-20)
[Chemical Formula 22]
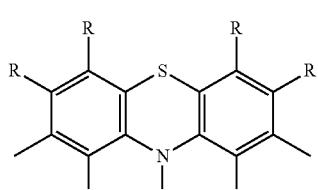 (AA-21)
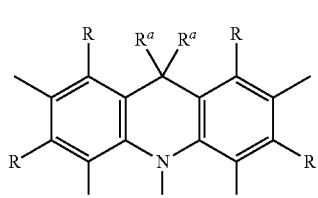 (AA-22)
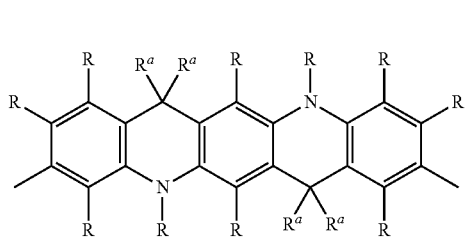 (AA-23)
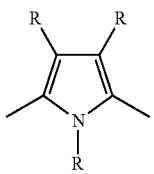 (AA-24)
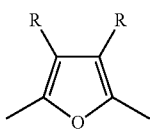 (AA-25)
[Chemical Formula 23]
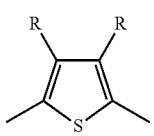 (AA-26)
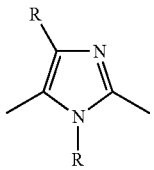 (AA-27)
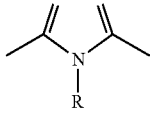 (AA-28)
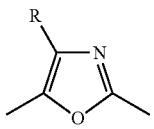 (AA-29)
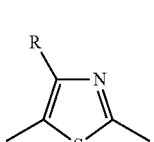 (AA-30)
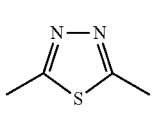 (AA-31)
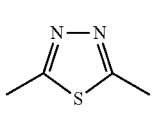 (AA-32)
[Chemical Formula 24]
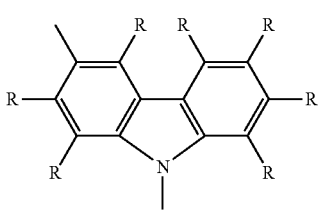 (AA-33)

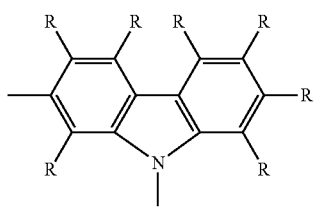
(AA-34)

[wherein, R and R$^a$ are as defined above.]

"Crosslinkable group" is a group capable of forming a new bond by being subjected to a heating treatment, an ultraviolet irradiation treatment, a radical reaction and the like, and crosslinkable groups are preferably groups represented by the formulae (B-1) to (B-17). The foregoing groups each optionally have a substituent.

[Chemical Formula 25]

(B-1)

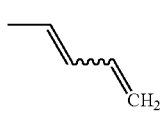
(B-2)

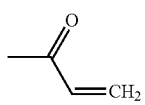
(B-3)

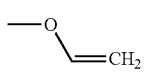
(B-4)

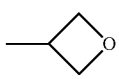
(B-5)

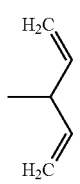
(B-6)

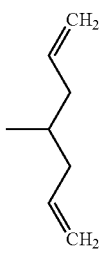
(B-7)

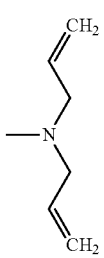
(B-8)

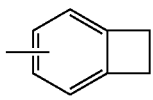
(B-9)

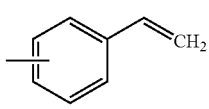
(B-10)

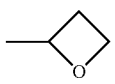
(B-11)

(B-12)

 (B-13)

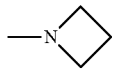 (B-14)

 (B-15)

—N₃ (B-16)

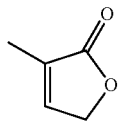 (B-17)

"Substituent" represents a halogen atom, a cyano group, an alkyl group, a cycloalkyl group, an aryl group, a monovalent heterocyclic group, an alkoxy group, a cycloalkoxy group, an aryloxy group, an amino group, a substituted amino group, an alkenyl group, a cycloalkenyl group, an alkynyl group or a cycloalkynyl group. The substituent may be a crosslinkable group.

<Polymer Compound>

The polymer compound of the present invention is a polymer compound comprising a constitutional unit represented by the formula (1) and a constitutional unit represented by the formula (Y).

[Constitutional Unit Represented by the Formula (1)]

[Chemical Formula 26]

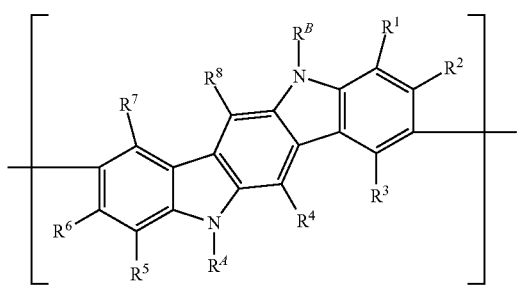

(1)

$R^1$ to $R^8$ represent preferably a hydrogen atom, an alkyl group, a cycloalkyl group or an aryl group, more preferably a hydrogen atom, an alkyl group or a cycloalkyl group, further preferably a hydrogen atom, the foregoing groups each optionally having a substituent, because a light emitting device using the polymer compound of the present invention is more excellent in light emission efficiency.

The group represented by $R^1$ to $R^8$ each optionally has a substituent. The substituent is preferably an alkyl group, a cycloalkyl group or an aryl group.

$R^A$ and $R^B$ represent preferably an aryl group, and this aryl group optionally has a substituent, because the polymer compound of the present invention is excellent in stability.

The aryl group represented by $R^A$ and $R^B$ is preferably a phenyl group optionally having a substituent, more preferably a phenyl group substituted by an alkyl group or a cycloalkyl group, further preferably a phenyl group substituted by an alkyl group, because a light emitting device using the polymer compound of the present invention is more excellent in light emission efficiency.

The group represented by $R^A$ and $R^B$ each optionally has a substituent. The substituent is preferably an alkyl group, a cycloalkyl group or an aryl group.

The constitutional unit represented by the formula (1) is preferably a constitutional unit represented by the formula (1-1), because a light emitting device using the polymer compound of the present invention is more excellent in light emission efficiency.

[Chemical Formula 27]

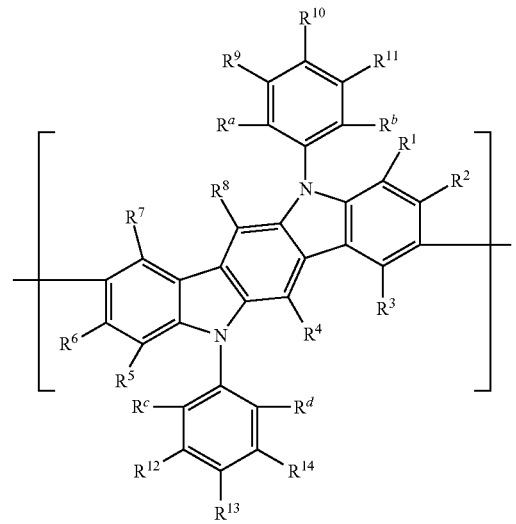

(1-1)

$R^9$ to $R^{14}$ represent preferably a hydrogen atom, an alkyl group, a cycloalkyl group or an aryl group, more preferably a hydrogen atom, an alkyl group or a cycloalkyl group, further preferably a hydrogen atom, the foregoing groups each optionally having a substituent, because a light emitting device using the polymer compound of the present invention is more excellent in light emission efficiency.

The group represented by $R^9$ to $R^{14}$ optionally has a substituent. The substituent is preferably an alkyl group, a cycloalkyl group or an aryl group.

$R^a$, $R^b$, $R^c$ and $R^d$ represent preferably a hydrogen atom, an alkyl group, a cycloalkyl group or an aryl group, more preferably a hydrogen atom, an alkyl group or a cycloalkyl group, further preferably an alkyl group or a cycloalkyl group, particularly preferably an alkyl group, the foregoing groups each optionally having a substituent, because the polymer compound of the present invention is excellent in stability.

The group represented by $R^a$, $R^b$, $R^c$ and $R^d$ optionally has a substituent. The substituent is preferably an alkyl group, a cycloalkyl group or an aryl group.

The total amount of constitutional units represented by the formula (1) is preferably 0.1 to 50 mol %, more preferably 1 to 30 mol %, further preferably 2 to 15 mol % with respect to the total content of constitutional units contained in the polymer compound, because the polymer compound of the present invention is excellent in stability.

The constitutional unit represented by the formula (1) includes, for example, constitutional units represented by the formula (1-a) to the formula (1-z) and the formula (1-aa) to the formula (1-cc), preferably constitutional units represented by the formula (1-a) to the formula (1-q), more preferably constitutional units represented by the formula (1-a) to the formula (1-k), further preferably constitutional units represented by the formula (1-a) to the formula (1-i).

[Chemical Formula 28]

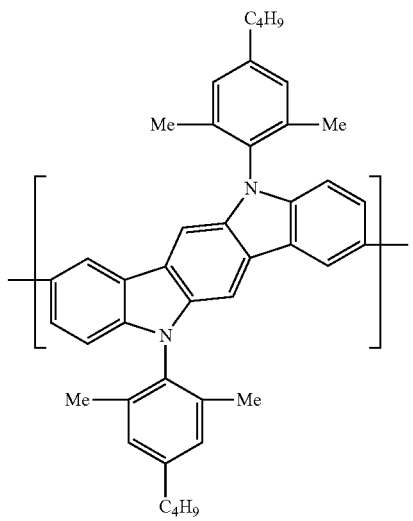

(1-a)

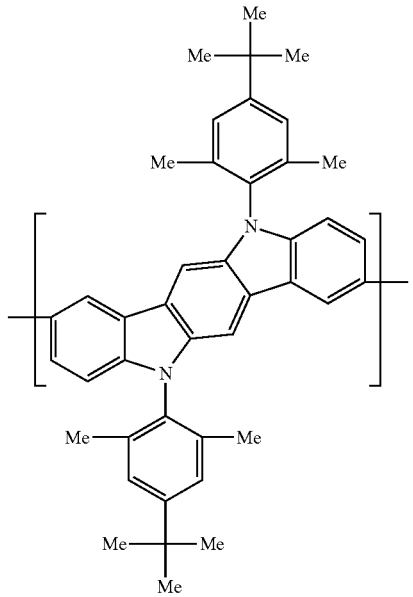

(1-b)

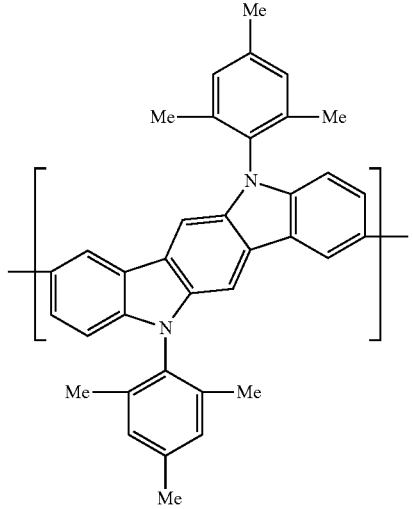

(1-c)

(1-d)
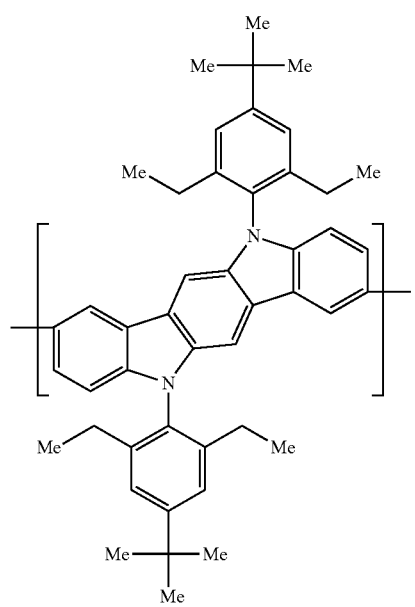
(1-e)
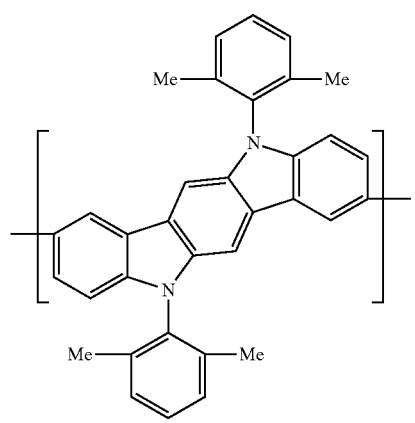
(1-f)
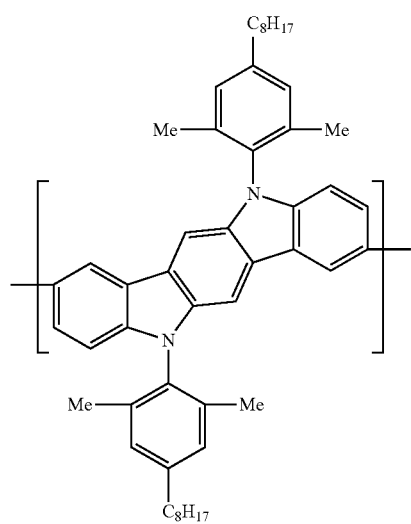
(1-g)
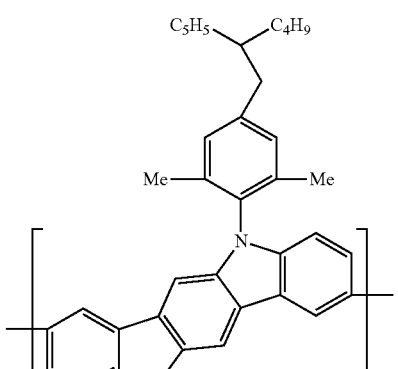
(1-h)
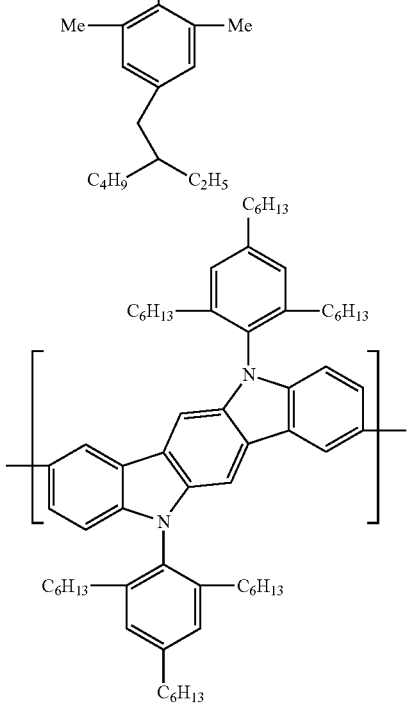
(1-i)
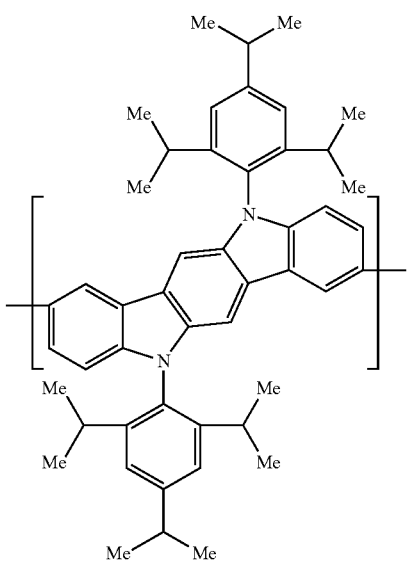

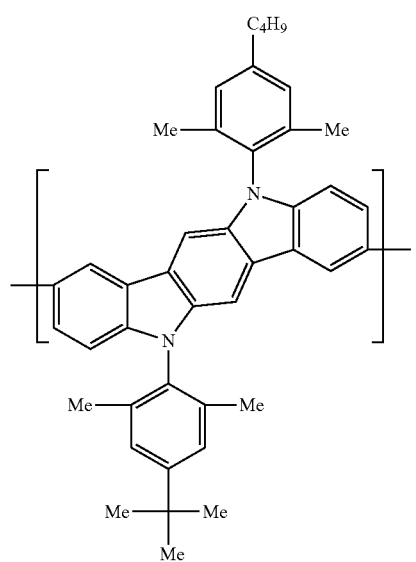
(1-j)
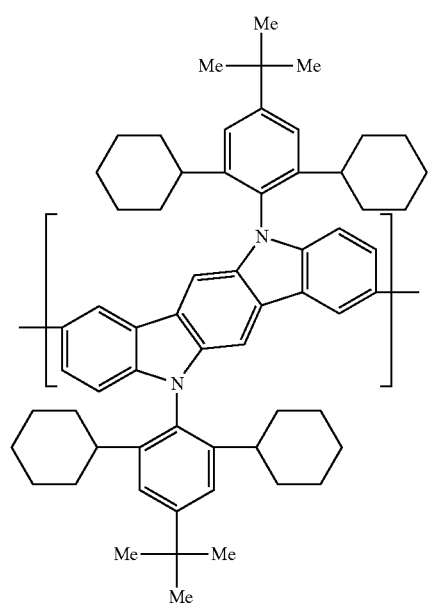
(1-k)
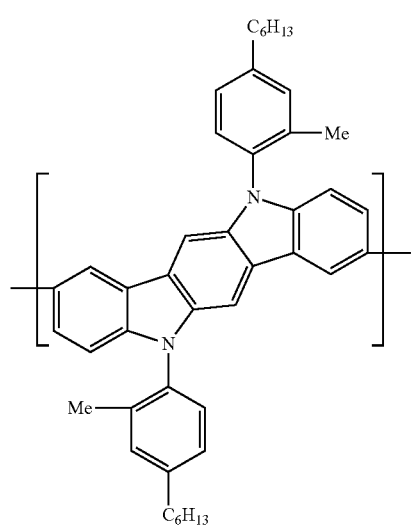
(1-l)
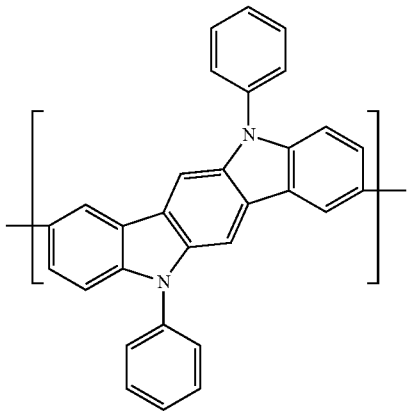
(1-m)
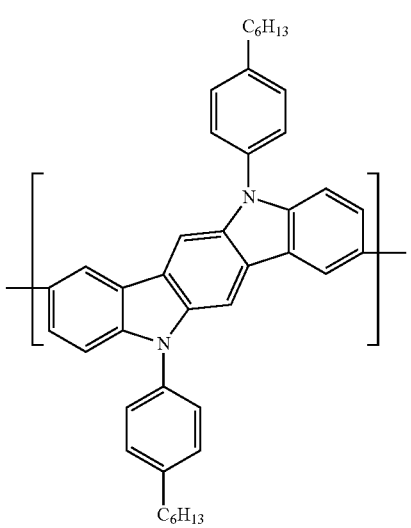
(1-n)
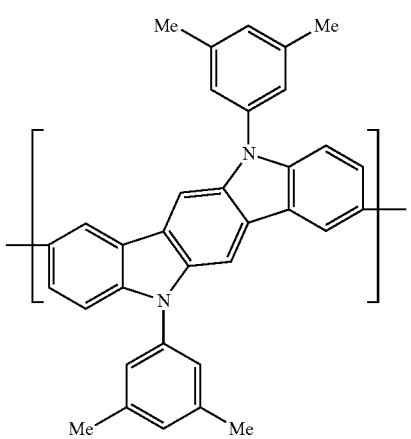
(1-o)

-continued
[Chemical Formula 29]
(1-p)
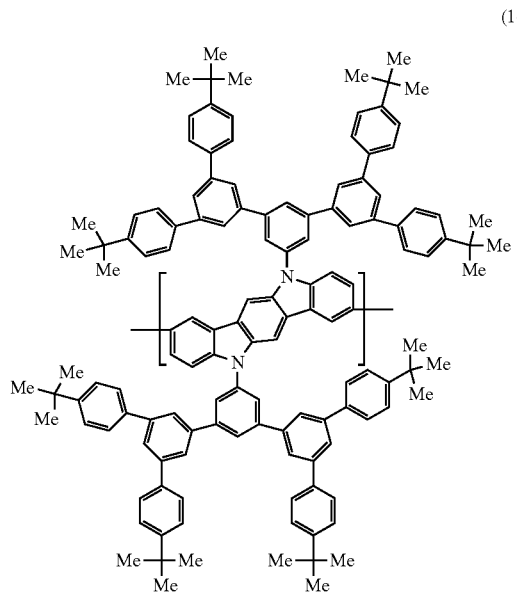
[Chemical Formula 30]
(1-r)
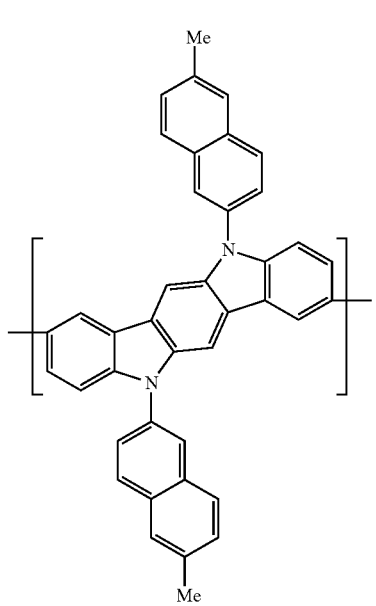
(1-q)
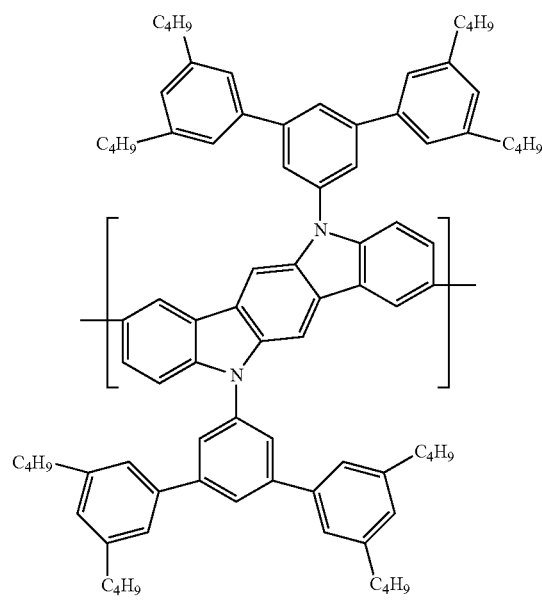
(1-s)
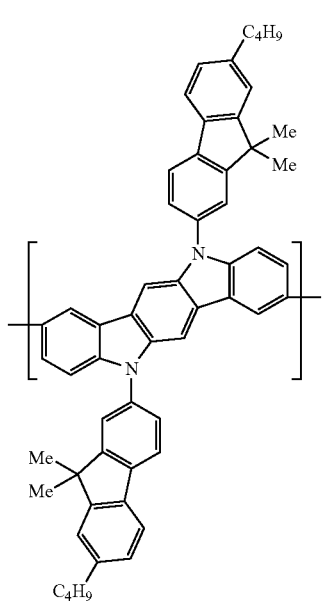

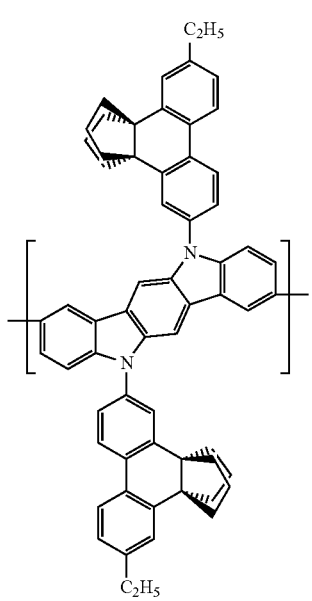
(1-t)
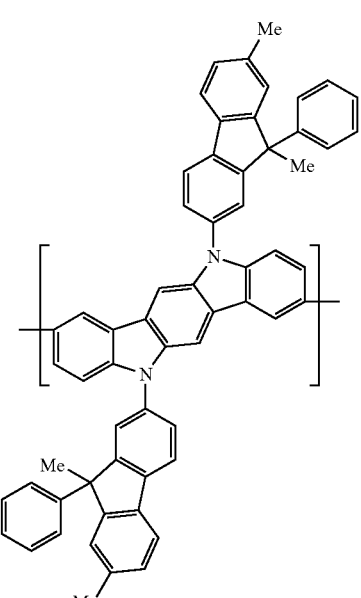
(1-v)
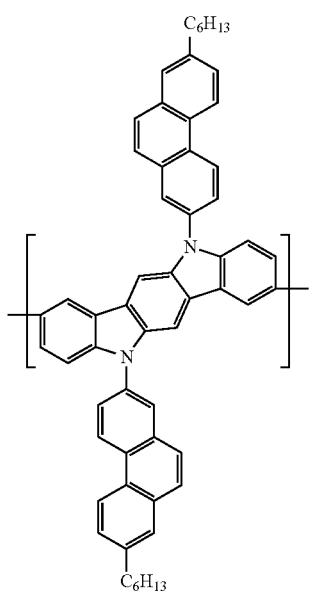
(1-u)
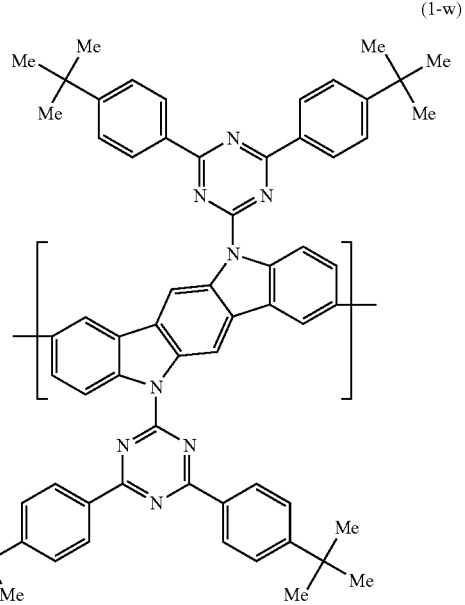
(1-w)

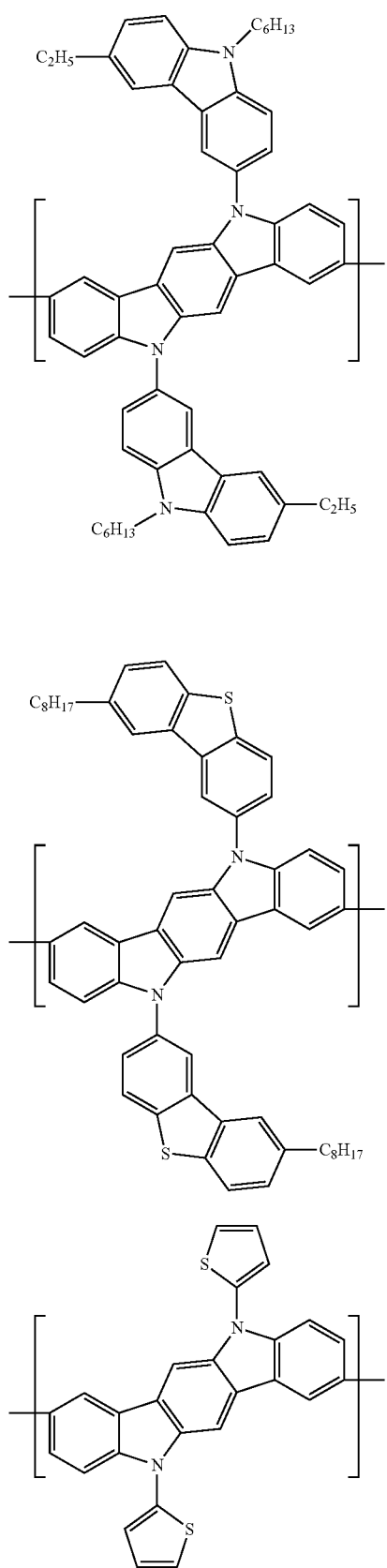
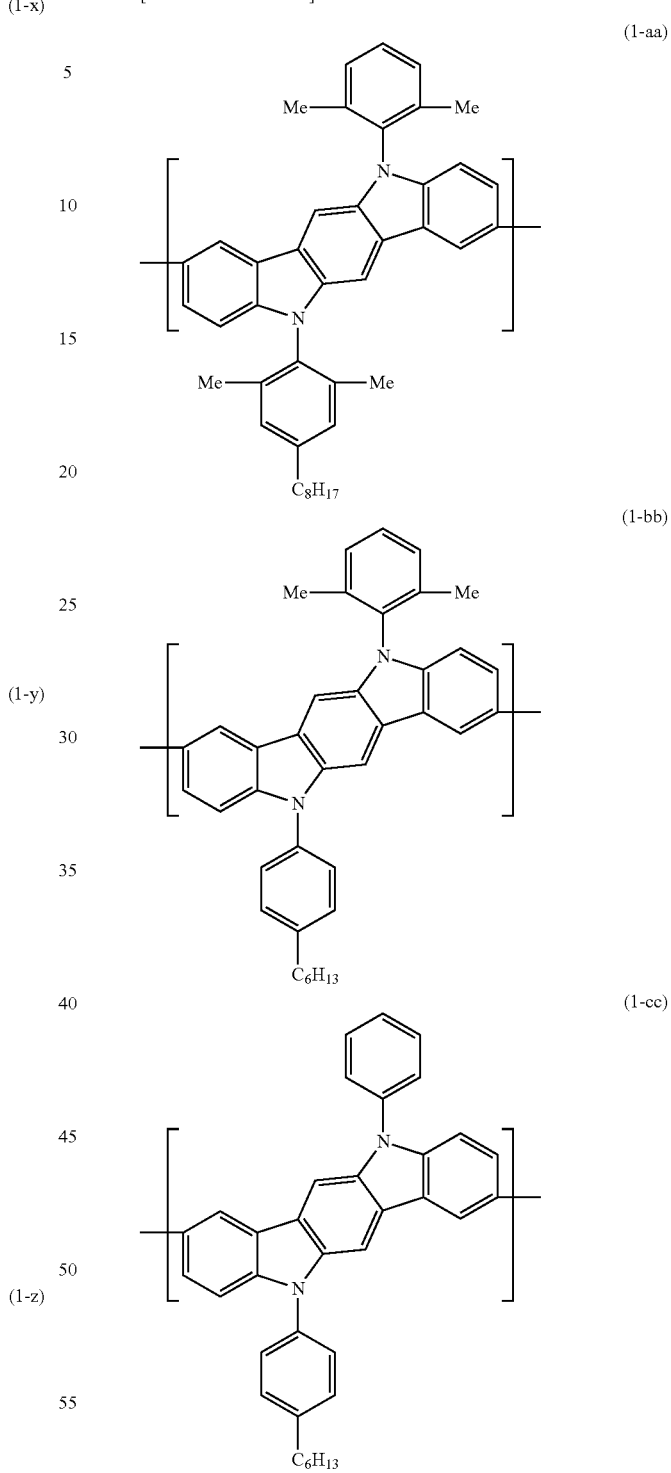

The constitutional units represented by the formula (1) may be contained each singly or two or more of them may be contained in the polymer compound.

[Constitutional Unit Represented by the Formula (Y)]
[Chemical Formula 32]

$$-\!\!\!\!+\!\!Ar^{Y1}\!\!+\!\!\!\!-$$ (Y)

The arylene group represented by $Ar^{Y1}$ is more preferably a group represented by the formula (A-1), the formula (A-6), the formula (A-7), the formula (A-9) to (A-11), the formula (A-13) or the formula (A-19), further preferably a group represented by the formula (A-1), the formula (A-7), the formula (A-9) or the formula (A-19), the foregoing groups each optionally having a substituent.

The divalent heterocyclic group represented by $Ar^{Y1}$ is more preferably a group represented by the formula (AA-4), the formula (AA-10), the formula (AA-13), the formula (AA-15), the formula (AA-18) or the formula (AA-20), further preferably a group represented by the formula (AA-4), the formula (AA-10), the formula (AA-18) or the formula (AA-20), the foregoing groups each optionally having a substituent.

The more preferable range, the further preferable range and the particularly preferable range of the arylene group and the divalent heterocyclic group in the divalent group in which at least one arylene group and at least one divalent heterocyclic group are bonded directly to each other represented by $Ar^{Y1}$ are the same as the more preferable range, the further preferable range and the particularly preferable range of the arylene group and the divalent heterocyclic group represented by $Ar^{Y1}$ described above, respectively.

The divalent group in which at least one arylene group and at least one divalent heterocyclic group are bonded directly to each other represented by $Ar^{Y1}$ includes, for example, groups represented by the following formulae, the foregoing groups each optically having substituent.

[Chemical Formula 33]

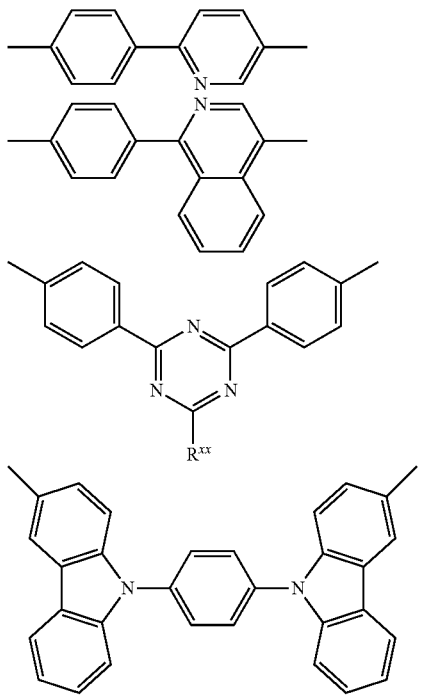

[wherein, $R^{XX}$ represents a hydrogen atom, an alkyl group, a cycloalkyl group, an aryl group or a monovalent heterocyclic group, the foregoing groups each optionally having a substituent.]

$R^{XX}$ is preferably an alkyl group, a cycloalkyl group or an aryl group, the foregoing groups each optionally having a substituent.

The substituent which the group represented by $Ar^{Y1}$ optionally has is preferably an alkyl group, a cycloalkyl group or an aryl group, the foregoing groups each optionally further having a substituent.

The constitutional unit represented by the formula (Y) includes, for example, constitutional units represented by the formulae (Y-1) to (Y-7), and from the standpoint of the luminance life of a light emitting device produced by using the polymer compound of the present invention preferable is a constitutional unit represented by the formula (Y-1) or (Y-2), from the standpoint of electron transportability preferable is a constitutional unit represented by the formula (Y-3) or (Y-4), and from the standpoint of hole transportability preferable are constitutional units represented by the formulae (Y-5) to (Y-7). Also, from the standpoint of light emittion efficiency of a light emitting device produced by using the polymer compound of the present invention preferable is a constitutional unit represented by the formula (Y-2) and the formula (Y-5) to (Y-7) and more preferable is a constitutional unit represented by the formula (Y-2).

[Chemical Formula 34]

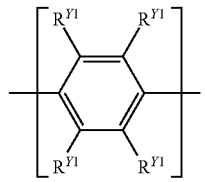

(Y-1)

[wherein, each $R^{Y1}$ represents a hydrogen atom, an alkyl group, a cycloalkyl gro6up, an alkoxy group, a cycloalkoxy group, an aryl group or a monovalent heterocyclic group, the foregoing groups each optionally having a substituent. The plurality of $R^{Y1}$ may be the same or different, with the proviso that adjacent groups $R^{Y1}$ may be combined together to form a ring together with the carbon atoms to which they are attached.]

Each $R^{Y1}$ is preferably a hydrogen atom, an alkyl group or a cycloalkyl group, these groups each optionally having a substituent.

[Chemical Formula 35]

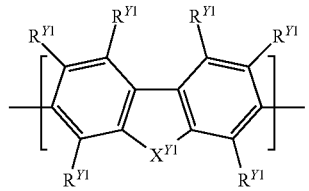

(Y-2)

$R^{Y2}$ in the group represented by —$C(R^{Y2})_2$—, the group represented by —$C(R^{Y2})=C(R^{Y2})$— and the group represented by —$C(R^{Y2})_2$—$C(R^{Y2})$— represented by $X^{Y1}$ is preferably an alkyl group, a cycloalkyl group, an aryl group or a monovalent heterocyclic group, more preferably an alkyl group a cycloalkyl group or an aryl group, the foregoing groups each optionally having a substituent.

Regarding the combination of two $R^{Y2}$s in the group represented by —$C(R^{Y2})_2$— in $X^{Y1}$, it is preferable that the both are an alkyl group or a cycloalkyl group, the both are an aryl group, the both are a monovalent heterocyclic group, or one is an alkyl group or a cycloalkyl group and the other is an aryl group or a monovalent heterocyclic group, it is more preferable that one is an alkyl group or cycloalkyl group and the other is an aryl group, the foregoing groups each optionally having a substituent. The two groups $R^{Y2}$ may be combined together to form a ring together with the atoms to which they are attached, and when the groups $R^{Y2}$ form a ring, the group represented by —C($R^{Y2}$)$_2$— is preferably a group represented by the formula (Y-A1) to (Y-A5), more preferably a group represented by the formula (Y-A4), the foregoing groups each optionally having a substituent.

[Chemical Formula 36]

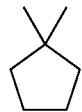

(Y-A1)

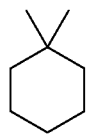

(Y-A2)

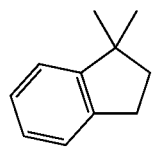

(Y-A3)

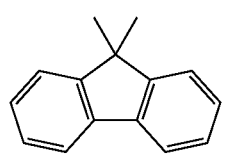

(Y-A4)

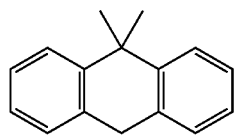

(Y-A5)

Regarding the combination of two $R^{Y2}$s in the group represented by —C($R^{Y2}$)=C($R^{Y2}$)— in $X^{Y1}$, it is preferable that the both are an alkyl group or cycloalkyl group, or one is an alkyl group or a cycloalkyl group and the other is an aryl group, the foregoing groups each optionally having a substituent.

Four $R^{Y2}$s in the group represented by —C($R^{Y2}$)$_2$—C($R^{Y2}$)$_2$— in $X^{Y1}$ are preferably an alkyl group or a cycloalkyl group optionally having a substituent. The plurality of $R^{Y2}$ may be combined together to form a ring together with the carbon atoms to which they are attached, and when the groups $R^{Y2}$ form a ring, the group represented by —C($R^{Y2}$)$_2$—C($R^{Y}$)$_2$— is preferably a group represented by the formula (Y-B1) to (Y-B5), more preferably a group represented by the formula (Y-B3), the foregoing groups each optionally having a substituent.

[Chemical Formula 37]

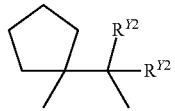

(Y-B1)

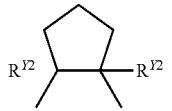

(Y-B2)

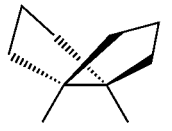

(Y-B3)

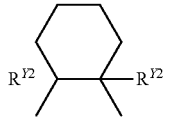

(Y-B4)

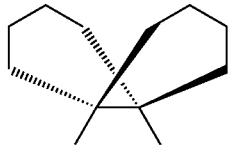

(Y-B5)

[wherein, each $R^{Y2}$ represents the same meaning as described above.]

[Chemical Formula 38]

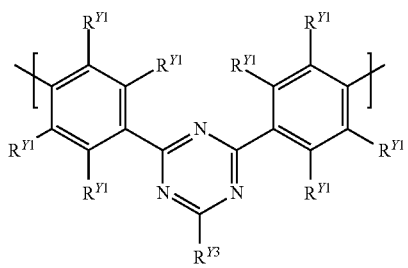

(Y-3)

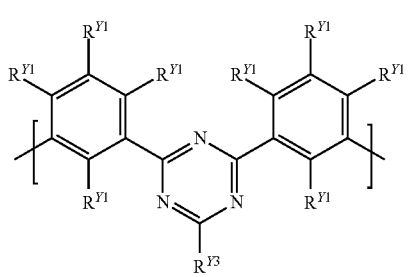

(Y-4)

[wherein, each $R^{Y1}$ represents the same meaning as described above. $R^{Y3}$ represents a hydrogen atom, an alkyl group, a cycloalkyl group, an alkoxy group, a cycloalkoxy group, an aryl group or a monovalent heterocyclic group, the foregoing groups each optionally having a substituent.]

$R^{Y3}$ is preferably an alkyl group, a cycloalkyl group, an alkoxy group, a cycloalkoxy group, an aryl group or a monovalent heterocyclic group, more preferably an aryl group, the foregoing groups each optionally having a substituent.

[Chemical Formula 39]

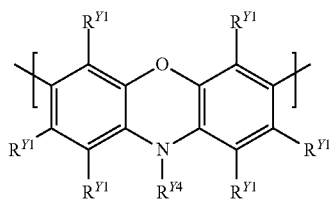
(Y-5)

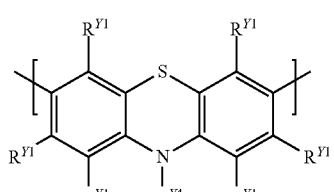
(Y-6)

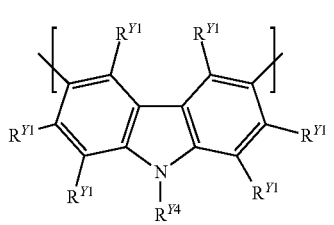
(Y-7)

$R^{Y4}$ is preferably an alkyl group, a cycloalkyl group, an alkoxy group, a cycloalkoxy group, an aryl group or a monovalent heterocyclic group, more preferably an aryl group, the foregoing groups each optionally having a substituent.

The constitutional unit represented by the formula (Y) includes, for example, constitutional units represented by the formulae (Y-11) to (Y-55).

[Chemical Formula 40]

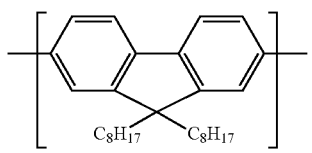
(Y-11)

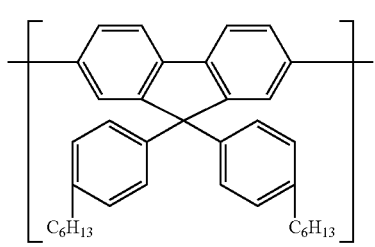
(Y-12)

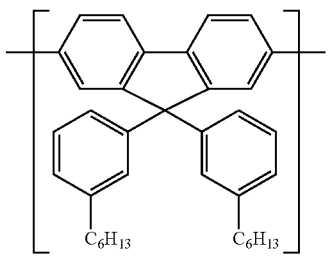
(Y-13)

[Chemical Formula 41]

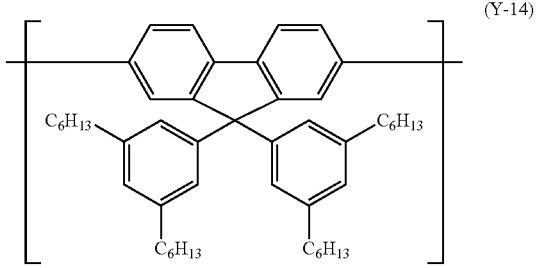
(Y-14)

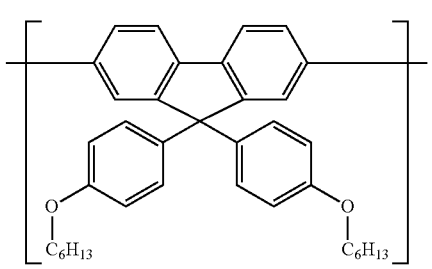
(Y-15)

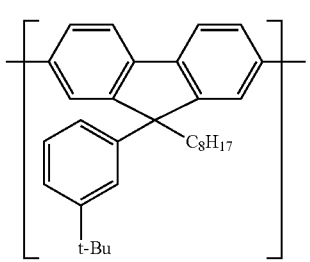
(Y-16)

[Chemical Formula 42]

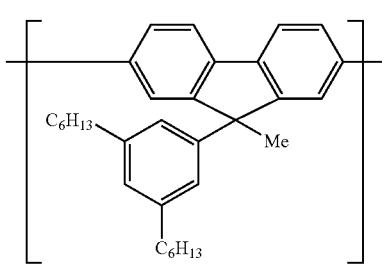
(Y-17)

(Y-18) 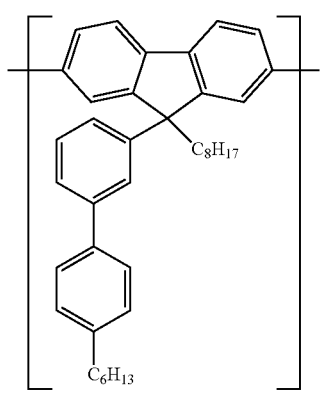
(Y-19) 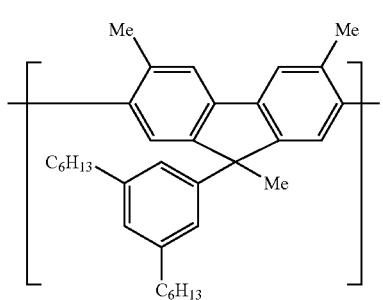
[Chemical Formula 43]
(Y-20) 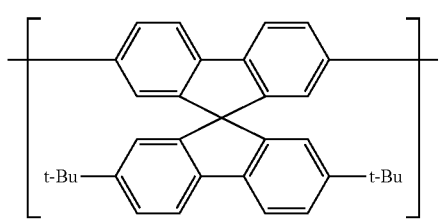
(Y-21) 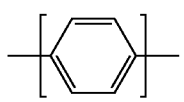
(Y-22) 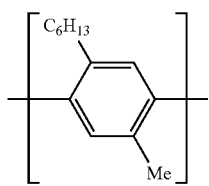
(Y-23) 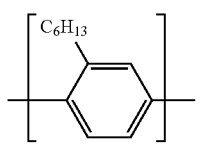
[Chemical Formula 44]
(Y-24) 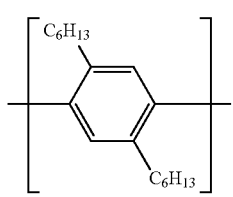
(Y-25) 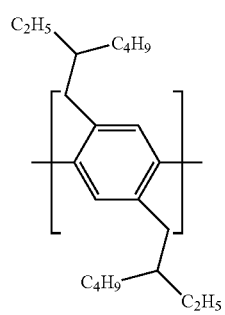
(Y-26) 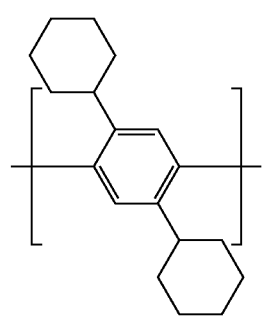
(Y-27) 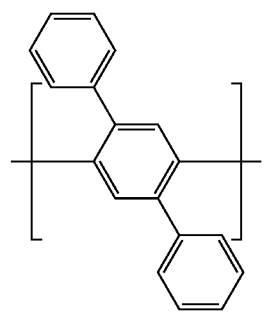
[Chemical Formula 45]
(Y-28) 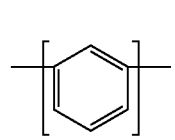
(Y-29) 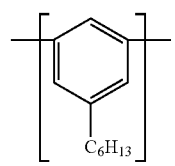
(Y-30) 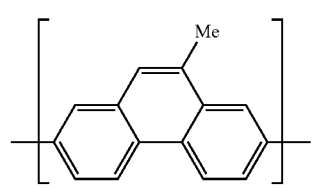
(Y-31) 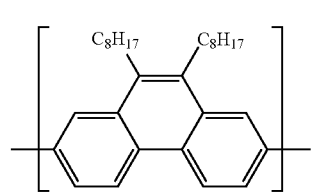

[Chemical Formula 46]
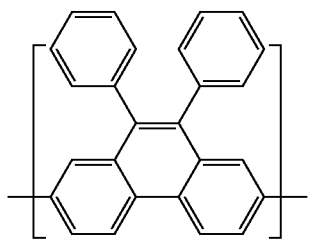
(Y-32)
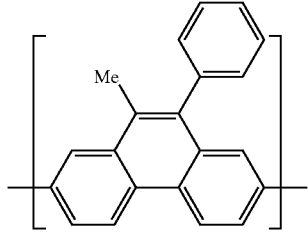
(Y-33)
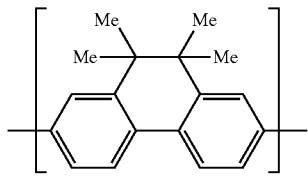
(Y-34)
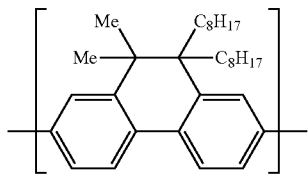
(Y-35)
[Chemical Formula 47]
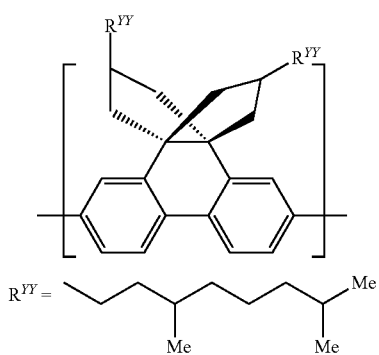
(Y-36)
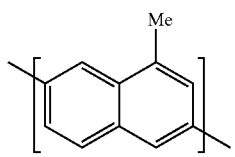
(Y-37)
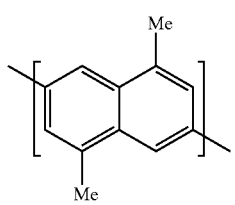
(Y-38)
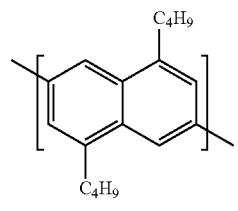
(Y-39)
[Chemical Formula 48]
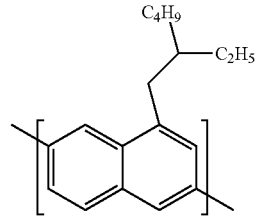
(Y-40)
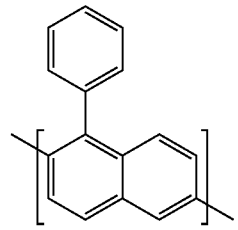
(Y-41)
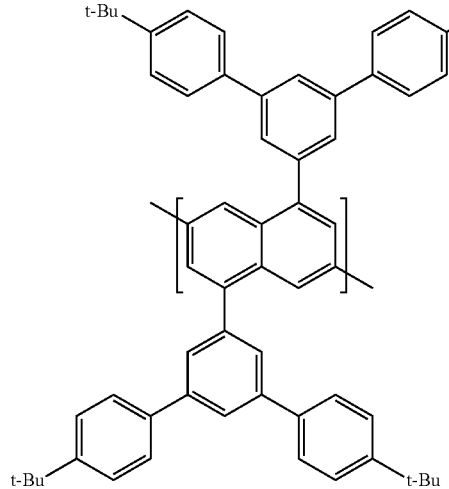
(Y-42)
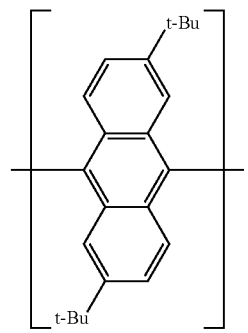
(Y-43)

(Y-44) 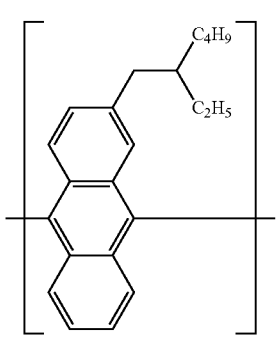
[Chemical Formula 49]
(Y-45) 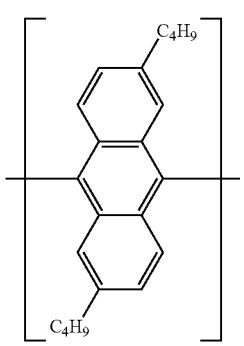
(Y-46) 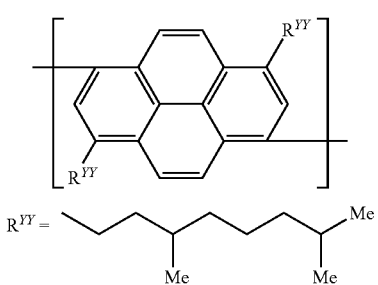
(Y-47) 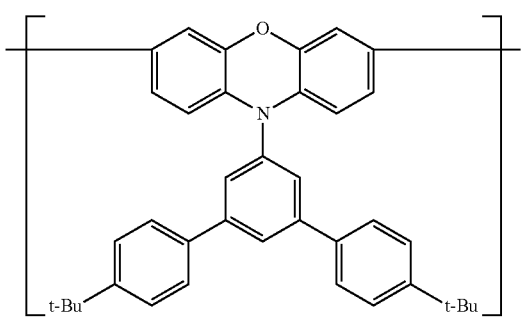
[Chemical Formula 50]
(Y-48) 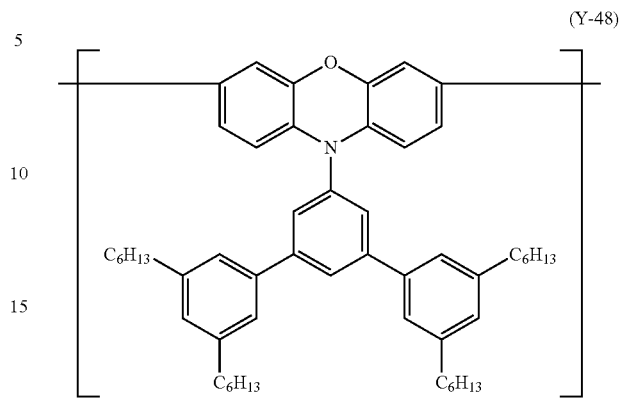
(Y-49) 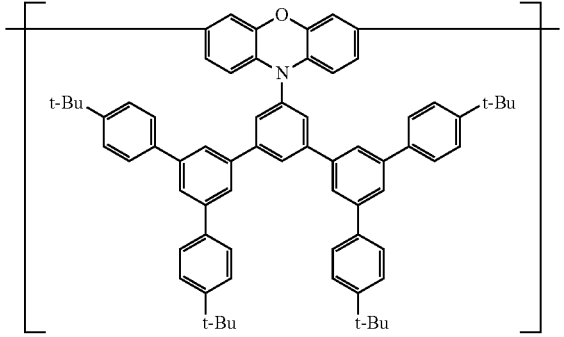
[Chemical Formula 51]
(Y-50) 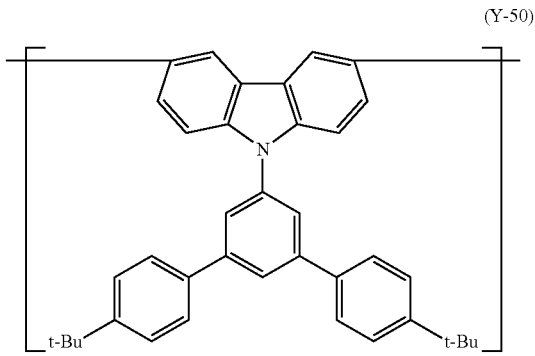
(Y-51) 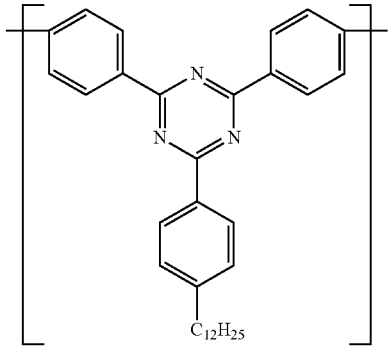

(Y-52)

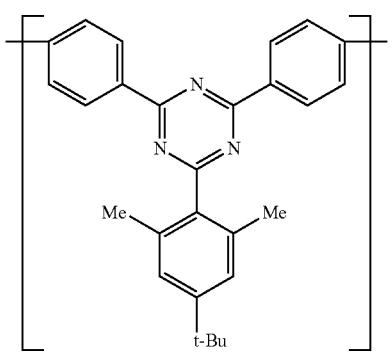

[Chemical Formula 52]

(Y-53)

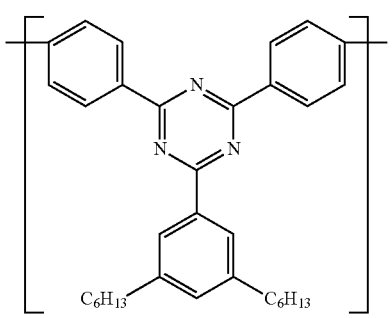

(Y-54)

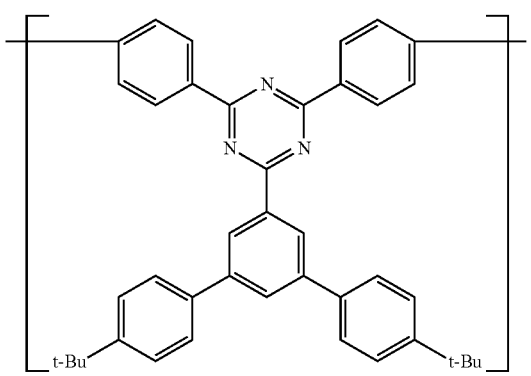

(Y-55)

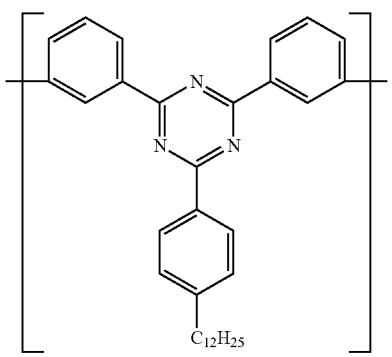

The content of the constitutional unit represented by the formula (Y) in which $Ar^{Y1}$ is an arylene group is preferably 0.5 to 80 mol %, more preferably 30 to 60 mol % with respect to the total content of constitutional units contained in the polymer compound, because the light emission efficiency of a light emitting device produced by using the polymer compound of the present invention is excellent.

The content of the constitutional unit represented by the formula (Y) in which $Ar^{Y1}$ is a divalent heterocyclic group or a divalent group in which at least one arylene group and at least one divalent heterocyclic group are bonded directly to each other is preferably 0.5 to 30 mol %, more preferably 3 to 30 mol % with respect to the total content of constitutional units contained in the polymer compound, because the charge transportability of a light emitting device produced by using the polymer compound of the present invention is excellent.

The constitutional unit represented by the formula (Y) may be contained only singly or two or more of the constitutional units may be contained in the polymer compound.

[Other Constitutional Unit]

The polymer compound of the present invention may further comprise a constitutional unit represented by the formula (X), because hole transportability is excellent.

[Chemical Formula 53]

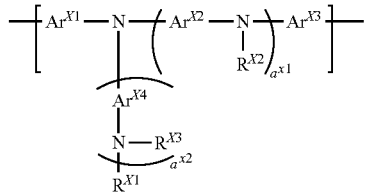

(X)

$a^{X1}$ is preferably an integer of 2 or less, more preferably 1, because the luminance life of a light emitting device produced by using the polymer compound of the present invention is excellent.

$a^{X2}$ is preferably an integer of 2 or less, more preferably 0, because the luminance life of a light emitting device produced by using the polymer compound of the present invention is excellent.

$R^{X1}$, $R^{X2}$ and $R^{X3}$ are preferably an alkyl group, a cycloalkyl group, an aryl group or a monovalent heterocyclic group, more preferably an aryl group, the foregoing groups each optionally having a substituent.

The arylene group represented by $Ar^{X1}$ and $Ar^{X3}$ is more preferably a group represented by the formula (A-1) or the formula (A-9), further preferably a group represented by the formula (A-1), the foregoing groups each optionally having a substituent.

The divalent heterocyclic group represented by $Ar^{X1}$ and $Ar^{X3}$ is more preferably a group represented by the formula (AA-1), the formula (AA-2) or the formula (AA-7) to (AA-26), the foregoing groups each optionally having a substituent.

$Ar^{X1}$ and $Ar^{X3}$ are preferably an arylene group optionally having a substituent.

The arylene group represented by $Ar^{X2}$ and $Ar^{X4}$ is more preferably a group represented by the formula (A-1), the formula (A-6), the formula (A-7), the formulae (A-9) to (A-11) or the formula (A-19), the foregoing groups each optionally having a substituent.

The more preferable range of the divalent heterocyclic group represented by $Ar^{X2}$ and $Ar^{X4}$ is the same as the more preferable range of the divalent heterocyclic group represented by $Ar^{X1}$ and $Ar^{X3}$ The more preferable range and the further preferable range of the arylene group and the divalent heterocyclic group in the divalent group in which at least one arylene group and at least one divalent heterocyclic group are bonded directly to each other represented by $Ar^{X2}$ and $Ar^{X4}$ are the same as the more preferable range and the further preferable range of the arylene group and the divalent heterocyclic group represented by $Ar^{X1}$ and $Ar^{X3}$, respectively.

The divalent group in which at least one arylene group and at least one divalent heterocyclic group are bonded directly to each other represented by $Ar^{X2}$ and $Ar^{X4}$ includes the same as the divalent group in which at least one arylene group and at least one divalent heterocyclic group are bonded directly to each other represented by $Ar^{Y1}$ in the formula (Y).

$Ar^{X2}$ and $Ar^{X4}$ are preferably an arylene group optionally having a substituent.

The substituent which the group represented by $Ar^{X1}$ to $Ar^{X4}$ and $R^{X1}$ to $R^{X3}$ optionally has is preferably an alkyl group, a cycloalkyl group or an aryl group, the foregoing groups each optionally further having a substituent.

The constitutional unit represented by the formula (X) is preferably a constitutional unit represented by the formula (X-1) to (X-7), more preferably a constitutional unit represented by the formula (X-3) to (X-7), further preferably a constitutional unit represented by the formula (X-3) to (X-6).

[Chemical Formula 54]

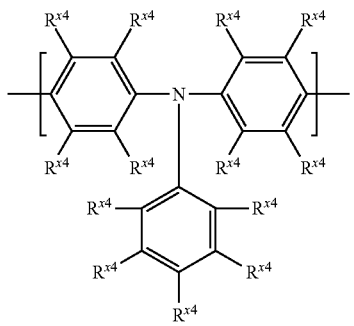

(X-1)

[Chemical Formula 55]

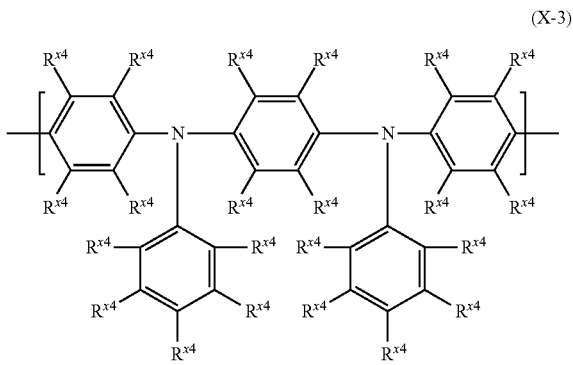

(X-3)

[Chemical Formula 56]

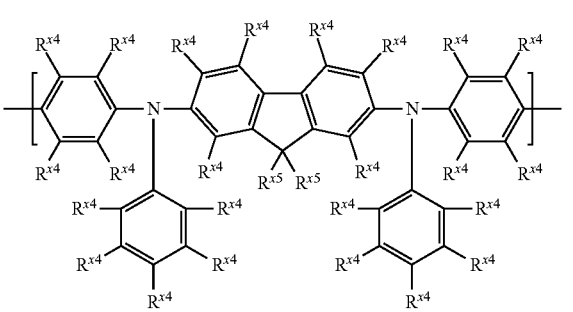

(X-4)

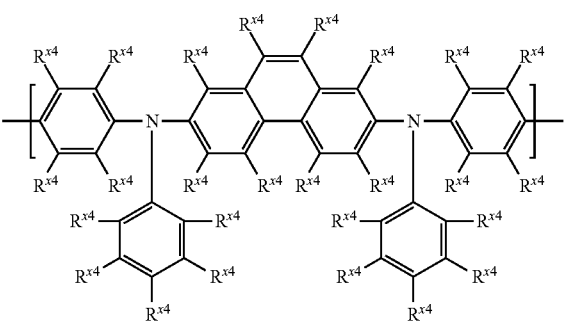

(X-5)

[Chemical Formula 57]

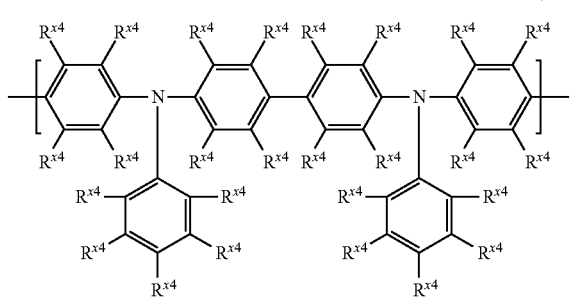

(X-2)

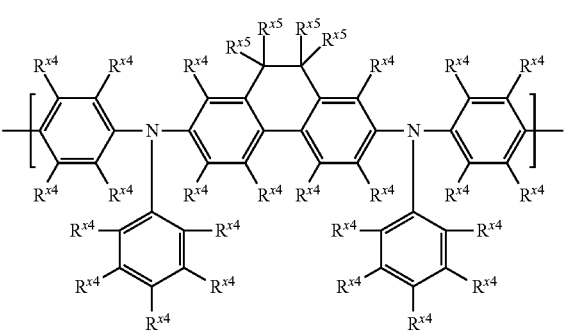

(X-6)

(X-7)

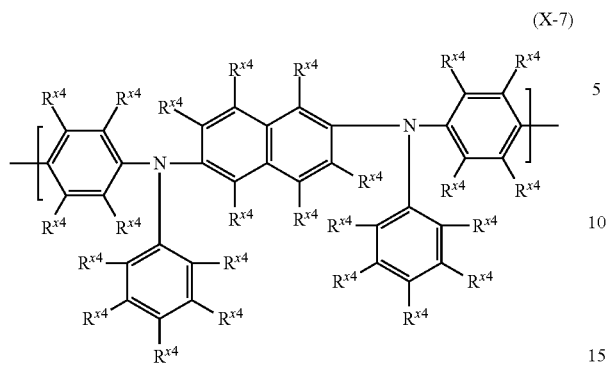

[wherein, $R^{X4}$ and $R^{X5}$ each independently represent a hydrogen atom, an alkyl group, a cycloalkyl group, an alkoxy group, a cycloalkoxy group, an aryl group, an aryloxy group, a halogen atom, a monovalent heterocyclic group or a cyano group, the foregoing groups each optionally having a substituent. The plurality of $R^{X4}$ may be the same or different. The plurality of $R^{X5}$ may be the same or different, with the proviso that adjacent groups $R^{X5}$ may be combined together to form a ring together with the carbon atoms to which they are attached.]

The content of the constitutional unit represented by the formula (X) is preferably 0.1 to 50 mol %, more preferably 1 to 30 mol %, further preferably 2 to 20 mol % with respect to the total content of constitutional units contained in the polymer compound, because hole transportability is excellent.

The constitutional unit represented by the formula ( X) includes, for example, constitutional units represented by the formulae (X1-1) to (X1-19), preferably constitutional units represented by the formulae (X1-6) to (X1-14).

[Chemical Formula 58]

(X1-1)

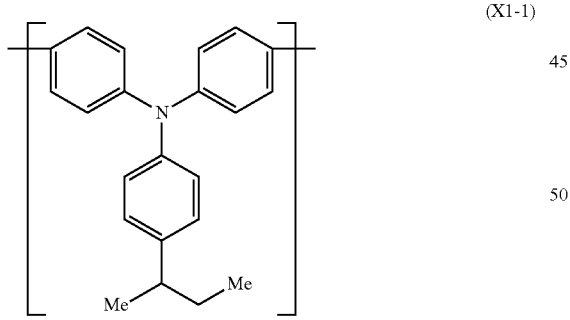

(X1-2)

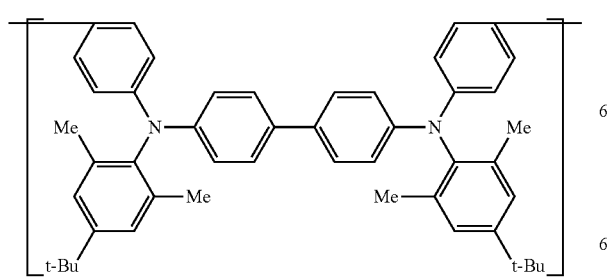

(X1-3)

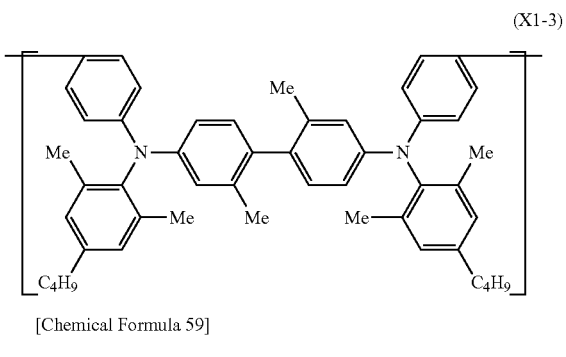

[Chemical Formula 59]

(X1-4)

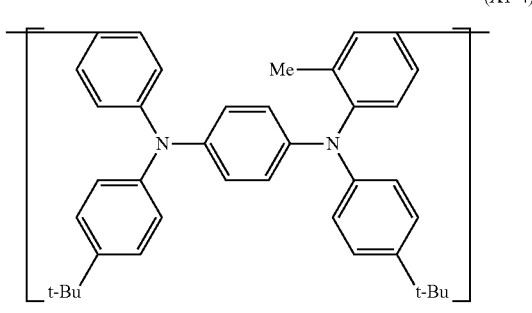

(X1-5)

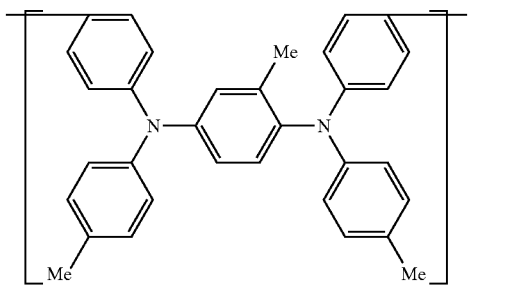

(X1-6)

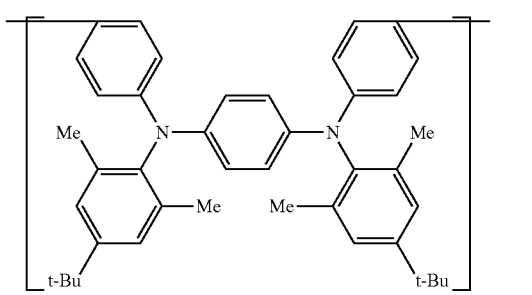

[Chemical Formula 60]

(X1-7)

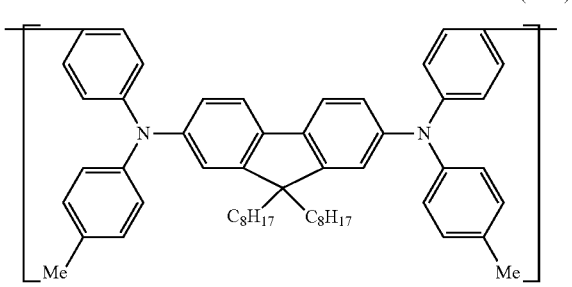

-continued
(X1-8)
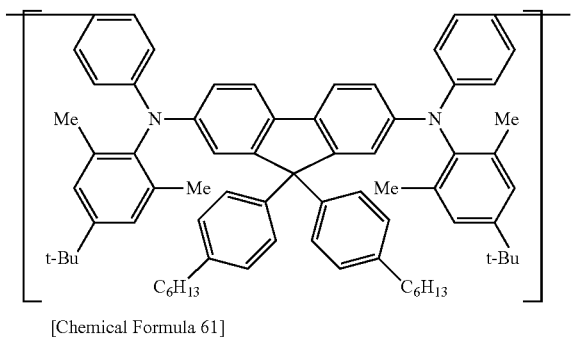
[Chemical Formula 61]
(X1-9)
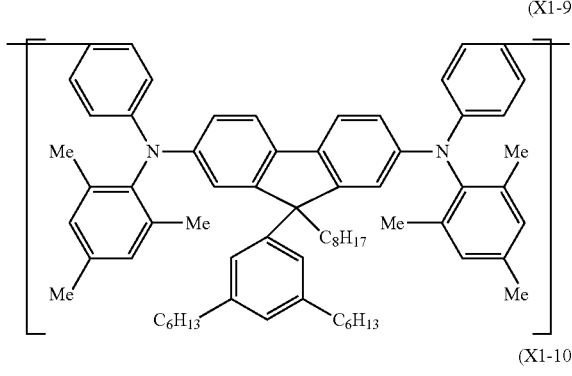
[Chemical Formula 62]
(X1-10)
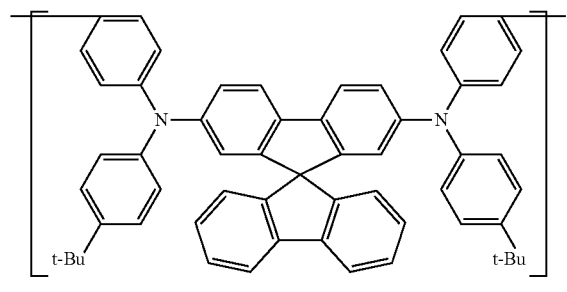
(X1-11)
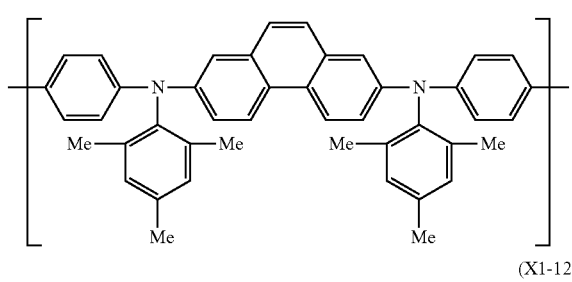
(X1-12)
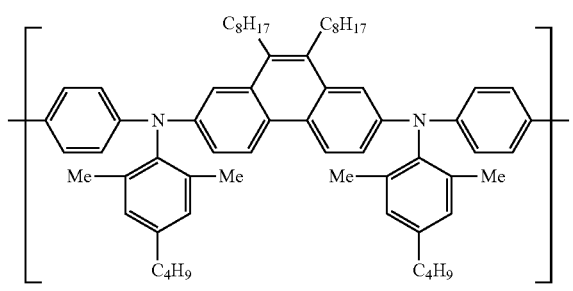
[Chemical Formula 63]
(X1-13)
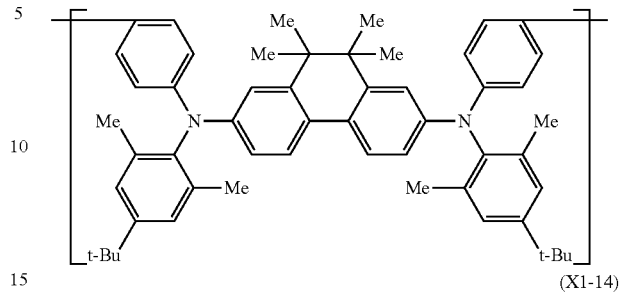
(X1-14)
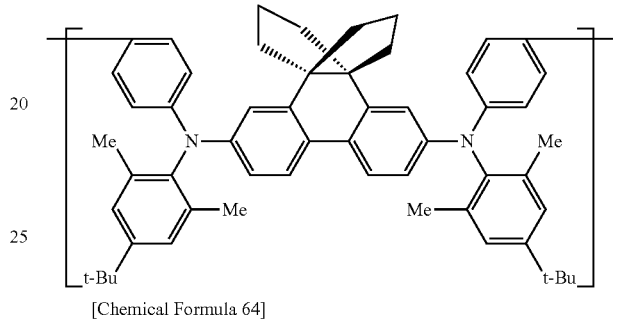
[Chemical Formula 64]
(X1-15)
(X1-16)
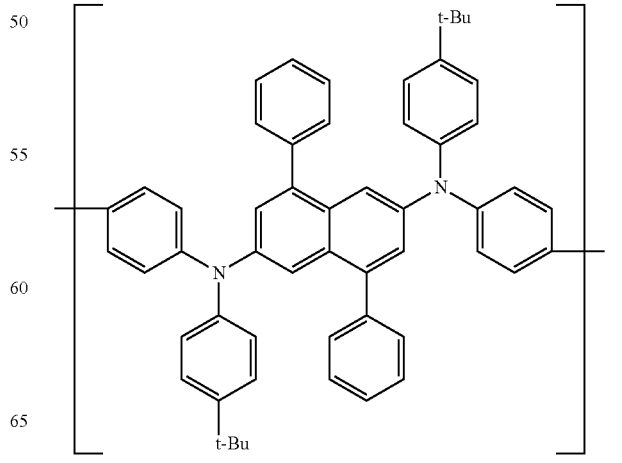

[Chemical Formula 65]

(X1-17)

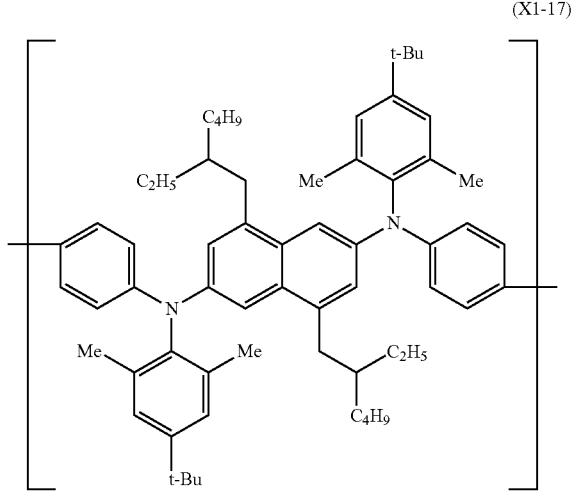

(X1-18)

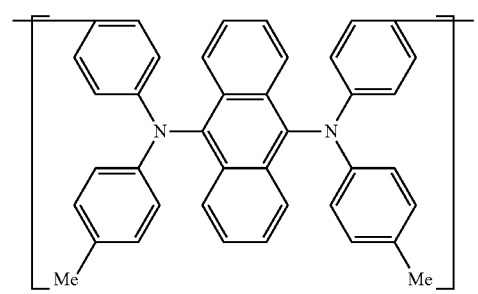

(X1-19)

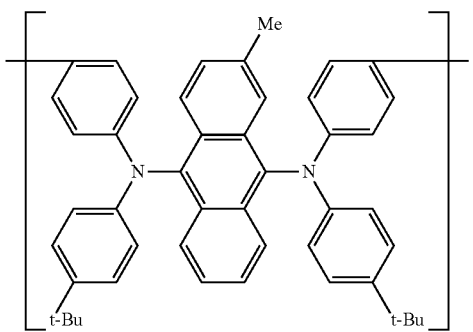

The constitutional unit represented by the formula (X) may be contained only singly or two or more units thereof may be contained in the polymer compound of the present invention.

The polymer compound of the present invention includes, for example, polymer compounds P-1 to P-8 shown in Table 1. "Other constitutional unit" denotes a constitutional unit other than constitutional units represented by the formula (1), the formula (Y-1) to the formula (Y-7) and the formula (X).

TABLE 1

| | molar ratio of constitutional unit | | | | | |
|---|---|---|---|---|---|---|
| Polymer compound | formula (1) p | formula (Y-1) to (Y-2) q | formula (Y-3) to (Y-4) r | formula (Y-5) to (Y-7) s | formula (X) t | others u |
| P-1 | 0.1 to 99.9 | 0.1 to 99.9 | 0 | 0 | 0 | 0 to 30 |
| P-2 | 0.1 to 99.8 | 0.1 to 99.8 | 0 | 0 | 0.1 to 99.8 | 0 to 30 |
| P-3 | 0.1 to 99.8 | 0 | 0.1 to 99.8 | 0 | 0.1 to 99.8 | 0 to 30 |
| P-4 | 0.1 to 99.9 | 0 | 0 | 0.1 to 99.9 | 0 | 0 to 30 |
| P-5 | 0.1 to 99.8 | 0.1 to 99.8 | 0 | 0.1 to 99.8 | 0 | 0 to 30 |
| P-6 | 0.1 to 99.7 | 0.1 to 99.7 | 0 | 0.1 to 99.7 | 0.1 to 99.7 | 0 to 30 |
| P-7 | 0.1 to 99.7 | 0.1 to 99.7 | 0.1 to 99.7 | 0.1 to 99.7 | 0 | 0 to 30 |
| P-8 | 0.1 to 99.6 | 0.1 to 99.6 | 0.1 to 99.6 | 0.1 to 99.6 | 0.1 to 99.6 | 0 to 30 |

[in the table, p, q, r, s, t and u represent the mole fraction of each constitutional unit. p + q + r + s + t + u = 100 and, 70 ≤ p + q + r + s + t + u ≤ 100.

Other constitutional unit denotes a constitutional unit other than constitutional units represented by the formula (1), the formula (Y-1) to the formula (Y-7) and the formula (X).]

The examples and preferable ranges of constitutional units represented by the formula (1), the formula (Y-1) to the formula (Y-7) and the formula (X) in polymer compounds P-1 and P-2 are as described above.

An end group of the polymer compound of the present invention is preferably a stable group, because if a polymerization active group remains intact at the end, when the polymer compound is used for fabrication of a light emitting device, the light emitting property or luminance life possibly becomes lower. This end group is preferably a group having a conjugated bond to the main chain, and includes groups bonding to an aryl group or a monovalent heterocyclic group via a carbon-carbon bond.

The polymer compound of the present invention may be any of a block copolymer, a random copolymer, an alternative copolymer and a graft copolymer, and may also be other embodiment, and a copolymer produced by copolymerizing a several raw material monomers is preferable.

<Production Method of Polymer Compound>

Next, the production method of the polymer compound of the present invention will be illustrated.

The polymer compound of the present invention can be produced, for example, by condensation-polymerizing a compound represented by the formula (M-1), a compound represented by the formula (M-2) and other compounds (for example, a compound represented by the formula (M-3) and/or the formula (M-4)). In the present specification, compounds used for production of the polymer compound of the present invention are collectively called "raw material monomer" in some cases.

[Chemical Formula 66]

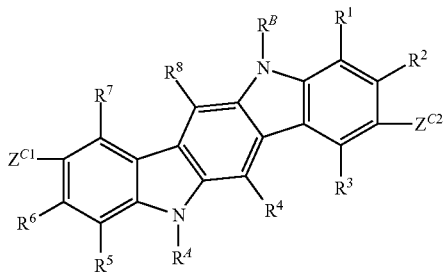

(M-1)

[Chemical Formula 67]

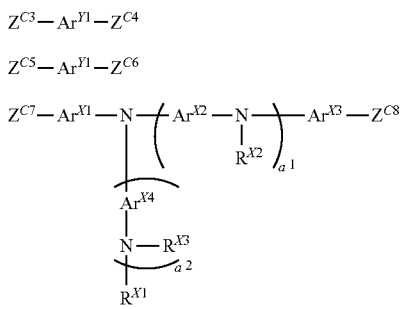

(M-2)
(M-3)
(M-4)

[wherein,
$R^1$ to $R^3$, $R^A$, $R^B$, $Ar^{Y1}$, $a^1$, $a^2$, $Ar^{X1}$ to $Ar^{X4}$ and $R^{X1}$ to $R^{X3}$ are as defined above.

$Z^{c1}$ to $Z^{c1}$ each independently represent a group selected from the group consisting of Group A of substituent s and Group B of substituents.].

For example, when $Z^{c1}$, $Z^{c2}$ and $Z^{c5}$ to $Z^{c8}$ are a group selected from Group A of substituents, $Z^{c3}$ and $Z^{c4}$ are selected from Group B of substituents.

For example, when $Z^{c1}$, $Z^{c2}$ and $Z^{c5}$ to $Z^{c8}$ are a group selected from Group B of substituents, $Z^{c3}$ and $Z^{c4}$ are selected from Group A of substituents.

<Group A of Substituents>

A hydrogen atom, a chlorine atom, a bromine atom, an iodine atom and a group represented by —O—S(=O)$_2$R$^{C1}$ (wherein, R$^{C1}$ represents an alkyl group, a cycloalkyl group or an aryl group, the foregoing groups each optionally having a substituent.).

<Group B of Substituents>

A group represented by —B(OR$^{C2}$)$_2$ (wherein, each R$^{C2}$ represents a hydrogen atom, an alkyl group, a cycloalkyl group or an aryl group, the foregoing groups each optionally having a substituent. The plurality of R$^{C2}$ may be the same or different and may be combined together to form a cyclic structure together with the oxygen atoms to which they are attached.);

a group represented by —BF$_3$Q' (wherein, Q' represents Li, Na, K, Rb or Cs.);

a group represented by —MgY' (wherein, Y' represents a chlorine atom, a bromine atom or an iodine atom.);

a group represented by —ZnY'' (wherein, Y'''' represents a chlorine atom, a bromine atom or an iodine atom.); and a group represented by —Sn(R$^{C3}$)$_3$ (wherein, each R$^{C3}$ represents a hydrogen atom, an alkyl group, a cycloalkyl group or an aryl group, the foregoing groups each optionally having a substituent. The plurality of R$^{C3}$ may be the same or different and may be combined together to form a cyclic structure together with the tin atom to which they are attached.).

As the group represented by —B(OR$^{C2}$)$_2$, groups represented by the following formulae are exemplified.

[Chemical Formula 68]

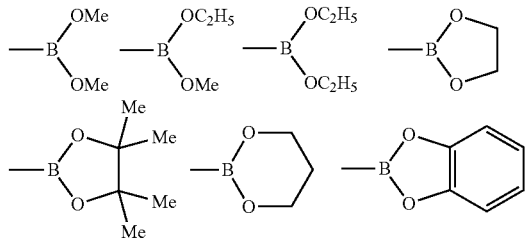

The compound having a group selected from Group A of substituents and the compound having a group selected from Group B of substituents undergo condensation polymerization by a known coupling reaction, thereby giving mutual bonding of carbon atoms linking the group selected from Group A of substituents and the group selected from Group B of substituents. Therefore, when a compound having two groups selected from Group A of substituents and a compound having two groups selected from Group B of substituents are subjected to a known coupling reaction, a condensed polymer of these compounds can be produced by condensation polymerization.

The condensation polymerization is carried out usually in the presence of a catalyst, a base and a solvent, and if necessary, a phase transfer catalyst may coexist.

The catalyst includes, for example, transition metal complexes such as palladium complexes such as dichlorobis (triphenylphosphine)palladium, dichlorobis(tris-o-methoxyphenylphosphine)palladium, palladium[tetrakis (triphenylphosphine)], [tris(dibenzylideneacetone)] dipalladium and palladium acetate, nickel complexes such as nickel[tetrakis(triphenylphosphine)], [1,3-bis(diphenylphosphino)propane]dichloronickel and [bis(1,4-cyclooctadiene)]nickel; these transition metal complexes further having a ligand such as triphenylphosphine, tri-o-tolylphosphine, tri-tert-butylphosphine, tricyclohexylphosphine, diphenylphosphinopropane and bipyridyl. The catalysts may be used singly or in combination.

The use amount of the catalyst is usually 0.00001 to 3 molar equivalents in terms of the amount of a transition metal with respect to the sum of the molar numbers of raw material monomers.

The base and the phase transfer catalyst include, for example, inorganic bases such as sodium carbonate, potassium carbonate, cesium carbonate, potassium fluoride, cesium fluoride and tripotassium phosphate; organic bases such as tetrabutylammonium fluoride and tetrabutylammonium hydroxide; and phase transfer catalysts such as tetrabutylammonium chloride and tetrabutylammonium bromide. The bases and the phase transfer catalysts each may be used singly or in combination.

The use amounts of the base and the phase transfer catalyst are each usually 0.001 to 100 molar equivalents with respect to the total molar number of raw material monomers.

The solvent includes, for example, organic solvents such as toluene, xylene, mesitylene, tetrahydrofuran, 1,4-dioxane, dimethoxyethane, N,N-dimethylacetamide and N,N-dimethylformamide; and water. The solvent may be used singly or two or more solvents may be used in combination.

The use amount of the solvent is usually 10 to 100000 parts by weight with respect to 100 parts by weight of the total amount of raw material monomers.

The reaction temperature of condensation polymerization is usually −100 to 200° C. The reaction time is usually 1 hour or longer.

The post treatment of the polymerization reaction is conducted by known methods, such as a method of removing water-soluble impurities by liquid separation and a method in which the reaction solution resulting from the polymerization reaction is added to a lower alcohol such as methanol and a precipitate deposited is collected by filtration and dried, that are applied individually or in combination. When the polymer compound has a low purity, the polymer host can be purified by a usual method, such as recrystallization, reprecipitation, continuous extraction by a Soxhlet extractor and column chromatography.

<Compound>

Next, the compound as a raw material monomer of the polymer compound of the present invention will be illustrated.

The compound represented by the formula (M-1) is useful as a raw material monomer of the polymer compound of the present invention.

[Chemical Formula 69]

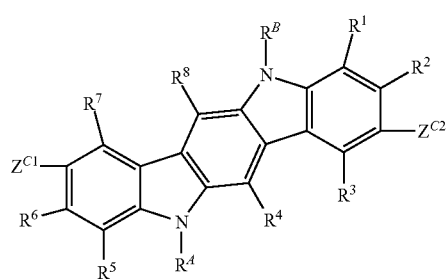

(M-1)

[wherein, $R^1$ to $R^8$, $R^A$, $R^B$, $Z^{C1}$ and $Z^{C2}$ are as defined above.]

The compound represented by the formula (M-1) is preferably a compound represented by the formula (M-1-1), more preferably a compound represented by the formula (M-1-2), when used for production of the polymer compound of the present invention, because a light emitting device using the polymer compound of the present invention is more excellent in light emission efficiency.

[Chemical Formula 70]

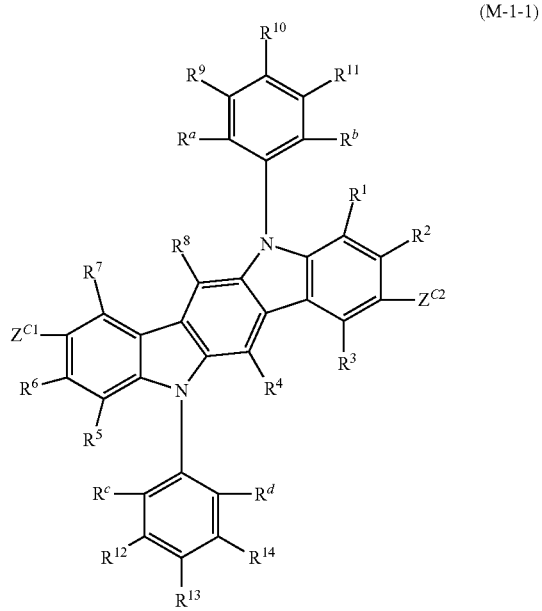

(M-1-1)

[wherein, $R^1$ to $R^{14}$, $R^a$, $R^b$, $R^c$, $R^d$, $Z^{C1}$ and $Z^{C2}$ are as defined above.]

[Chemical Formula 71]

(M-1-2)

When the compound represented by the formula (M-1-2) is used for production of the polymer compound of the present invention, $R^{a'}$, $R^{b'}$, $R^{c'}$ and $R^{d'}$ represent preferably an alkyl group, a cycloalkyl group or an aryl group, more preferably an alkyl group or a cycloalkyl group, particularly preferably an alkyl group, the foregoing groups each optionally having a substituent, because the polymer compound of the present invention is excellent in stability.

The represented by $R^{a1}$, $R^{b1}$, $R^{c1}$ and $R^{d1}$ each optionally has a substituent. The substituent is preferably an alkyl group, a cycloalkyl group or an aryl group.

<Production Method of Compound>

Next, the production method of a compound of the present invention will be illustrated.

The production method of a compound of the present invention is a production method of a compound represented by the formula (M-1'), comprising a step of making a compound represented by the formula (Z) and a compound represented by the formula (2) undergo amination in the presence of a transition metal complex having phosphine as a ligand, a base and a solvent.

[Compound Represented by the Formula (Z)]

[Chemical Formula 72]

(Z)

$R^C$ is preferably an aryl group, because the yield of the compound obtained by the production method of the present invention is more excellent.

The group represented by $R^C$ optionally has a substituent. The substituent is preferably an alkyl group.

The compound represented by the formula (Z) includes, for example, compounds represented by the formulae (Z-1) to (Z-5).

[Chemical Formula 73]

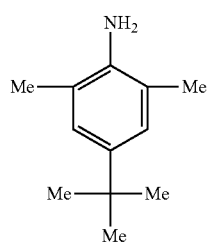
(Z-1)

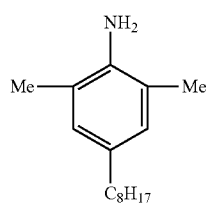
(Z-2)

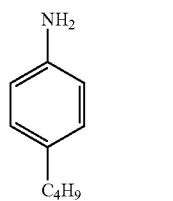
(Z-3)

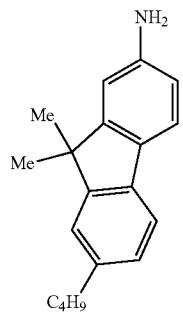
(Z-4)

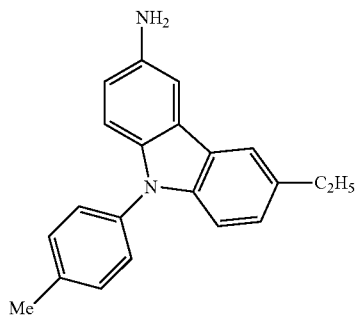
(Z-5)

In the production method of the present invention, the compounds represented by the formula (Z) may be used each singly or two or more of them may be used in combination.

[Compound Represented by the Formula (2)]

[Chemical Formula 74]

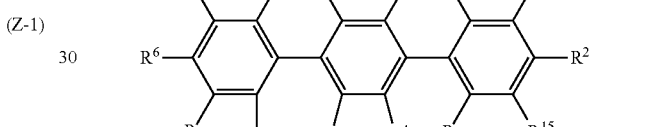
(2)

$R^{15}$ and $R^{16}$ represent preferably a hydrogen atom, an alkyl group, a cycloalkyl group or an aryl group, more preferably a hydrogen atom or an alkyl group, further preferably a hydrogen atom, because the yield of the compound obtained by the production method of the present invention is more excellent.

The group represented by $R^{15}$ and $R^{16}$ each optionally has a substituent. The substituent is preferably an alkyl group.

Each $Y^a$ is preferably a bromine atom or an iodine atom, more preferably a bromine atom, because the yield of the compound obtained by the production method of the present invention is more excellent.

The compound represented by the formula (2) includes, for example, compounds represented by the formulae (2-1) to (2-4).

[Chemical Formula 75]

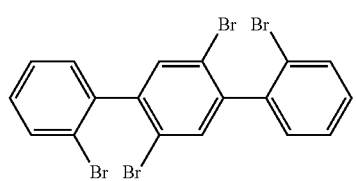
(2-1)

-continued (2-2)
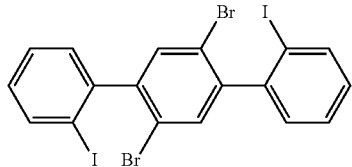

(2-3)
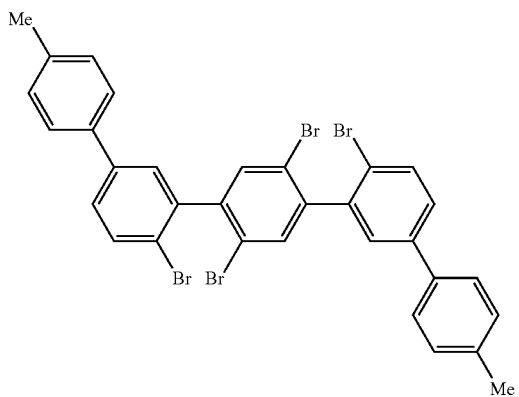

(2-4)
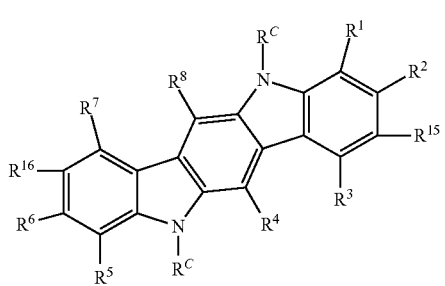

In the production method of the present invention, the compounds represented by the formula (2) may be used each singly or two or more of them may be used in combination.

[Compound Represented by the Formula (M-1')]

[Chemical Formula 76]

(M-1')

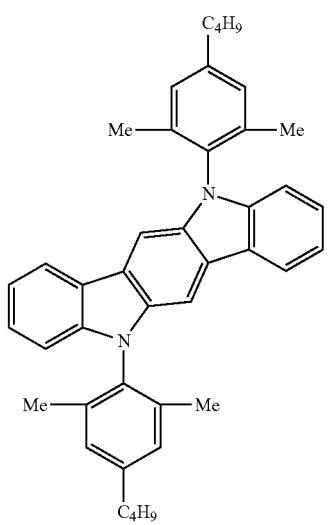

The compound represented by the formula (M-1') is preferably a compound represented by the formula (M-1'-1), because the yield of the compound obtained by the production method of the present invention is more excellent.

[Chemical Formula 77]

(M-1'-1)

The definition and examples of $R^9$ to $R^{14}$, $R^a$, $R^b$, $R^c$ and $R^d$ in the compound represented by the formula (M-1'-1) are the same as the definition and examples of $R^9$ to $R^{14}$, $R^a$, $R^b$, $R^c$ and $R^d$ in the constitutional unit represented by the formula (1-1).

$R^a$, $R^b$, $R^c$ and $R^d$ in the compound represented by the formula (M-1'-1) represent preferably an alkyl group optionally having a substituent, because the yield of the compound obtained by the production method of the present invention is more excellent.

The compound represented by the formula (M-1') includes, for example, compounds represented by the formulae (M-1'-1) to (M-1'-9).

[Chemical Formula 78]

(M-1'-1)

-continued
(M-1'-2)
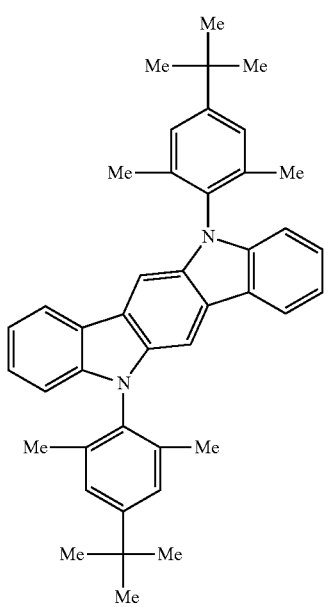
(M-1'-3)
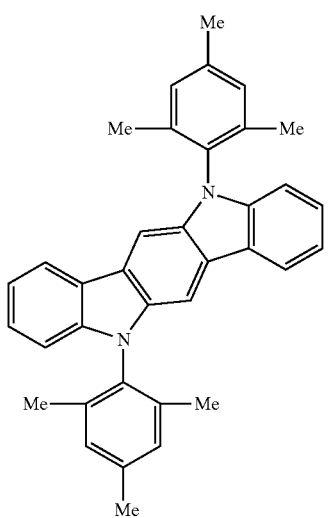
(M-1'-4)
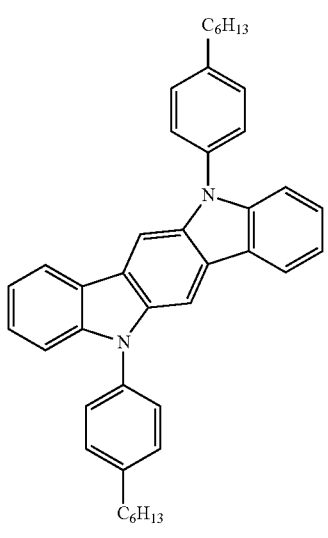
(M-1'-5)
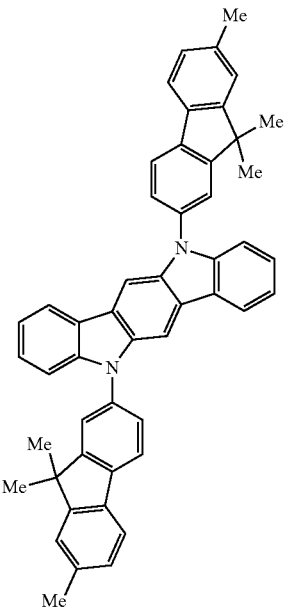
(M-1'-6)
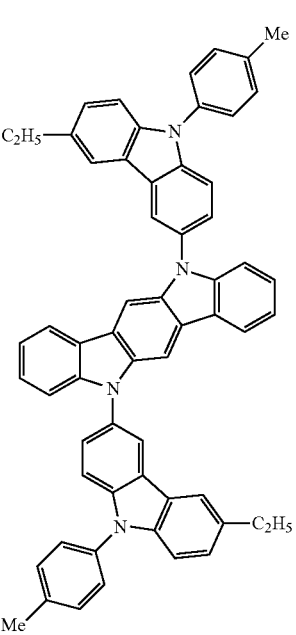
(M-1'-7)
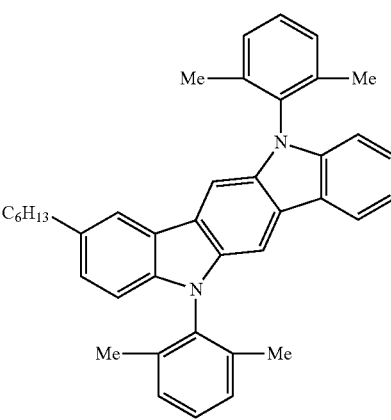

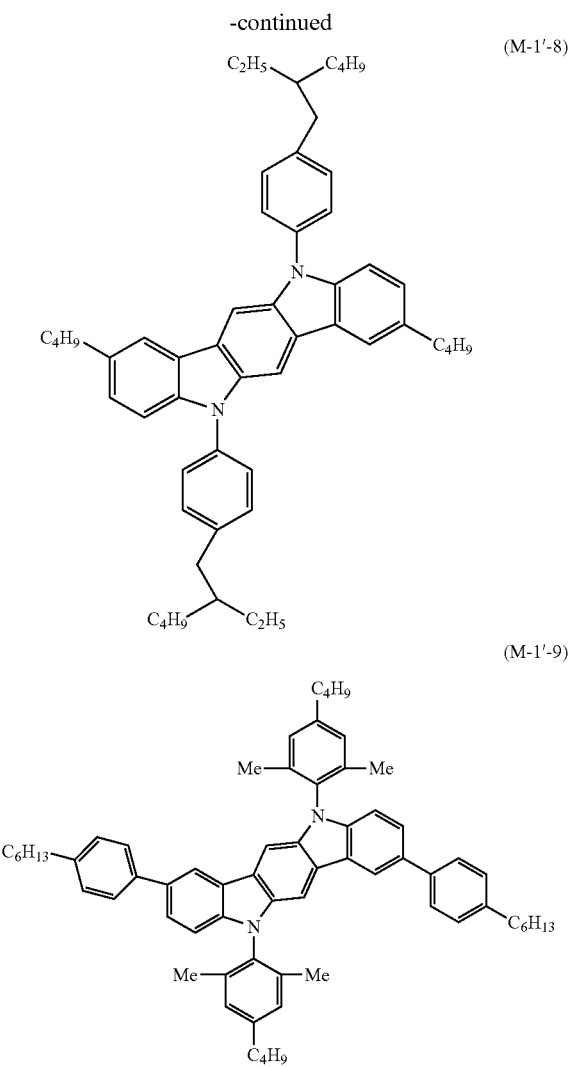

[Transition Metal Complex Having Phosphine Ligand]

The transition metal complex having a phosphine ligand includes a palladium complex having a phosphine ligand and a nickel complex having a phosphine ligand, and a palladium complex having a phosphine ligand is preferable because the yield of the compound obtained by the production method of the present invention is more excellent.

The transition metal complex having a phosphine ligand includes, for example, dichlorobis(triphenylphosphine)palladium, dichlorobis(tris-o-methoxyphenylphosphine)palladium and palladium[tetrakis(triphenylphosphine)].

It is preferable that a transition metal complex having no phosphine ligand and a phosphine compound are added separately into the reaction system and the transition metal complex having a phosphine ligand used in the production method of the present invention is prepared in the reaction system.

The transition metal complex having no phosphine ligand includes, for example, [tris(dibenzylideneacetone)]dipalladium, bis(dibenzylideneacetone)palladium, palladium chloride, palladium acetate and bis(benzonitrile)dichloropalladium, and [tris(dibenzylideneacetone)]dipalladium, bis(dibenzylideneacetone)palladium, palladium chloride or palladium acetate is preferable, [tris(dibenzylideneacetone)]dipalladium or palladium acetate is more preferable.

The phosphine compound includes, for example, phosphine compounds in which at least one group selected from the group consisting of an alkyl group (the alkyl group optionally has a substituent) and an aryl group (the aryl group optionally has a substituent) is bonded to a phosphorus atom, and of them, trialkylphosphine compounds in which three alkyl groups are bonded to a phosphorus atom, or aryl phosphine compounds are preferable.

The phosphine compound includes, for example, triphenylphosphine, tri-o-tolylphosphine, tri-tert-butylphosphine, tricyclohexylphosphine, di-tert-butylphenylphosphine and tri-n-butylphosphine, and tri-tert-butylphosphine or di-tert-butylphenylphosphine is preferable.

When a transition metal complex having no phosphine ligand and a phosphine compound are added separately into the reaction system and the transition metal complex having a phosphine ligand used in the production method of the present invention is prepared in the reaction system, the use amount of the phosphine compound is usually 0.5 to 20 molar equivalent, preferably 1 to 10 molar equivalent, more preferably 1 to 5 molar equivalent, with respect to the total number of moles of the transition metal complex having no phosphine ligand.

When a transition metal complex having no phosphine ligand and a phosphine compound are added separately into the reaction system and the transition metal complex having a phosphine ligand used in the production method of the present invention is prepared in the reaction system, the use amount of the transition metal complex having no phosphine ligand is preferably 0.00001 to 3 molar equivalent, more preferably 0.00005 to 1 molar equivalent, further preferably 0.0001 to 0.5 molar equivalent, with respect to the total number of moles of the compound represented by the formula (2).

In the production method of the present invention, the transition metal complexes having a phosphine ligand may be used each singly or two or more of them may be used in combination.

[Base]

The base used in the production method of the present invention includes, for example, sodium carbonate, potassium hydroxide, sodium hydroxide, potassium carbonate, cesium carbonate, potassium phosphate, sodium tert-butoxide, lithium tert-butoxide and potassium tert-butoxide, and sodium tert-butoxide is preferable.

The use amount of the base is preferably 0.1 to 30 molar equivalent, more preferably 0.5 to 20 molar equivalent, further preferably 1 to 10 molar equivalent, with respect to the total number of moles of the compound represented by the formula (2).

In the production method of the present invention, the bases may be used each singly or two or more of them may be used in combination.

[Solvent]

The solvent used in the production method of the present invention is preferably an organic solvent. The organic solvent includes, for example, toluene, xylene (o-xylene, m-xylene, p-xylene, and a mixture thereof), mesitylene, tetrahydrofuran, 1,4-dioxane, dimethoxyethane, N,N-dimethylacetamide and N,N-dimethylformamide.

The use amount of the solvent is usually 0.1 to 100 parts by weight, preferably 1 to 80 parts by weight, more preferably 5 to 50 parts by weight, when the amount of the compound represented by the formula (2) is 1 part by weight.

In the production method of the present invention, the solvents may be used each singly or two or more of them may be used in combination.

[Reaction Temperature]

In the production method of the present invention, the reaction temperature is usually 0° C. to 200° C., preferably 50° C. to 150° C., more preferably 80° C. to 130° C.

[Reaction Time]

In the production method of the present invention, the reaction time is usually 0.5 to 24 hours, preferably 1 to 12 hours, more preferably 1 to 8 hours.

The compound represented by the formula (M-1-2) as a raw material monomer of the polymer compound of the present invention can be produced, for example, by the following scheme.

[Chemical Formula 79]

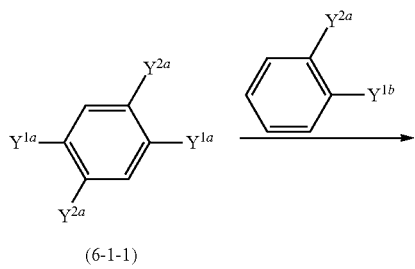

(6-1-1)

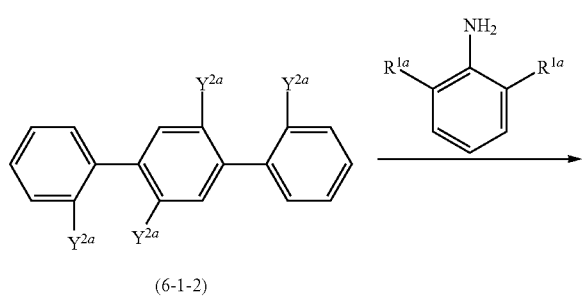

(6-1-2)

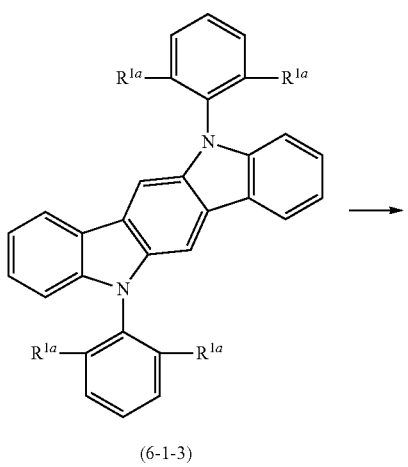

(6-1-3)

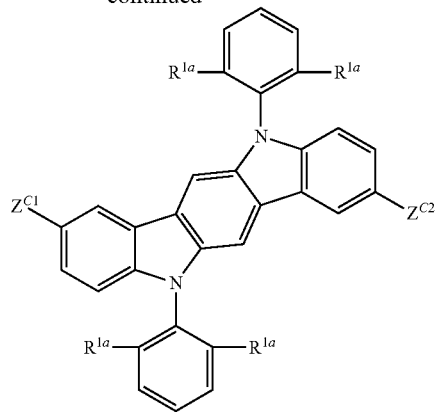

(6-1-4)

[wherein, $Z^{C1}$ and $Z^{C2}$ are as defined above.

$Y^{1a}$ and $Y^{2a}$ represent a chlorine atom, a bromine atom or an iodine atom. $Y^{1a}$ is an atom having an atomic number larger than that of $Y^{2a}$.

$Y^{1b}$ represents a group selected from Group B of substituents.

$R^{1a}$ represents an alkyl group, a cycloalkyl group, an alkoxy group, a cycloalkoxy group, an aryl group, an aryloxy group or a monovalent heterocyclic group, the foregoing groups each optionally having a substituent. The plurality of $R^{1a}$ may be the same or different.]

As the combination of $Y^{1a}$ and $Y^{2a}$, a combination in which $Y^{1a}$ is an iodine atom and $Y^{2a}$ is a bromine atom is preferable.

$R^{1a}$ is preferably an alkyl group, a cycloalkyl group or an aryl group, more preferably an alkyl group or a cycloalkyl group, further preferably an alkyl group, the foregoing groups each optionally having a substituent.

The group represented by $R^{1a}$ optionally has a substituent. The substituent is preferably an alkyl group, a cycloalkyl group or an aryl group.

In the scheme, first, a compound represented by the formula (6-1-1) (hereinafter, referred to as "compound (6-1-1)") and a prescribed halogen compound are subjected to the Suzuki coupling reaction, to obtain a compound represented by the formula (6-1-2) (hereinafter, referred to as "compound (6-1-2)").

In the scheme, next, the compound (6-1-2) and a prescribed amine compound are subjected to a coupling reaction, to obtain a compound represented by the formula (6-1-3) (hereinafter, referred to as "compound (6-1-3)").

In the scheme, next, the compound (6-1-3) is subjected to a reaction such as a bromination reaction, thereby changing a hydrogen atom bonded directly to a carbon atom to a group selected from Group A of substituents, to obtain a compound represented by the formula (6-1-4) (hereinafter, referred to as "compound (6-1-4)"). $Z^{C1}$ and $Z^{C2}$ directly bonded to a carbon atom of the compound (6-1-4) can also be changed to a group selected from Group B of substituents, using a known reaction.

<Composition>

The composition of the present invention comprises the polymer compound of the present invention and at least one material selected from the group consisting of a hole transporting material, a hole injection material, an electron transporting material, an electron injection material, a light emitting material, an antioxidant and a solvent.

The composition comprising the polymer compound of the present invention and a solvent (hereinafter, referred to as "ink" in some cases) is suitable for fabrication of a light emitting device using a printing method such as an inkjet printing method and a nozzle printing method.

The viscosity of the ink may be adjusted depending on the kind of the printing method, and when a solution goes through a discharge apparatus such as in an inkjet printing method, the viscosity is preferably in the range of 1 to 20 mPa·s at 25° C. for preventing curved aviation and clogging in discharging.

As the solvent contained in the ink, those capable of dissolving or uniformly dispersing solid components in the ink are preferable. The solvent includes, for example, chlorine-based solvents such as 1,2-dichloroethane, 1,1,2-trichloroethane, chlorobenzene and o-dichlorobenzene; ether solvents such as tetrahydrofuran, dioxane, anisole and 4-methylanisole; aromatic hydrocarbon solvents such as toluene, xylene, mesitylene, ethylbenzene, n-hexylbenzene and cyclohexylbenzene; aliphatic hydrocarbon solvents such as cyclohexane, methylcyclohexane, n-pentane, n-hexane, n-heptane, n-octane, n-nonane, n-decane, n-dodecane and bicyclohexyl; ketone solvents such as acetone, methylethylketone, cyclohexanone and acetophenone; ester solvents such as ethyl acetate, butyl acetate, ethylcellosolve acetate, methyl benzoate and phenyl acetate; poly-hydric alcohols such as ethylene glycol, glycerin and 1,2-hexanediol and derivatives thereof; alcohol solvents such as isopropanol and cyclohexanol; sulfoxide solvents such as dimethyl sulfoxide; and amide solvents such as N-methyl-2-pyrrolidone and N,N-dimethylformamide. These solvents may be used singly or two or more of them may be used in combination.

In the ink, the compounding amount of the solvent is usually 1000 to 100000 parts by weight, preferably 2000 to 20000 parts by weight with respect to 100 parts by weight of the polymer compound of the present invention.

[Hole Transporting Material]

The hole transporting material is classified into low molecular weight compounds and polymer compounds, and polymer compounds are preferable, polymer compounds having a crosslinkable group are more preferable.

The polymer compound includes, for example, polyvinylcarbazole and derivatives thereof; polyarylene having an aromatic amine structure in the side chain or main chain and derivatives thereof. The polymer compound may also be a compound in which an electron accepting portion is linked. The electron accepting portion includes, for example, fullerene, tetrafluorotetracyanoquinodimethane, tetracyanoethylene and trinitrofluorenone, preferably fullerene.

In the composition of the present invention, the compounding amount of the hole transporting material is usually 1 to 400 parts by weight, preferably 5 to 150 parts by weight with respect to 100 parts by weight of the polymer compound of the present invention.

The hole transporting material may be used singly or two or more hole transporting materials may be used in combination.

[Electron Transporting Material]

The electron transporting material is classified into low molecular weight compounds and polymer compounds. The electron transporting material optionally has a crosslinkable group.

The low molecular weight compound includes, for example, a metal complexe having 8-hydroxyquinoline as a ligand, oxadiazole, anthraquinodimethane, benzoquinone, naphthoquinone, anthraquinone, tetracyanoanthraquinodimethane, fluorenone, diphenyldicyanoethylene, diphenoquinone and derivatives thereof. The polymer compound includes, for example, polyphenylene, polyfluorene and derivatives thereof. These polymer compounds may be doped with a metal.

In the composition of the present invention, the compounding amount of the electron transporting material is usually 1 to 400 parts by weight, preferably 5 to 150 parts by weight with respect to 100 parts by weight of the polymer compound of the present invention.

The electron transporting material may be used singly or two or more electron transporting materials may be used in combination.

[Hole Injection Material and Electron Injection Material]

The hole injection material and the electron injection material are each classified into low molecular weight compounds and polymer compounds. The hole injection material and the electron injection material each optionally has a crosslinkable group.

The low molecular weight compound includes, for example, metal phthalocyanines such as copper phthalocyanine; carbon; oxides of metals such as molybdenum and tungsten; metal fluorides such as lithium fluoride, sodium fluoride, cesium fluoride and potassium fluoride.

The polymer compound includes, for example, polyaniline, polythiophene, polypyrrole, polyphenylenevinylene, polythienylenevinylene, polyquinoline and polyquinoxaline, and derivatives thereof; electrically conductive polymers such as a polymer comprising an aromatic amine structure in the main chain or side chain.

In the composition of the present invention, the compounding amounts of the hole injection material and the electron injection material are each usually 1 to 400 parts by weight, preferably 5 to 150 parts by weight with respect to 100 parts by weight of the polymer compound of the present invention.

The hole injection material and the electron injection material may each be used singly or two or more of them may be used in combination.

[Ion Dope]

When the hole injection material or the electron injection material comprises an electrically conductive polymer, the electric conductivity of the electrically conductive polymer is preferably $1 \times 10^{-5}$ S/cm to $1 \times 10^{3}$ S/cm. For adjusting the electric conductivity of the electrically conductive polymer within such a range, the electrically conductive polymer can be doped with a suitable amount of ions.

The kind of the ion to be doped is an anion for a hole injection material and a cation for an electron injection material. The anion includes, for example, a polystyrenesulfonate ion, an alkylbenzenesulfonate ion and a camphorsulfonate ion. The cation includes, for example, a lithium ion, a sodium ion, a potassium ion and a tetrabutylammonium ion.

The ion to be doped may be used singly or two or more ions to be doped may be used.

[Light Emitting Material]

The light emitting material is classified into low molecular weight compounds and polymer compounds. The light emitting material optionally has a crosslinkable group.

The low molecular weight compound includes, for example, naphthalene and derivatives thereof, anthracene and derivatives thereof, perylene and derivatives thereof, and, triplet light emitting complexes having iridium, platinum or europium as the central metal.

The polymer compound includes, for example, polymer compounds comprising a phenylene group, a naphthalenediyl group, an anthracenediyl group, a fluorenediyl group, a phenanthrenediyl group, dihydrophenanthrenediyl group, a group represented by the formula (X), a carbazolediyl group, a phenoxazinediyl group, a phenothiazinediyl group, a pyrenediyl group and the like.

The light emitting material may comprise a low molecular weight compound and a polymer compound, and preferably, comprises a triplet light emitting complex and a polymer compound.

As the triplet light emitting complex, iridium complexes represented by the formulae Ir-1 to Ir-5 are preferable.

[Chemical Formula 80]

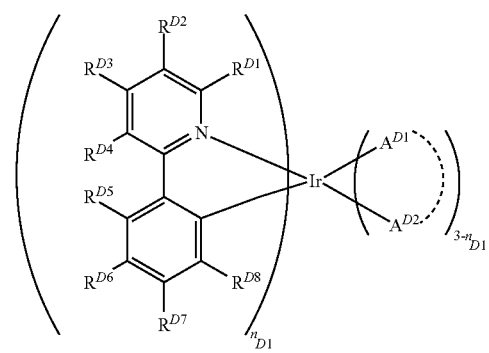

Ir-1

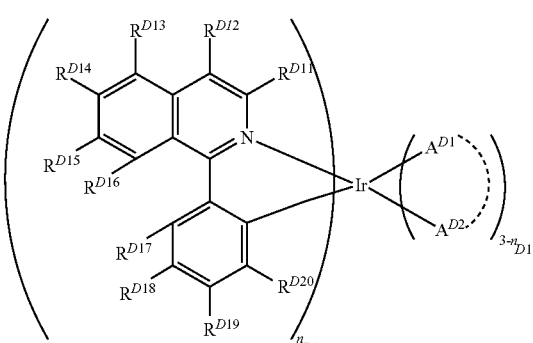

Ir-2

[Chemical Formula 81]

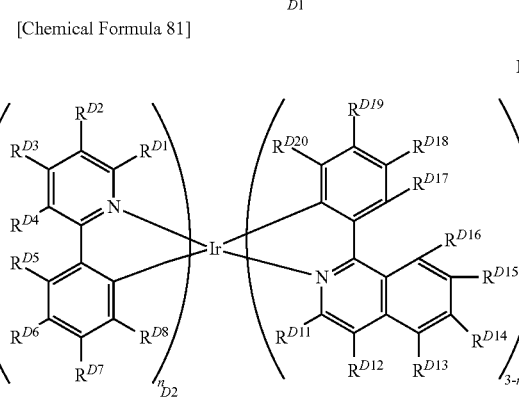

Ir-3

[Wherein, $R^{D1}$ to $R^{D8}$ and $R^{D11}$ to $R^{D20}$ each independently represent a hydrogen atom, an alkyl group, a cycloalkyl group, an alkoxy group, a cycloalkoxy group, an aryl group, an aryloxy group, a monovalent heterocyclic group or a halogen atom, the foregoing groups each optionally having a substituent. When a plurality of $R^{D1}$ to $R^{D8}$ and $R^{D11}$ to $R^{D20}$ are present, they may be the same or different at each occurrence.

-$A^{D1}$---$A^{D2}$- represents an anionic bidentate ligand, and $A^{D1}$ and $A^{D2}$ each independently represent a carbon atom, an oxygen atom or a nitrogen atom linking to an iridium atom, and these atoms each may be an atom consisting a ring. When a plurality of -$A^{D1}$---$A^{D2}$- are present, they may be the same or different.

$n_{D1}$ represents 1, 2 or 3, and $n_{D2}$ represents 1 or 2.]

In the triplet light emitting complex represented by the Ir-1, at least one of $R^{D1}$ to $R^{D8}$ is preferably a group represented by the formula (D-A).

[Chemical Formula 82]

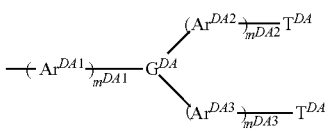

(D-A)

[wherein, $m^{DA1}$, $m^{DA2}$ and $m^{DA3}$ each independently represent an integer of 0 or more.

$G^{DA}$ represents a nitrogen atom, an aromatic hydrocarbon group or a heterocyclic group, the foregoing groups each optionally having a substituent.

$Ar^{DA1}$, $Ar^{DA2}$ and $Ar^{DA3}$ each independently represent an arylene group or a divalent heterocyclic group, the foregoing groups each optionally having a substituent. When a plurality of $Ar^{DA1}$, $Ar^{DA2}$ and $Ar^{DA3}$ are present, they may be the same or different at each occurrence.

$T^{DA}$ represents an aryl group or a monovalent heterocyclic group, the foregoing groups each optionally having a substituent. The plurality of $T^{DA}$ may be the same or different.]

$m^{DA1}$, $m^{DA2}$ and $m^{DA3}$ are usually an integer of 10 or less, preferably an integer of 5 or less, more preferably 0 or 1. It is preferable that $m^{DA1}$, $m^{DA2}$ and $m^{DA3}$ are the same integer.

$G^{DA}$ is preferably a group represented by the formula (GDA-11) to (GDA-15), the foregoing groups each optionally having a substituent.

[Chemical Formula 83]

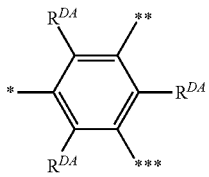

(GDA-11)

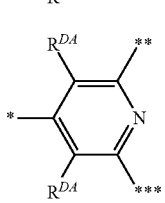

(GDA-12)

-continued

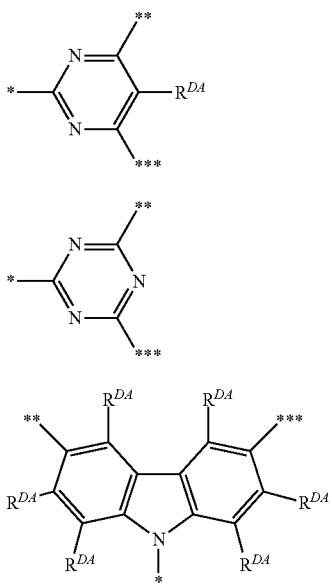

(GDA-13)

(GDA-14)

(GDA-15)

[wherein,

*,  and * each represent a linkage to $Ar^{DA1}$, $Ar^{DA2}$ and $Ar^{DA3}$.

$R^{DA}$ represents a hydrogen atom, an alkyl group, a cycloalkyl group, an alkoxy group, a cycloalkoxy group, an aryl group or a monovalent heterocyclic group, the foregoing groups each optionally further having a substituent. When a plurality of $R^{DA}$ are present, they may be the same or different.]

$R^{DA}$ is preferably a hydrogen atom, an alkyl group, a cycloalkyl group, an alkoxy group or a cycloalkoxy group, more preferably a hydrogen atom, an alkyl group or cycloalkyl group, the foregoing groups each optionally having a substituent.

$Ar^{DA1}$, $Ar^{DA2}$ and $Ar^{DA3}$ are preferably groups represented by the formulae (ArDA-1) to (ArDA-3).

[Chemical Formula 84]

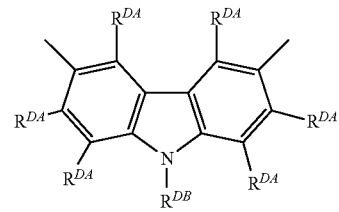

(ArDA-1)

(ArDA-2)

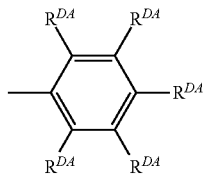

(ArDA-3)

[wherein, $R^{DA}$ represents the same meaning as described above.

$R^{DB}$ represents a hydrogen atom, an alkyl group, a cycloalkyl group, an aryl group or a monovalent heterocyclic group, the foregoing groups each optionally having a substituent. When a plurality of $R^{DB}$ are present, they may be the same or different.]

$T^{DA}$ is preferably groups represented by the formulae (TDA-1) to (TDA-3).

[Chemical Formula 85]

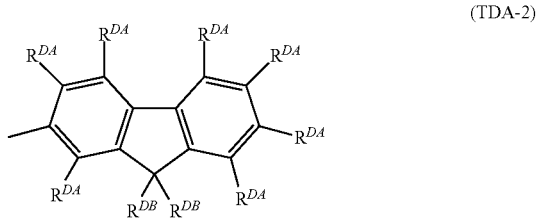

(TDA-1)

(TDA-2)

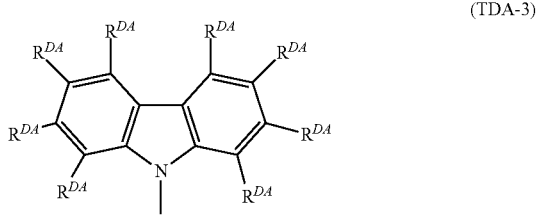

(TDA-3)

[wherein, $R^{DA}$ and $R^{DB}$ represent the same meaning described above.]

In the formula Ir-2, at least one of $R^{D11}$ to $R^{D20}$ is preferably a group represented by the formula (D-A)

In the formula Ir-3, at least one of $R^{D1}$ to $R^{D8}$ and $R^{D11}$ to $R^{D20}$ is preferably a group represented by the formula (D-A)

The group represented by the formula (D-A) is preferably a group represented by the formula (D-A1) to (D-A3).

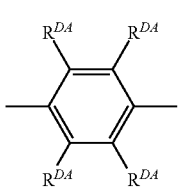

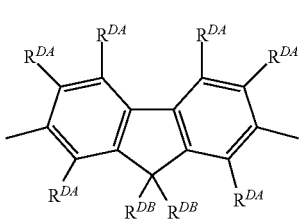

[Chemical Formula 86]

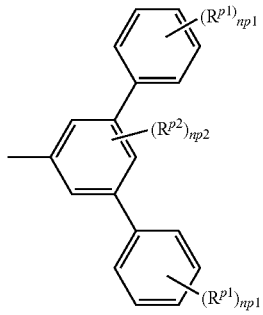
(D-A1)

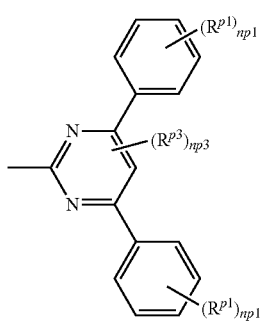
(D-A2)

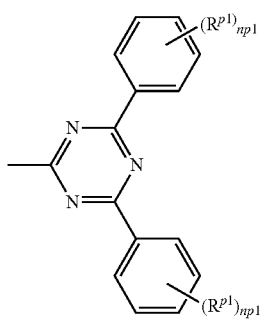
(D-A3)

[wherein, $R^{p1}$, $R^{p2}$ and $R^{p3}$ each independently represent an alkyl group, a cycloalkyl group, an alkoxy group, a cycloalkoxy group or a halogen atom. When a plurality of $R^{p1}$ and $R^{p2}$ are present, they may be the same or different at each occurrence.

np1 represents an integer of 0 to 5, np2 represents an integer of 0 to 3, and np3 represents 0 or 1. The plurality of np1 may be the same or different.]

np1 is preferably 0 or 1, more preferably 1. np2 is preferably 0 or 1, more preferably 0. np3 is preferably 0.

$R^{p1}$, $R^{p2}$ and $R^{p3}$ are preferably an alkyl group or a cycloalkyl group.

The anionic bidentate ligand represented by -$A^{D1}$---$A^{D2}$- includes, for example, ligands represented by the following formulae.

[Chemical Formula 87]

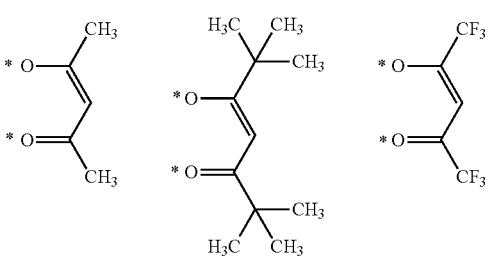

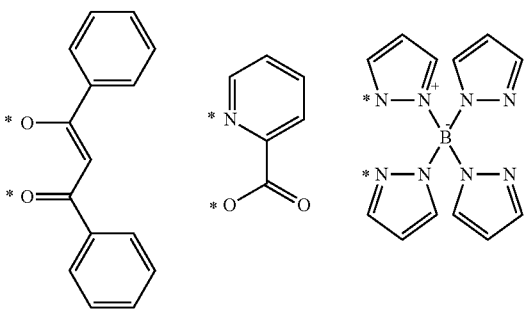

[wherein, * represents a position linking to Ir.]

The metal complex represented by the formula Ir-1 is preferably a metal complex represented by the formula Ir-11 to Ir-13. The metal complex represented by the formula Ir-2 is preferably a metal complex represented by the formula Ir-21. The metal complex represented by the formula Ir-3 is preferably a metal complexe represented by the formula Ir-31 to Ir-33.

[Chemical Formula 88]
Ir-11
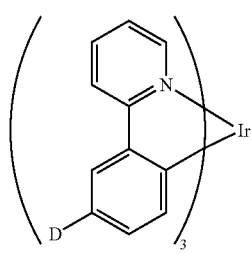
Ir-12
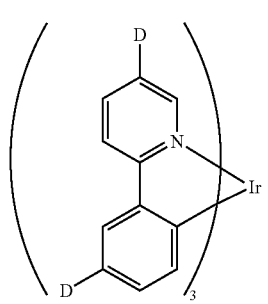
Ir-13
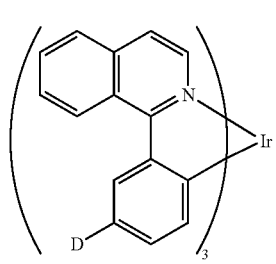
Ir-21
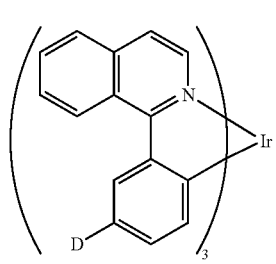
[Chemical Formula 89]
Ir-11
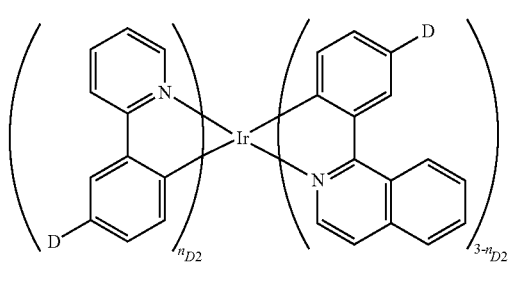
Ir-12
Ir-31
Ir-32
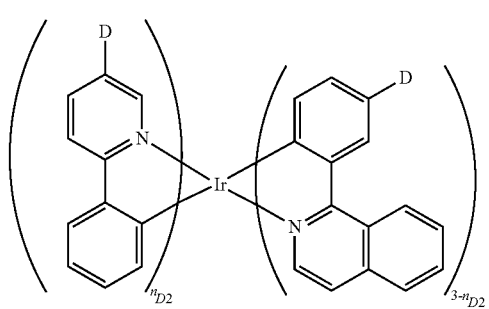
Ir-13
[Chemical Formula 90]
Ir-33
[wherein, D represents a group represented by the formula (D-A). $n_{D2}$ represents 1 or 2.]
The triplet light emitting complex includes, for example, metal complexes listed below.

[Chemical Formula 91]
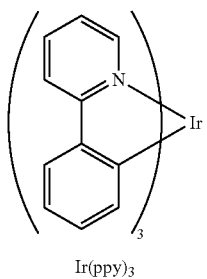
Ir(ppy)₃
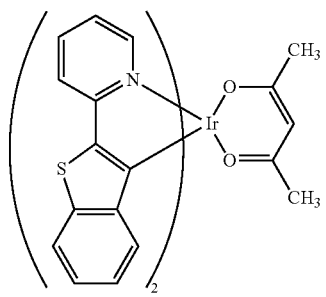
Btp₂Ir(acac)
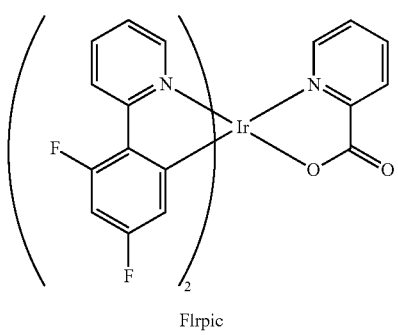
FIrpic
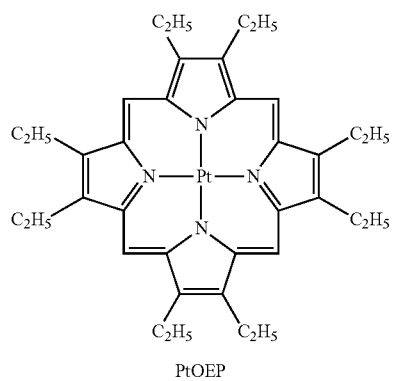
PtOEP
[Chemical Formula 92]
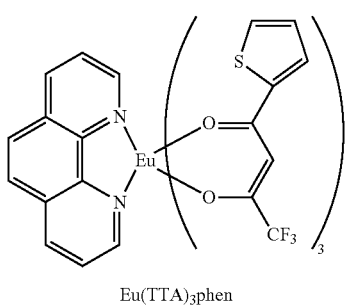
Eu(TTA)₃phen
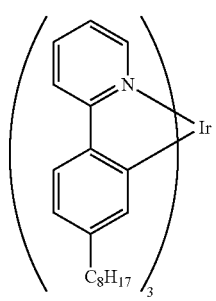
COM-1
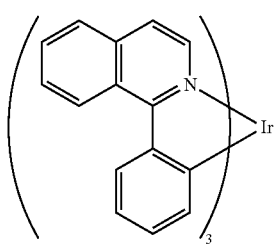
COM-2
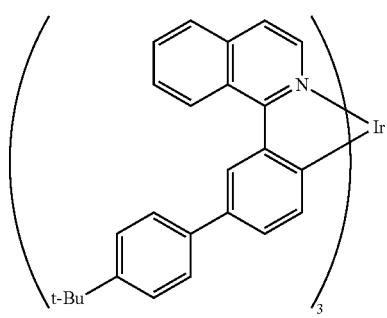
COM-3

[Chemical Formula 93]
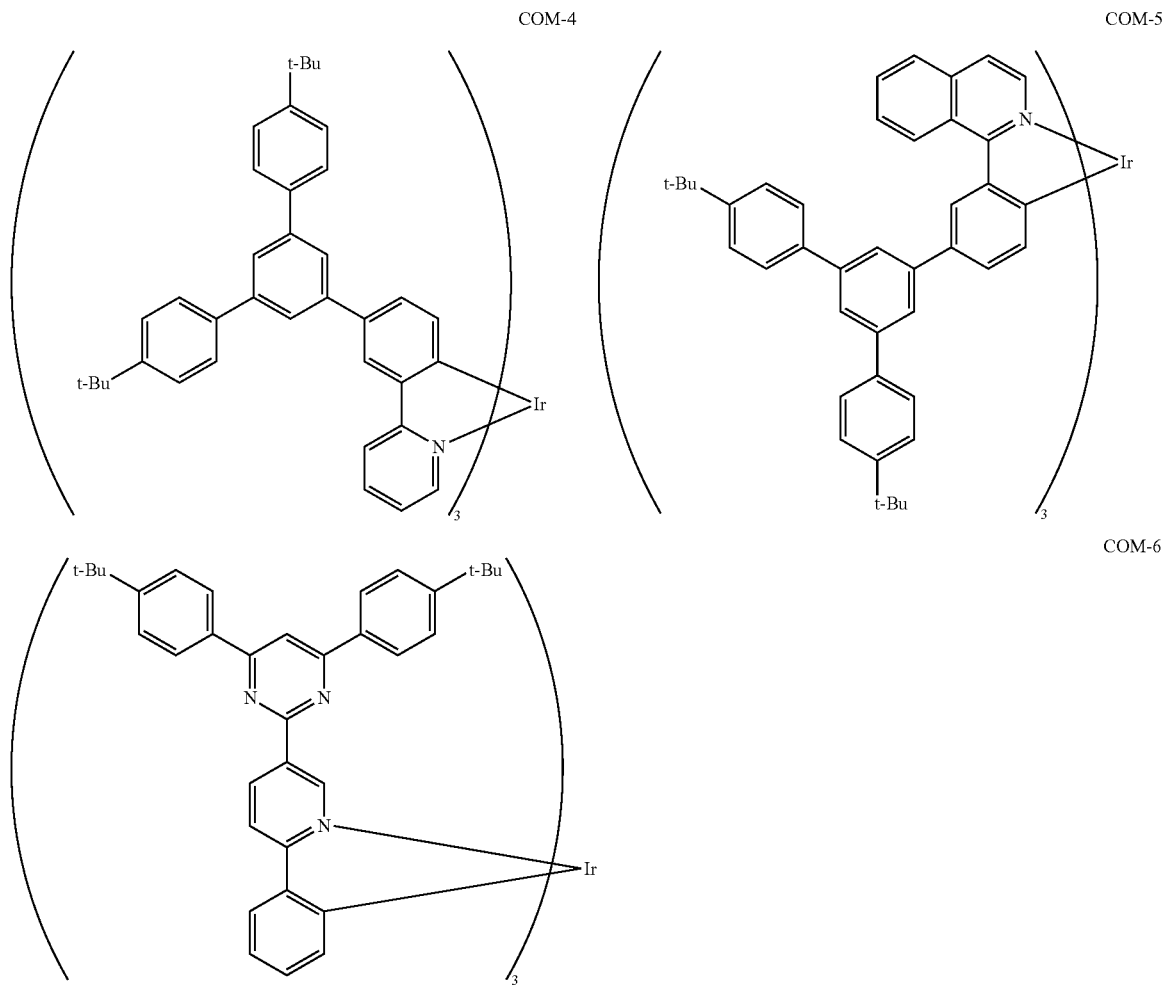
[Chemical Formula 94]
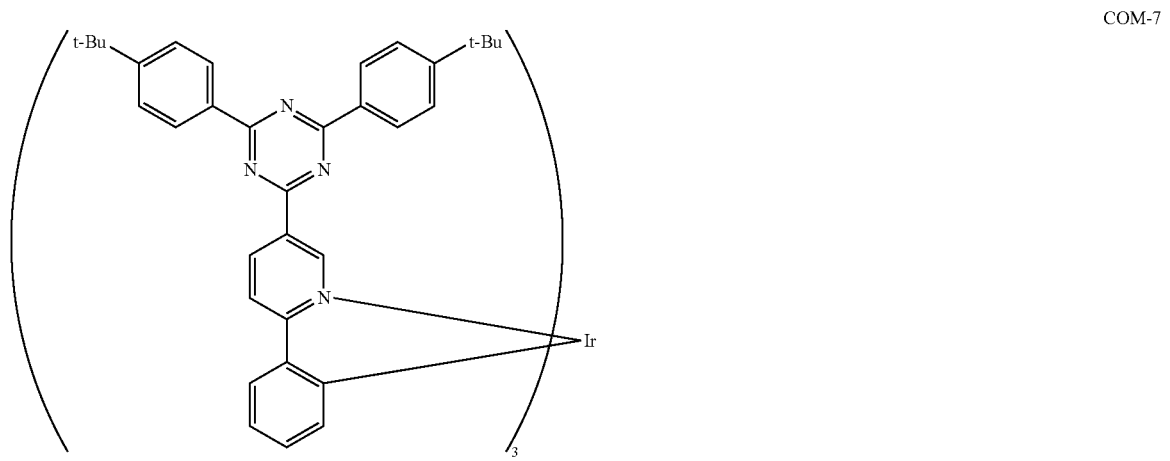

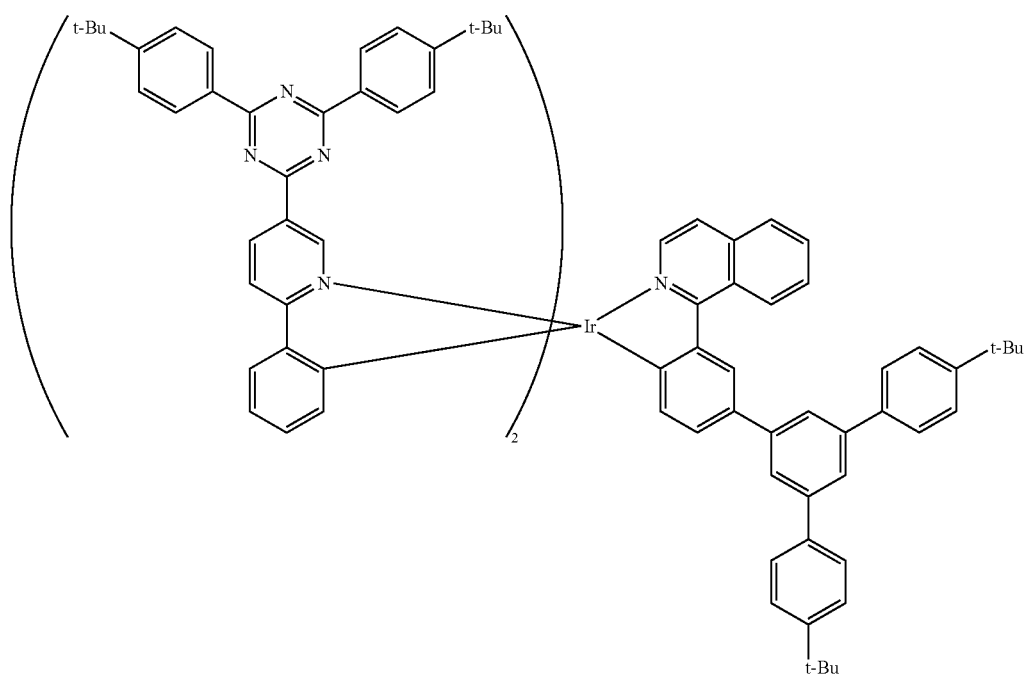

COM-8

In the composition of the present invention, the compounding amount of the light emitting material is usually 0.1 to 400 parts by weight with respect to 100 parts by weight of the polymer compound of the present invention.

[Antioxidant]

The antioxidant may advantageously be one which is soluble in the same solvent as for the polymer compound of the present invention and does not disturb light emission and charge transportation, and the examples thereof include phenol antioxidants and phosphorus-based antioxidants.

In the composition of the present invention, the compounding amount of the antioxidant is usually 0.001 to 10 parts by weight with respect to 100 parts by weight of the polymer compound of the present invention.

The antioxidant may be used singly or two or more antioxidants may be used in combination.

<Film>

The film contains the polymer compound of the present invention.

The film includes also an insolubilized film obtained by insolubilizing the polymer compound of the present invention in a solvent by cross-linkage. The insolubilized film is a film obtained by cross-linking the polymer compound of the present invention by an external stimulus such as heating, light irradiation and the like. The insolubilized film can be suitably used for lamination of a light emitting device because the film is substantially insoluble in a solvent.

150~200° C. である。

The heating temperature for crosslinking the film is usually 25 to 300° C., and because the light emission efficiency is improved, preferably 50 to 250° C., more preferably 150 to 200° C.

The kind of light used in light irradiation for crosslinking the film includes, for example, ultraviolet light, near-ultraviolet light and visible light.

The film is suitable as a light emitting layer in a light emitting device.

The film can be fabricated, for example, by a spin coating method, a casting method, a micro gravure coating method, a gravure coating method, a bar coating method, a roll coating method, a wire bar coating method, a dip coating method, a spray coating method, a screen printing method, a flexo printing method, an offset printing method, an inkjet printing method, a capillary coating method or a nozzle coating method, using the ink.

The thickness of the film is usually 1 nm to 10 μm.

<Light Emitting Device>

The light emitting device of the present invention is a light emitting device such as an organic electroluminescent device and the like obtained by using the polymer compound of the present invention. When the polymer compound of the present invention has a cross-link group, the light emitting device is, for example, a light emitting device containing the polymer compound of the present invention or a light emitting device in which the polymer compound of the present invention is intramolecularly cross-linked, intermolecularly cross-linked or cross-linked in both modes, while when the polymer compound of the present invention has no cross-link group, the light emitting device is, for example, a light emitting device containing the polymer compound of the present invention.

The constitution of the light emitting device of the present invention has, for example, electrodes consisting of an anode and a cathode, and a layer obtained by using the polymer compound of the present invention disposed between the electrodes.

[Layer Constitution]

The layer produced by using the polymer compound of the present invention is usually at least one selected from a light emitting layer, a hole transporting layer, a hole injection layer, an electron transporting layer and an electron injection layer, preferably a light emitting layer. These layers comprise a light emitting material, a hole transporting material, a hole injection material, an electron transporting material and an electron injection material, respectively. These layers can be formed by the same method as the film fabrication using inks prepared by dissolving a light emitting material, a hole transporting material, a hole injection material, an electron transporting material and an electron injection material, respectively, in the solvent described above.

The light emitting device comprises a light emitting layer between an anode and a cathode. The light emitting device of the present invention preferably comprises at least one of a hole injection layer and a hole transporting layer between an anode and a light emitting layer from the standpoint of hole injectability and hole transportability, and preferably comprises at least one of an electron injection layer and an electron transporting layer between a cathode and a light emitting layer from the standpoint of electron injectability and electron transportability.

The material of a hole transporting layer, an electron transporting layer, a light emitting layer, a hole injection layer and an electron injection layer includes the hole transporting materials, electron transporting materials, light emitting materials, hole injection materials and electron injection materials, respectively, in addition to the polymer compound of the present invention.

When the material of a hole transporting layer, the material of an electron transporting layer and the material of a light emitting layer are soluble in a solvent which is used in forming a layer adjacent to the hole transporting layer, the electron transporting layer and the light emitting layer, respectively, in fabrication of a light emitting device, it is preferable that the materials have a crosslinkable group to avoid dissolution of the materials in the solvent. After forming the layers using the materials having a crosslinkable group, the layers can be insolubilized by crosslinking the crosslinkable group.

Methods of forming respective layers such as a light emitting layer, a hole transporting layer, an electron transporting layer, a hole injection layer and an electron injection layer in the light emitting device of the present invention include, for example, a method of vacuum vapor deposition from a powder and a method of film formation from solution or melted state when a low molecular weight compound is used, and, for example, a method of film formation from solution or melted state when a polymer compound is used.

The order and the number of layers to be laminated and the thickness of each layer may be controlled in view of light emission efficiency and device life.

[Substrate/electrode]

The substrate in the light emitting device may advantageously be a substrate on which an electrode can be formed and which does not chemically change in forming an organic layer, and is a substrate made of a material such as, for example, glass, plastic and silicon. In the case of an opaque substrate, it is preferable that an electrode most remote from the substrate is transparent or semi-transparent.

The material of the anode includes, for example, electrically conductive metal oxides and semi-transparent metals, preferably, indium oxide, zinc oxide and tin oxide; electrically conductive compounds such as indium•tin•oxide (ITO) and indium•zinc•oxide; a composite of silver, palladium and copper (APC); NESA, gold, platinum, silver and copper.

The material of the cathode includes, for example, metals such as lithium, sodium, potassium, rubidium, cesium, beryllium, magnesium, calcium, strontium, barium, aluminum, zinc and indium; alloys composed of two or more of them; alloys composed of one or more of them and at least one of silver, copper, manganese, titanium, cobalt, nickel, tungsten and tin; and graphite and graphite intercalation compounds. The alloy includes, for example, a magnesium-silver alloy, a magnesium-indium alloy, a magnesium-aluminum alloy, an indium-silver alloy, a lithium-aluminum alloy, a lithium-magnesium alloy, a lithium-indium alloy and a calcium-aluminum alloy.

The anode and the cathode may each take a lamination structure composed of two or more layers.

[Use]

For producing planar light emission by using a light emitting device, a planar anode and a planar cathode are disposed so as to overlap with each other. Patterned light emission can be produced by a method of placing a mask with a patterned window on the surface of a planer light emitting device, a method of forming extremely thick a layer intended to be a non-light emitting, thereby having the layer essentially no-light emitting or a method of forming an anode, a cathode or both electrodes in a patterned shape. By forming a pattern with any of these methods and disposing certain electrodes so as to switch ON/OFF independently, a segment type display capable of displaying numbers and letters and the like is provided. For producing a dot matrix display, both an anode and a cathode are formed in a stripe shape and disposed so as to cross with each other. Partial color display and multi-color display are made possible by a method of printing separately certain polymer compounds showing different emission or a method of using a color filter or a fluorescence conversion filter. The dot matrix display can be passively driven, or actively driven combined with TFT and the like. These displays can be used in computers, television sets, portable terminals and the like. The planar light emitting device can be suitably used as a planer light source for backlight of a liquid crystal display or as a planar light source for illumination. If a flexible substrate is used, it can be used also as a curved light source and a curved display.

EXAMPLES

The present invention will be illustrated further in detail by examples below, but the present invention is not limited to these examples.

In the present examples, the polystyrene-equivalent number average molecular weight (Mn) and the polystyrene-equivalent weight average molecular weight (Mw) of a polymer compound were measured by size exclusion chromatography (SEC) (manufactured by Shimadzu Corp., trade name: LC-10Avp). SEC measurement conditions are as described below.

[Measurement Condition]

The polymer compound to be measured was dissolved in THF at a concentration of about 0.05 wt %, and 10 μL of the solution was injected into SEC. As the mobile phase of SEC, THF was used and allowed to flow at a flow rate of 2.0 mL/min. As the column, PLgel MIXED-B (manufactured by Polymer Laboratories) was used. As the detector, UV-VIS detector (manufactured by Shimadzu Corp., trade name: SPD-10Avp) was used.

Measurement of liquid chromatograph mass spectrometry (LC-MS) was carried out according to the following method.

A measurement sample was dissolved in chloroform or THF so as to give a concentration of about 2 mg/mL, and about 1 μL of the solution was injected into LC-MS (manufactured by Agilent Technologies, trade name: 1100LCMSD). As the mobile phase of LC-MS, acetonitrile and THF were used while changing the ratio thereof and allowed to flow at a flow rate of 0.2 mL/min. As the column, L-column 2 ODS (3 μm) (manufactured by Chemicals Evaluation and Research Institute, internal diameter: 2.1 mm, length: 100 mm, particle size: 3 μm) was used.

Measurement of NMR was carried out according to the following method.

5 to 10 mg of a measurement sample was dissolved in about 0.5 mL of deuterated chloroform ($CDCl_3$), deuterated tetrahydrofuran (THF-$d_8$), deuterated methylene chloride ($CD_2Cl_2$) or deuterated dimethyl sulfoxide (($CD_3$)$_2$SO) and measurement was performed using an NMR apparatus (manufactured by Varian, Inc., trade name: MERCURY 300).

As the index of the purity of a compound, a value of the high performance liquid chromatography (HPLC) area percentage was used. This value is a value in high performance liquid chromatography (HPLC, manufactured by Shimadzu Corp., trade name: LC-20A) at 254 nm, unless otherwise state. In this operation, the compound to be measured was dissolved in THF or chloroform so as to give a concentration of 0.01 to 0.2 wt %, and depending on the concentration, 1 to 10 μL of the solution was injected into HPLC. As the mobile phase of HPLC, acetonitrile and THF were used and allowed to flow at a flow rate of 1 mL/min as gradient analysis of acetonitrile/THF=100/0 to 0/100 (volume ratio). As the column, Kaseisorb LC ODS 2000 (manufactured by Tokyo Chemical Industry Co., Ltd.) or an ODS column having an equivalent performance was used. As the detector, a photo diode array detector (manufactured by Shimadzu Corp., trade name: SPD-M20A) was used.

Synthesis Example 1

Synthesis of Compound 2

[Chemical Formula 95]

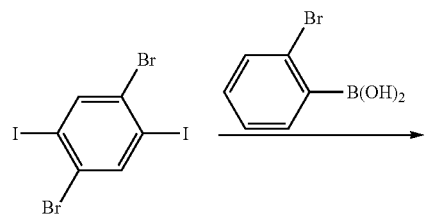

Compound 1

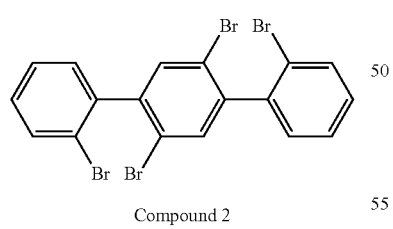

Compound 2

A nitrogen gas atmosphere was prepared in a reaction vessel equipped with a stirrer, then, a compound 1 (22.0 g), 2-bromophenylboronic acid (19.1 g), tetrakis(triphenylphosphine)palladium(0) (2.43 g) and tetrahydrofuran (440 mL) were added, and the mixture was heated at 45° C. Thereafter, to this was added silver carbonate (47.2 g), and the mixture was refluxed for 3 hours. The resultant reaction liquid was cooled down to room temperature, then, water and toluene were added, and the mixture was stirred at room temperature. Thereafter, the aqueous layer was separated, and the organic layer was washed with a saturated sodium chloride aqueous solution. To the resultant organic layer was added sodium sulfate, then, the layer was filtrated, and concentrated to obtain a coarse product. Thereafter, to this were added toluene and activated carbon, and the mixture was stirred at 70° C. for 1 hour. Thereafter, the mixture was filtrated through a filter pre-coated with Celite. The resultant residue was washed with toluene several times. The resultant washing liquid was concentrated, then, recrystallized using toluene, thereby obtaining 17.9 g of a compound 2 (yield: 74%, purity: 98.9%) as a white solid.

$^1$H-NMR (DMSO-$d_6$, 300 MHz): δ (ppm)=7.43 (4H, t), 7.49 (2H, t), 7.71 (2H, d), 7.76 (2H, d).

Example 1

Synthesis of Compound 3

[Chemical Formula 96]

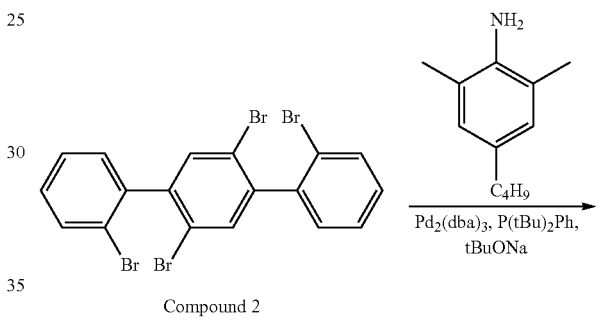

Compound 2

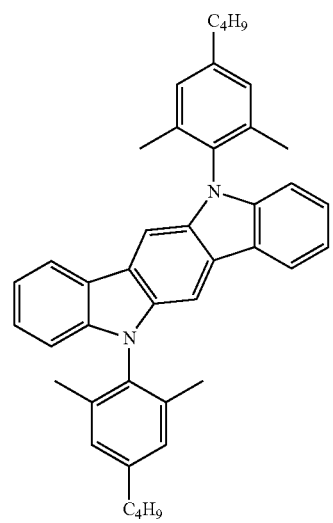

Compound 3

A nitrogen gas atmosphere was prepared in a reaction vessel equipped with a stirrer, then, 2,6-dimethyl-4-n-butylaniline (3.8 g), sodium tert-butoxide (4.9 g) and tert-butanol (3.3 ml) were added. Thereafter, to this was added toluene (30 mL), and the mixture was heated up to 105° C., then, stirred at 105° C. for 30 minutes. Thereafter, to this were added tris(dibenzylideneacetone)dipalladium(0) (0.40 g) and di-tert-butylphenylphosphine (0.39 g), then, the compound 2 (4.8 g) and toluene (80 mL) were added, then, the mixture was stirred at 105° C. for 2.5 hours. The resultant reaction liquid was cooled down to room temperature, then, water and toluene were added, and the mixture was stirred at room temperature. The organic layer was analyzed by HPLC (high performance liquid chromatography) to resultantly find generation of a compound 3 as the target compound at a yield of 95%. Thereafter, the aqueous layer was separated, and the organic layer was washed with a saturated sodium chloride aqueous solution. To the resultant organic layer was added magnesium sulfate, then, the layer was filtrated, and concentrated to obtain a coarse product. The resultant coarse product was washed with heptane several times, then, recrystallized using toluene, thereby obtaining 3.8 g of a compound 3 (yield: 77%, purity: 99.6%) as a white solid.

LC-MS (APCI, positive): [M+H]$^+$ 577

$^1$H-NMR (THF-d$_6$, 300 MHz): δ (ppm)=1.12 (6H, m), 1.57 (4H, m), 1.82 (4H, m), 1.95 (12H, s), 2.80 (4H, t), 6.92 (2H, d), 7.17 (2H, t), 7.25 (4H, s), 7.35 (2H, t), 7.73 (2H, s), 8.20 (4H, d).

Example 2

Synthesis of Compound 4

[Chemical Formula 97]

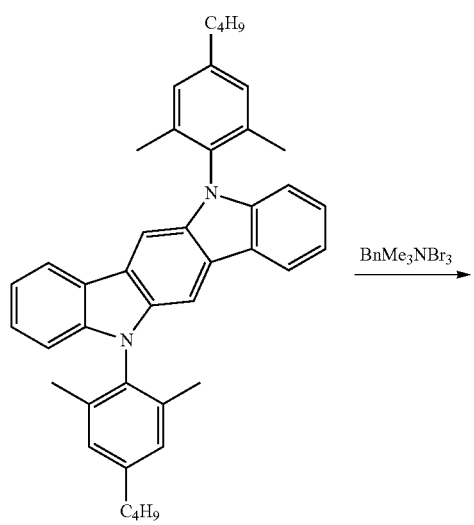

Compound 3

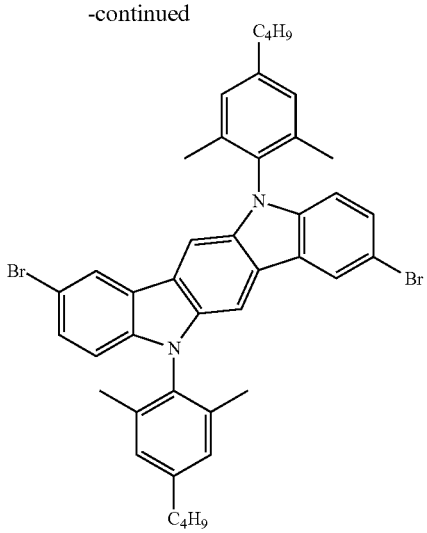

Compound 4

An argon gas atmosphere was prepared in a reaction vessel equipped with a stirrer, then, the compound 3 (3.7 g), chloroform (700 mL) and pyridine (2.0 g) were added, and the mixture was stirred at room temperature for 30 minutes. Thereafter, the whole reaction vessel was light-shielded, benzyltrimethylammonium bromide (5.04 g) was added, and the mixture was stirred at room temperature for 5 hours. Thereafter, to this was added water, then, a saturated sodium sulfite aqueous solution was added until the color of bromine disappeared. Thereafter, to this was added chloroform, and the mixture was stirred at room temperature. Thereafter, the aqueous layer was separated, and the organic layer was washed with water once and with a saturated sodium chloride aqueous solution once. The resultant washing liquid was concentrated to obtain a coarse product. The resultant composition was recrystallized using chloroform, thereby obtaining 0.5 g of a compound 4 (yield: 18%, purity: 99.3%) as a pale yellow solid.

LC-MS (APCI, positive): [M+H]$^+$ 733

$^1$H-NMR (THF-d$_6$, 300 MHz): δ (ppm)=0.95 (6H, m), 1.55 (4H, m), 1.85 (4H, m), 1.93 (12H, s), 2.79 (4H, t), 6.88 (2H, d), 7.27 (4H, s), 7.50 (2H, d), 7.79 (2H, s), 8.46 (2H, s).

Synthesis Example 2

Synthesis of Compound 6

[Chemical Formula 98]

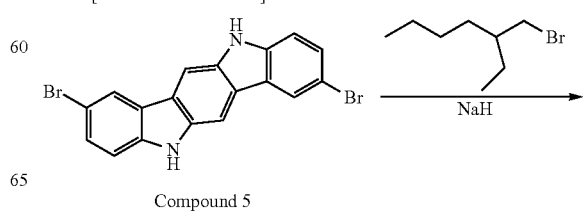

Compound 5

-continued

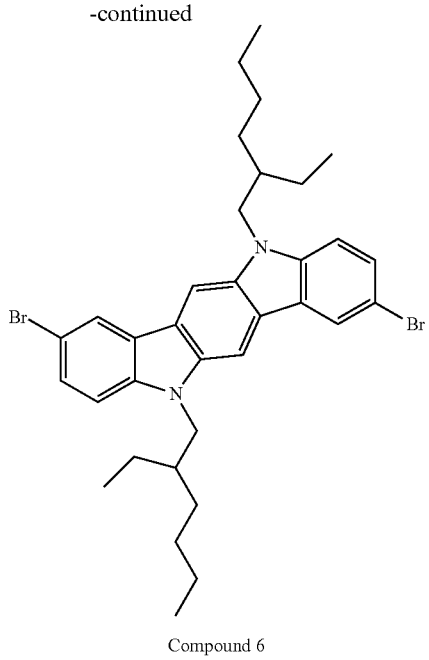

Compound 6

A nitrogen gas atmosphere was prepared in a reaction vessel equipped with a stirrer, then, a compound 5 (11.2 g) synthesized according to a method described in "Tetrahedron 68 (2012) 9788_9794" and tetrahydrofuran (250 mL) were added, and the mixture was cooled down to 0° C. Thereafter, to this was added sodium hydride (2.6 g), and the mixture was stirred at 0° C. for 30 minutes. Thereafter, into this was dropped 2-ethylhexyl bromide (20.7 g), and after completion of heat generation, the mixture was heated up to 50° C. and stirred at 50° C. for 24 hours. The resultant reaction liquid was cooled down to 0° C., hydrochloric acid water (1 mol/L) was added, and the mixture was stirred at 0° C. for 30 minutes. Thereafter, the mixture was filtrated through a filter pre-coated with Celite. The resultant filtrate was combined with a washing liquid obtained by washing the resultant residue with toluene, then, the aqueous layer was separated, and the resultant organic layer was washed with water. The resultant organic layer was concentrated to obtain a coarse product. The resultant coarse product was washed with isopropanol, then, recrystallized using a mixed solvent of isopropanol and toluene, thereby obtaining 6.9 g of a compound 6 as a white solid.

LC-MS (APCI, positive): [M+H]$^+$ 637

Example 3

Synthesis of Polymer Compound 1

[Chemical Formula 99]

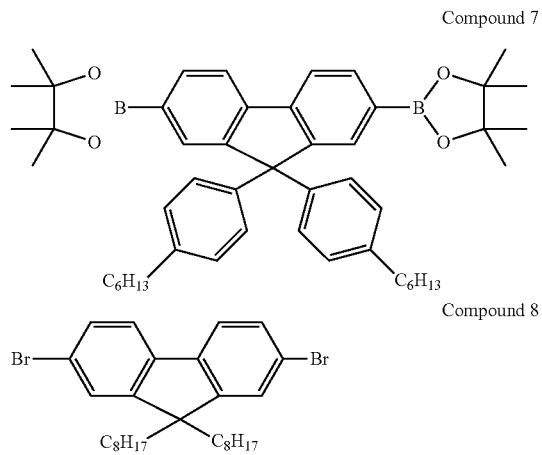

Compound 7

Compound 8

A compound 7 was synthesized according to a method described in JP-A No. 2011-174061.

A compound 8 was synthesized according to a method described in JP-A No. 2006-257094.

(Step 1) An inert gas atmosphere was prepared in a reaction vessel, then, the compound 7 (1.0811 g), the compound 8 (0.7666 g), the compound 4 (0.1111 g), dichlorobis(tris-o-methoxyphenylphosphine)palladium (1.3 mg) and toluene (40 mL) were added, and the mixture was heated at 105° C.

(Step 2) Thereafter, into this was dropped a 20 wt % tetraethylammonium hydroxide aqueous solution (5 mL), and the mixture was refluxed for 5 hours.

(Step 3) Thereafter, to this were added phenylboronic acid (36.6 mg) and dichlorobis(tris-o-methoxyphenylphosphine)palladium (1.3 mg), and the mixture was refluxed for 14 hours.

(Step 4) Thereafter, to this was added a sodium diethyldithiacarbamate aqueous solution, and the mixture was stirred at 80° C. for 2 hours. After cooling, the reaction liquid was washed with water twice, with a 3 wt % acetic acid aqueous solution twice and with water twice, and the resultant solution was dropped into methanol. The resultant precipitate was dissolved in toluene, and the solution was purified by passing through an alumina column and a silica gel column in this order. The resultant solution was dropped into methanol, the mixture was stirred, then, the resultant precipitate was isolated by filtration and dried, thereby obtaining 1.12 g of a polymer compound 1. The polymer compound 1 had a Mn of $1.1 \times 10^5$ and a Mw of $2.7 \times 10^5$.

The polymer compound 1 is a copolymer constituted of a constitutional unit derived from the compound 7, a constitutional unit derived from the compound 8 and a constitutional unit derived from the compound 4 at a molar ratio of 50:45:5 according to the theoretical values calculated from the amounts of the charged raw materials.

Comparative Example 1

Synthesis of Polymer Compound 2

A polymer compound 2 (1.09 g) was obtained in the same manner as for synthesis of the polymer compound 1 excepting that (Step 1) in synthesis of the polymer compound 1 was changed to "An inert gas atmosphere was prepared in a reaction vessel, then, the compound 7 (1.0811 g), the compound 8 (0.7666 g), the compound 6 (0.0976 g), dichlorobis(triphenylphosphine)palladium (1.3 mg) and toluene (40 ml) were added, and the mixture was heated at 105° C.". The polymer compound 2 had a Mn of $1.0 \times 10^5$ and a Mw of $2.8 \times 10^5$ The polymer compound 2 is a copolymer constituted of a constitutional unit derived from the compound 7, a constitutional unit derived from the compound 8 and a constitutional unit derived from the compound 6 at a molar ratio of 50:45:5 according to the theoretical values calculated from the amounts of the charged raw materials.

Synthesis Example 3

Synthesis of Polymer Compound 3

[Chemical Formula 100]

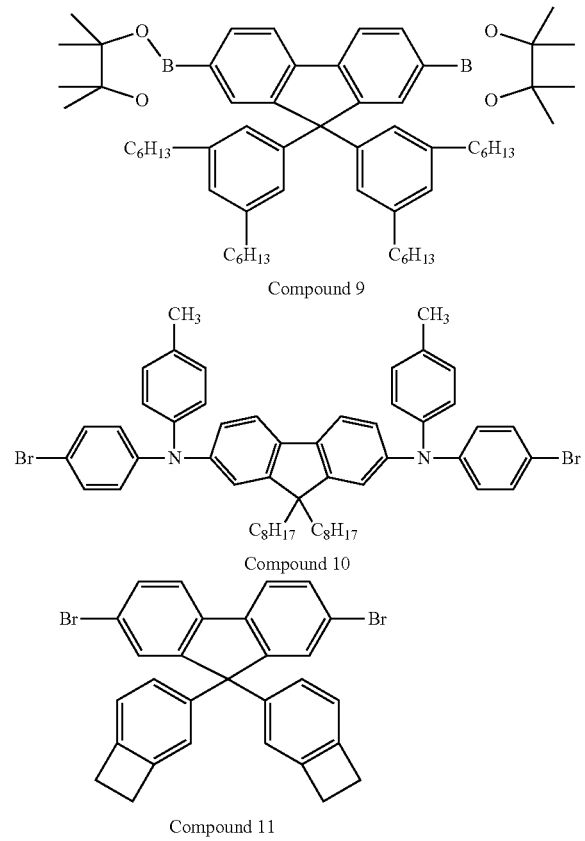

Compound 9

Compound 10

Compound 11

A compound 9 was synthesized according to a method described in JP-A No. 2011-174062.

A compound 10 was synthesized according to a method described in Japanese Patent Application National Publication No. 2007-512249.

A compound 11 was synthesized according to a method described in JP-A No. 2008-106241.

A polymer compound 3 (3.12 g) was obtained in the same manner as for synthesis of the polymer compound 1 excepting that (Step 1) in synthesis of the polymer compound 1 was changed to "An inert gas atmosphere was prepared in a reaction vessel, then, the compound 9 (2.7027 g), the compound 8 (0.2459 g), the compound 10 (1.6509 g), the compound 11 (0.2409 g), dichlorobis(triphenylphosphine) palladium (2.1 mg) and toluene (62 ml) were mixed, and heated at 105° C.", (Step 2) in synthesis of the polymer compound 1 was changed to "Thereafter, into this was dropped a 20 wt % tetraethylammonium hydroxide aqueous solution (10 mL), and the mixture was refluxed for 4.5 hours.", and (Step 3) in synthesis of the polymer compound 1 was changed to "Thereafter, to this were added phenylboronic acid (36.6 mg) and dichlorobis(triphenylphosphine) palladium (2.1 mg), and the mixture was refluxed for 14 hours.". The polymer compound 3 had a Mn of $7.8 \times 10^4$ and a Mw of $2.6 \times 10^5$.

The polymer compound 3 is a copolymer constituted of a constitutional unit derived from the compound 9, a constitutional unit derived from the compound 8, a constitutional unit derived from the compound 10 and a constitutional unit derived from the compound 11 at a molar ratio of 50:12.5:30:7.5 according to the theoretical values calculated from the amounts of the charged raw materials.

Example D1

Fabrication and Evaluation of Light Emitting Device D1

A glass substrate was attached with an ITO film with a thickness of 45 nm by a sputtering method, to form an anode. On the anode, a polythiophene•sulfonic acid type hole injection agent (trade name: AQ-1200, manufactured by Plectronics) was spin-coated to form a film with a thickness of 35 nm, and the film was heated on a hot plate at 170° C. for 15 minutes under an air atmosphere, to form a hole injection layer.

The polymer compound 3 was dissolved at a concentration of 0.7 wt % in xylene, to prepare a xylene solution. This xylene solution was spin-coated to form a film with a thickness of 20 nm on the hole injection layer, and the film was heated on a hot plate at 180° C. for 60 minutes under a nitrogen gas atmosphere, to form a hole transporting layer.

The polymer compound 1 was dissolved at a concentration of 1.2 wt % in xylene, to prepare a xylene solution. This xylene solution was spin-coated to form a film with a thickness of 60 nm on the hole transporting layer, and the film was heated at 150° C. for 10 minutes under a nitrogen gas atmosphere, to form a light emitting layer.

The substrate carrying the light emitting layer formed was placed in a vapor deposition machine, the pressure was reduced to $1.0 \times 10^{-4}$ Pa or less, then, as a cathode, sodium fluoride was vapor-deposited with a thickness of about 4 nm on the light emitting layer, then, aluminum was vapor-deposited with a thickness of about 80 nm on this. Thereafter, sealing with a glass substrate was performed, to fabricate a light emitting device D1.

When voltage was applied to the light emitting device D1, EL emission was observed, and the light emission efficiency at 1000 cd/m² was 4.3 cd/A, the emission spectrum peak wavelength was 450 nm and the CIE chromaticity coordinate (x, y) was (0.16, 0.12).

Comparative Example CD1

Fabrication and Evaluation of Light Emitting Device CD1

A light emitting device CD1 was fabricated in the same manner as in Example D1 excepting that the polymer compound 2 was used instead of the polymer compound 1 in Example D1.

When voltage was applied to the light emitting device CD1, EL emission was observed, and the light emission efficiency at 1000 cd/m$^2$ was 3.8 cd/A, the emission spectrum peak wavelength was 455 nm and the CIE chromaticity coordinate (x, y) was (0.15, 0.13).

A comparison of the light emitting device D1 with the light emitting device CD1 denoted that a light emitting device produced by using the polymer compound of the present invention was excellent in light emission efficiency.

Example 4

Synthesis of Compound 12

30 minutes. Thereafter, to this were added tris(dibenzylideneacetone)dipalladium(0) (0.12 g) and di-tert-butylphenylphosphine (0.11 g), then, the compound 2 (1.4 g) and toluene (28 mL) were added, then, the mixture was stirred at 105° C. for 1.5 hours. The resultant reaction liquid was cooled down to room temperature, then, water and toluene were added, and the mixture was stirred at room temperature. The organic layer was analyzed by HPLC (high performance liquid chromatography) to resultantly observe generation of a compound 12 as the target compound at a yield of 97%. Thereafter, the aqueous layer was separated, and the organic layer was washed with a saturated sodium chloride aqueous solution. To the resultant organic layer was added magnesium sulfate, then, the layer was filtrated, and concentrated to obtain a coarse product. The resultant coarse product was washed with heptane several times, then, recrystallized using toluene, thereby obtaining 1.0 g of a compound 12 (yield: 75%, purity: 99.3%) as a white solid.

$^1$H-NMR (THF-d$_6$, 300 MHz): δ (ppm)=1.08 (6H, m), 1.57 (4H, m), 1.85 (4H, m), 2.85 (4H, t), 7.21 (2H, m), 7.40 (4H, m), 7.58 (4H, d), 7.67 (4H, d), 8.19 (4H, m).

Comparative Example 2

Synthesis of Compound 14

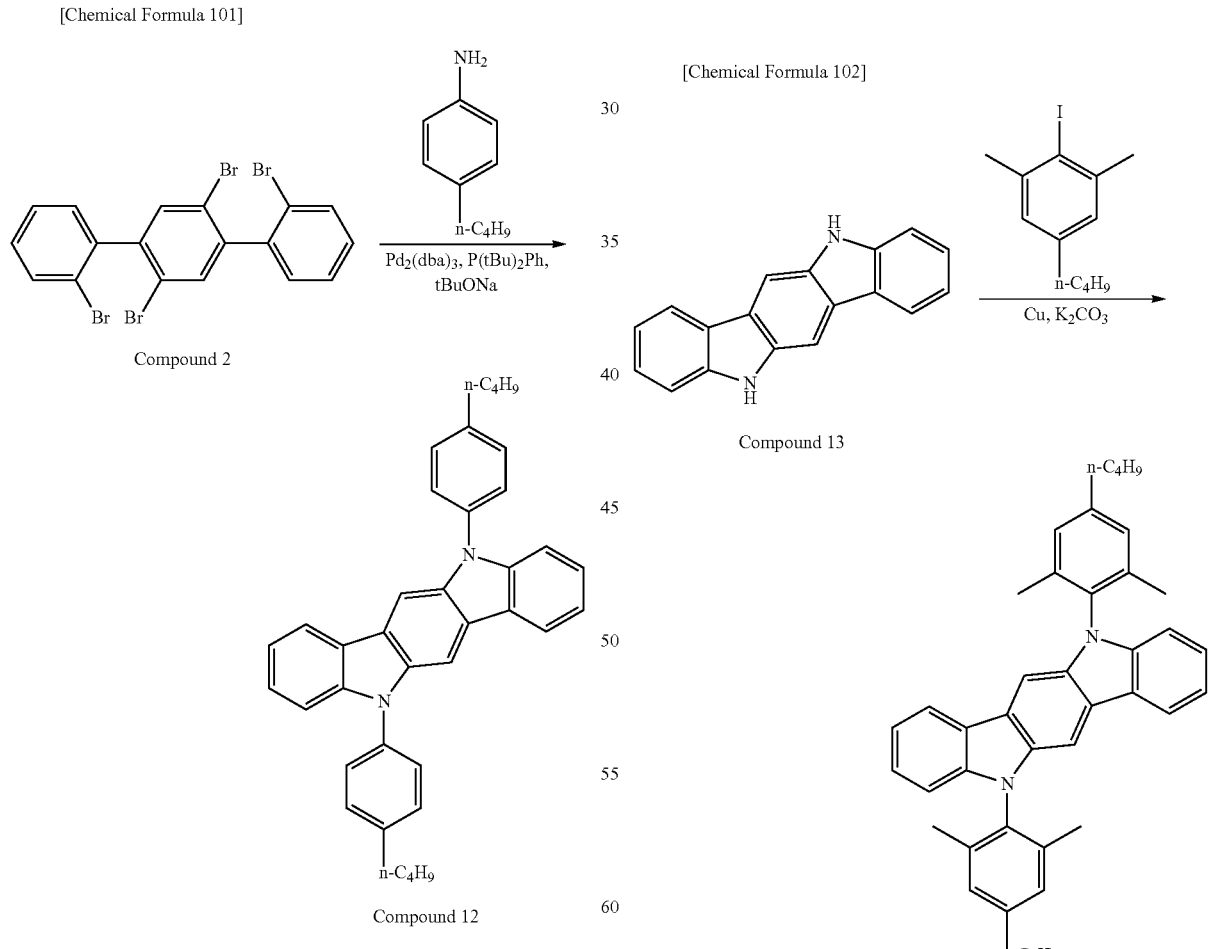

[Chemical Formula 101]

Compound 2

Compound 12

[Chemical Formula 102]

Compound 13

Compound 14

A nitrogen gas atmosphere was prepared in a reaction vessel equipped with a stirrer, then, 4-n-butylaniline (0.9 g), sodium tert-butoxide (1.5 g) and tert-butanol (1.0 ml) were added. Thereafter, to this was added toluene (7 mL), and the mixture was heated up to 105° C., then, stirred at 105° C. for A nitrogen gas atmosphere was prepared in a reaction vessel equipped with a stirrer, then, a compound 13 (0.6 g)

synthesized according to a method described in "JP-A No. 2011-216484", 2,6-dimethyl-4-n-butyliodobenzene (2.1 g), copper (1.3 g), potassium carbonate (1.4 g) and tetraethylene glycol dimethyl ether (16 ml) were added, and the mixture was stirred at 180° C. for 28 hours. The resultant reaction liquid was cooled down to room temperature, then, water and toluene were added, and the mixture was stirred at room temperature. The organic layer was analyzed by HPLC (high performance liquid chromatography) to resultantly observe no detection of a compound 14 as the target compound.

Comparative Example 3

Synthesis of Compound 15

[Chemical Formula 103]

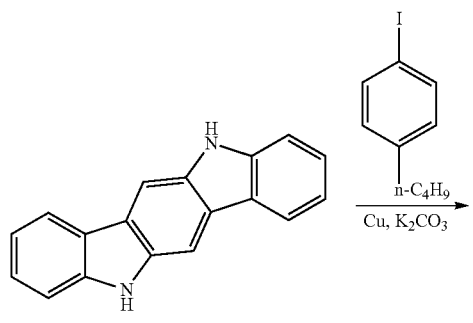

Compound 13

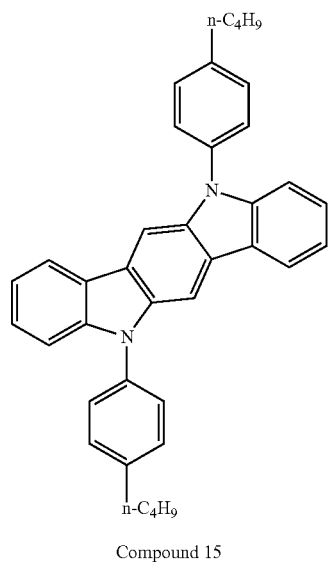

Compound 15

A nitrogen gas atmosphere was prepared in a reaction vessel equipped with a stirrer, then, a compound 13 (0.8 g) synthesized according to a method described in "JP-A No. 2011-216484", 4-n-butyliodobenzene (2.3 g), copper (1.5 g), potassium carbonate (1.6 g) and tetraethylene glycol dimethyl ether (19 ml) were added, and the mixture was stirred at 180° C. for 31 hours. The resultant reaction liquid was cooled down to room temperature, then, water and toluene were added, and the mixture was stirred at room temperature. The resultant organic layer was analyzed HPLC (high performance liquid chromatography) to resultantly observe generation of a compound 15 as the target compound at a yield of 85%. Thereafter, the aqueous layer was separated, and the organic layer was washed with a saturated sodium chloride aqueous solution. To the resultant organic layer was added magnesium sulfate, then, the layer was filtrated, and concentrated to obtain a coarse product. The resultant coarse product was washed with heptane several times, then, recrystallized using toluene, thereby obtaining 0.6 g of a compound 15 (yield: 35%, purity: 95.8%) as a white solid.

$^1$H-NMR (THF-$d_6$, 300 MHz): δ (ppm)=1.08 (6H, m), 1.57 (4H, m), 1.85 (4H, m), 2.85 (4H, t), 7.21 (2H, m), 7.40 (4H, m), 7.58 (4H, d), 7.67 (4H, d), 8.19 (4H, m).

TABLE 2

|  | target compound | reaction time | yield (isolated) |
| --- | --- | --- | --- |
| Example 1 | compound 3 | 2.5 hours | 77% |
| Example 4 | compound 12 | 1.5 hours | 75% |
| Comparative Example 2 | compound 14 | 28 hours | not detected in step before isolation |
| Comparative Example 3 | compound 15 | 31 hours | 35% |

A comparison of Example 1 and Example 4 with Comparative Example 2 and Comparative Example 3 denoted that the production method of the present invention is a production method excellent in yield.

INDUSTRIAL APPLICABILITY

The present invention can provide a polymer compound which is useful for production of a light emitting device excellent in light emission efficiency. Also, the present invention can provide a compound which is useful for production of the polymer compound. Further, the present invention can provide a composition containing the polymer compound and a light emitting device obtained by using the polymer compound.

Additionally, the present invention can provide a production method of an indrocarbazole compound excellent in yield. Still further, according to a preferable embodiment of the present invention, a production method of an indrocarbazole compound excellent in reaction speed can be provided.

The invention claimed is:

1. A polymer compound comprising a constitutional unit represented by the following formula (1-1) and a constitutional unit represented by the following formula (Y):

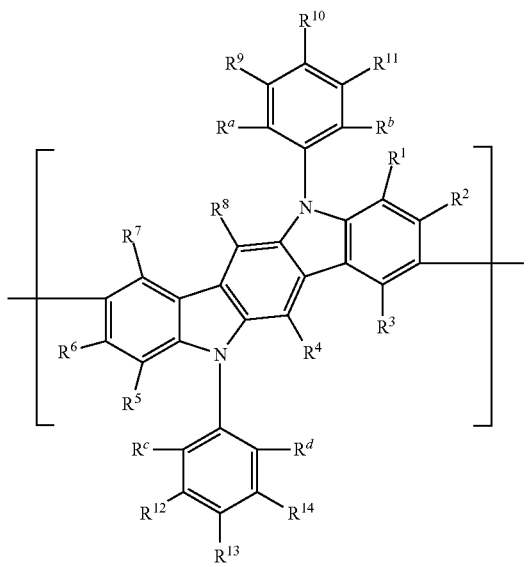

(1-1)

wherein
R¹, R², R³, R⁴, R⁵, R⁶, R⁷ and R⁸ represent a hydrogen atom
R¹⁰ and R¹³ each independently represent a methyl group, a methoxy group, an aryl group, an aryloxy group or a monovalent heterocyclic group, each having no substituent,
R⁹, R¹¹, R¹² and R¹⁴ represent a hydrogen atom, and
R$^a$, R$^b$, R$^c$ and R$^d$ each independently represent a methyl group, a methoxy group, an aryl group, an aryloxy group or a monovalent heterocyclic group, each having no substituent:

   (Y)

wherein Ar$^{Y1}$ represents an arylene group, a divalent heterocyclic group or a divalent group in which at least one arylene group and at least one divalent heterocyclic group are bonded directly to each other, the foregoing groups each optionally having a substituent.

2. The polymer compound according to claim 1, wherein R$^a$, R$^b$, R$^c$ and R$^d$ are each a methyl group having no substituent.

3. The polymer compound according to claim 1, wherein the constitutional unit represented by the formula (Y) is a constitutional unit represented by the following formula (Y-2):

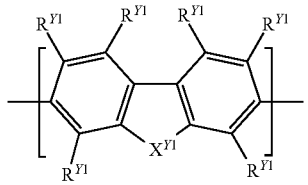   (Y-2)

wherein
each R$^{Y1}$ represents a hydrogen atom, an alkyl group, a cycloalkyl group, an alkoxy group, a cycloalkoxy group, an aryl group or a monovalent heterocyclic group, the foregoing groups each optionally having a substituent, and the plurality of R$^{Y1}$ may be the same or different, with the proviso that adjacent groups R$^{Y1}$ may be combined together to form a ring together with the carbon atoms to which they are attached, and X$^{Y1}$ represents a group represented by —C(R$^{Y2}$)₂—, a group represented by —C(R$^{Y2}$)=C(R$^{Y2}$)— or a group represented by —C(R$^{Y2}$)₂—C(R$^{Y2}$)₂—, wherein each R$^{Y2}$ represents a hydrogen atom, an alkyl group, a cycloalkyl group, an alkoxy group, a cycloalkoxy group, an aryl group or a monovalent heterocyclic group, the foregoing groups each optionally having a substituent, and the plurality of R$^{Y2}$ may be the same or different, with the proviso that groups R$^{Y2}$ may be combined together to form a ring together with the carbon atoms to which they are attached.

4. The polymer compound according to claim 1, wherein the constitutional unit represented by the formula (Y) is a constitutional unit represented by the following formula (Y-5), (Y-6) or (Y-7):

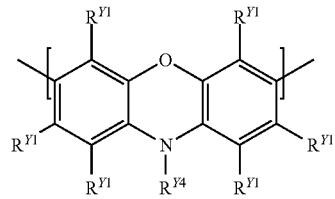   (Y-5)

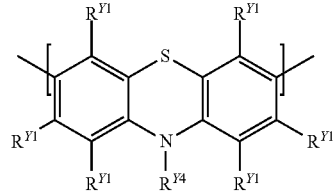   (Y-6)

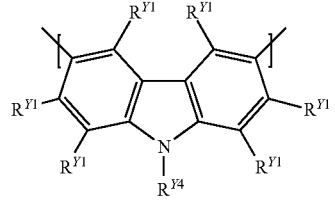   (Y-7)

wherein
each R$^{Y1}$ represents a hydrogen atom, an alkyl group, a cycloalkyl group, an alkoxy group, a cycloalkoxy group, an aryl group or a monovalent heterocyclic group, the foregoing groups each optionally having a substituent, and the plurality of R$^{Y1}$ may be the same or different, with the proviso that adjacent groups R$^{Y1}$ may be combined together to form a ring together with the carbon atoms to which they are attached, and R$^{Y4}$ represents a hydrogen atom, an alkyl group, a cycloalkyl group, an alkoxy group, a cycloalkoxy group, an aryl group or a monovalent heterocyclic group, the foregoing groups each optionally having a substituent.

5. The polymer compound according to claim 1, further comprising a constitutional unit represented by the following formula (X):

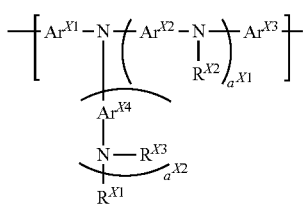

(X)

wherein
$a^{X1}$ and $a^{X2}$ each independently represent an integer of 0 or more,
$Ar^{X1}$ and $Ar^{X3}$ each independently represent an arylene group or a divalent heterocyclic group, these groups each optionally having a substituent,
$Ar^{X2}$ and $Ar^{X4}$ each independently represent an arylene group, a divalent heterocyclic group or a divalent group in which at least one arylene group and at least one divalent heterocyclic group are bonded directly to each other, and these groups each optionally having a substituent, and
$R^{X1}$, $R^{X2}$ and $R^{X3}$ each independently represent a hydrogen atom, an alkyl group, a cycloalkyl group, an aryl group or a monovalent heterocyclic group, the foregoing groups each optionally having a substituent.

6. The polymer compound according to claim 1, wherein the content of the constitutional unit represented by the formula (1) is 0.1 to 50 mol % with respect to the total content of constitutional units contained in the polymer compound.

7. A compound represented by the following formula (M-1-2):

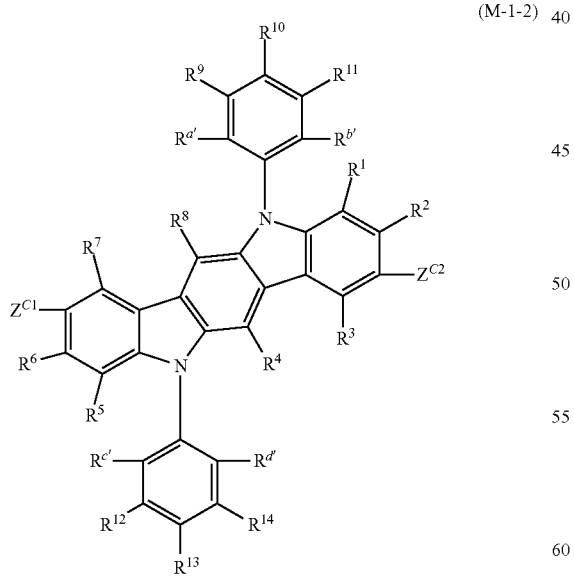

(M-1-2)

wherein
$R^1$, $R^2$, $R^3$, $R^4$, $R^5$, $R^6$, $R^7$ and $R^8$ represent a hydrogen atom,
$R^{10}$ and $R^{13}$ each independently represent a hydrogen atom, a methyl group, a methoxy group, an aryl group, an aryloxy group or a monovalent heterocyclic group, each having no substituent,
$R^9$, $R^{11}$, $R^{12}$, and $R^{14}$ represent a hydrogen atom,
$R^{a\prime}$, $R^{b\prime}$, $R^{c\prime}$ and $R^{d\prime}$ each independently represent a methyl group, a methoxy group, an aryl group, an aryloxy group or a monovalent heterocyclic group, each having no substituent, and
$Z^{C1}$ and $Z^{C2}$ each independently represent a group selected from the group consisting of the following Group A of substituents and Group B of substituents:

wherein the Group A substituents are selected from a hydrogen atom, a chlorine atom, a bromine atom, an iodine atom, and a group represented by —O—S(=O)$_2$ $R^{C1}$, wherein $R^{C1}$ represents an alkyl group, a cycloalkyl group or an aryl group, the foregoing groups each optionally having a substituent, and wherein the Group B substituents are selected from:

a group represented by —B(OR$^{C2}$)$_2$, wherein each $R^{C2}$ represents a hydrogen atom, an alkyl group, a cycloalkyl group or an aryl group, the foregoing groups each optionally having a substituent, with the proviso that the plurality of $R^{C2}$ may be the same or different and may be combined together to form a cyclic structure together with the oxygen atoms to which they are attached;

a group represented by —BF$_3$ Q', wherein Q' represents Li, Na, K, Rb or Cs;

a group represented by —MgY', wherein Y' represents a chlorine atom, a bromine atom or an iodine atom;

a group represented by —ZnY", wherein Y" represents a chlorine atom, a bromine atom or an iodine atom; and a group represented by —Sn(R$^{C3}$)$_3$, wherein each $R^{C3}$ represents a hydrogen atom, an alkyl group, a cycloalkyl group or an aryl group, the foregoing groups each optionally having a substituent, with the proviso that the plurality of $R^{C3}$ may be the same or different and may be combined together to form a cyclic structure together with the tin atom to which they are attached.

8. A composition comprising
the polymer compound according to claim 1 and
at least one material selected from the group consisting of a hole transporting material, a hole injection material, an electron transporting material, an electron injection material, a light emitting material, an antioxidant, and a solvent.

9. A light emitting device produced by using the polymer compound according to claim 1.

10. A method for producing a compound represented by the following formula (M-1'), the method comprising:
a step of making a compound represented by the following formula (Z) and a compound represented by the following formula (2) undergo amination in the presence of a transition metal complex having a phosphine ligand, a base and a solvent:

$$R^C—NH_2 \quad (Z)$$

wherein $R^C$ represents an aryl group or a monovalent heterocyclic group, these groups each optionally having a substituent:

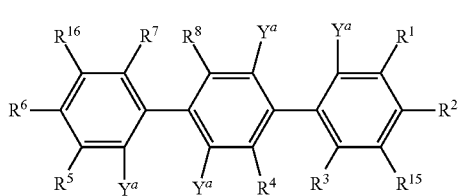

(2)

wherein
- $R^1$, $R^2$, $R^3$, $R^4$, $R^5$, $R^6$, $R^7$ and $R^8$ each independently represent a hydrogen atom, an alkyl group, a cycloalkyl group, an alkoxy group, a cycloalkoxy group, an aryl group, an aryloxy group or a monovalent heterocyclic group, the foregoing groups each optionally having a substituent,
- $R^{15}$ and $R^{16}$ each independently represent an alkyl group, a cycloalkyl group, an alkoxy group, a cycloalkoxy group, an aryl group, an aryloxy group, a monovalent heterocyclic group or a group selected from the group consisting of the following Group A of substituents and Group B of sub stituents, the foregoing groups each optionally having a substituent,
- with the proviso that $R^1$ and $R^2$, $R^2$ and $R^{15}$, $R^{15}$ and $R^3$, $R^3$ and $R^4$, $R^5$ and $R^6$, $R^6$ and $R^{16}$, $R^{16}$ and $R^7$, and $R^7$ and $R^8$ each may be combined together to form a ring together with the carbon atoms to which they are attached, and
- each $Y^a$ represents a chlorine atom, a bromine atom, an iodine atom or —O—S(=O)$_2$R$^{C1}$, and R$^{C1}$ represents an alkyl group, a cycloalkyl group or an aryl group, the foregoing groups each optionally having a substituent, and the plurality of $Y^a$ may be the same or different:

wherein the Group A substituents are selected from a hydrogen atom, a chlorine atom, a bromine atom, an iodine atom, and a group represented by —O—S(=O)$_2$R$^{C1}$, wherein R$^{C1}$ represents an alkyl group, a cycloalkyl group or an aryl group, the foregoing groups each optionally having a substituent, and wherein the Group B substituents are selected from:
- a group represented by —B(OR$^{C2}$)$_2$, wherein each R$^{C2}$ represents a hydrogen atom, an alkyl group, a cycloalkyl group or an aryl group, the foregoing groups each optionally having a substituent, with the proviso that the plurality of R$^{C2}$ may be the same or different and may be combined together to form a cyclic structure together with the oxygen atoms to which they are attached;
- a group represented by —BF$_3$Q', wherein Q' represents Li, Na, K, Rb or Cs;
- a group represented by —MgY', wherein Y' represents a chlorine atom, a bromine atom or an iodine atom;
- a group represented by —ZnY", wherein Y" represents a chlorine atom, a bromine atom or an iodine atom; and
- a group represented by —Sn(R$^{C3}$)$_3$, wherein each R$^{C3}$ represents a hydrogen atom, an alkyl group, a cycloalkyl group or an aryl group, the foregoing groups each optionally having a substituent, with the proviso that the plurality of R$^{C3}$ may be the same or different and may be combined together to form a cyclic structure together with the tin atom to which they are attached:

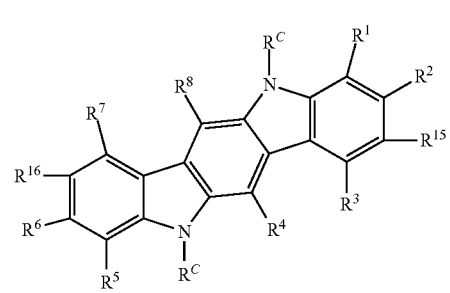

(M-1')

wherein $R^1$, $R^2$, $R^3$, $R^4$, $R^5$, $R^6$, $R^7$, $R^8$, $R^{15}$, $R^{16}$ and each $R^C$ are as defined above, and the plurality of $R^C$ may be the same or different.

11. The method for producing a compound according to claim 10, wherein the compound represented by the formula (M-1') is a compound represented by the following formula (M-1'-1):

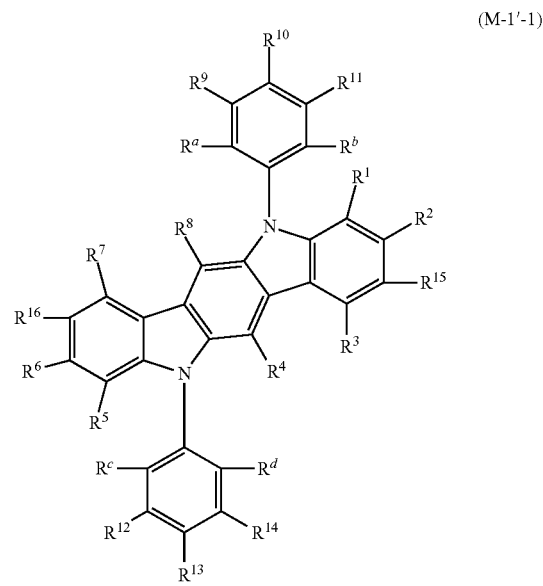

(M-1'-1)

wherein
- $R^1$, $R^2$, $R^3$, $R^4$, $R^5$, $R^6$, $R^7$, $R^8$, $R^{15}$ and $R^{16}$ are as defined above, and
- $R^9$, $R^{10}$, $R^{11}$, $R^{12}$, $R^{13}$, $R^{14}$, $R^a$, $R^b$, $R^c$ and $R^d$ each independently represent a hydrogen atom, an alkyl group, a cycloalkyl group, an alkoxy group, a cycloalkoxy group, an aryl group, an aryloxy group or a monovalent heterocyclic group, the foregoing groups each optionally having a sub stituent, with the proviso that $R^9$ and $R^{10}$, $R^{10}$ and $R^{11}$, $R^{12}$ and $R^{13}$, and $R^{13}$ and $R^{14}$ each may be combined together to form a ring together with the carbon atoms to which they are attached.

12. The method for producing a compound according to claim 11, wherein $R^a$, $R^b$, $R^c$ and $R^d$ are each an alkyl group optionally having a substituent.

13. A compound represented by the following formula (M-1-2):

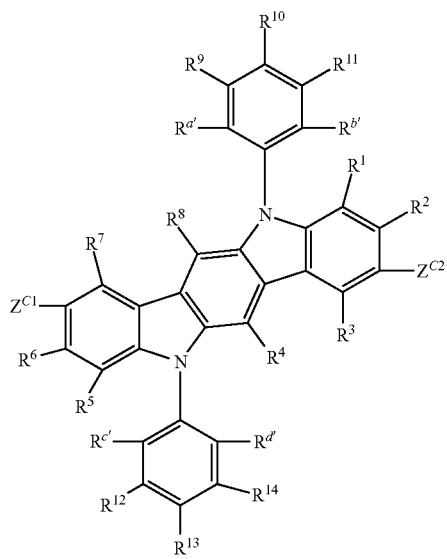

(M-1-2)

wherein $R^1$, $R^2$, $R^3$, $R^4$, $R^5$, $R^6$, $R^7$ and $R^8$ each independently represent a hydrogen atom, an alkyl group, a cycloalkyl group, an alkoxy group, a cycloalkoxy group, an aryl group, an aryloxy group or a monovalent heterocyclic group, each optionally having a substituent, with the proviso that $R^1$ and $R^2$, $R^3$ and $R^4$, $R^5$ and $R^6$, and $R^7$ and $R^8$ each may be combined together to form a ring together with the carbon atoms to which they are attached, $R^9$, $R^{10}$, $R^{11}$, $R^{12}$, $R^{13}$ and $R^{14}$ each independently represent a hydrogen atom, an alkyl group, a cycloalkyl group, an alkoxy group, a cycloalkoxy group, an aryl group, an aryloxy group or a monovalent heterocyclic group, each optionally having a substituent, with the proviso that $R^9$ and $R^{10}$, $R^{10}$ and $R^{11}$, $R^{12}$ and $R^{13}$, and $R^{13}$ and $R^{14}$ each may be combined together to form a ring together with the carbon atoms to which they are attached, $R^{a\prime}$, $R^{b\prime}$, $R^{c\prime}$ and $R^{d\prime}$ each independently represent an alkyl group, a cycloalkyl group, an alkoxy group, a cycloalkoxy group, an aryl group, an aryloxy group or a monovalent heterocyclic group, each optionally having a substituent, and $Z^{C1}$ and $Z^{C2}$ represent a hydrogen atom.

* * * * *